United States Patent
Patel et al.

(10) Patent No.: US 6,521,602 B1
(45) Date of Patent: Feb. 18, 2003

(54) ANTI-NEOPLASTIC COMPOSITIONS AND USES THEREOF

(75) Inventors: Salil Patel, Cupertino, CA (US); James McArthur, San Carlos, CA (US); Jeno Gyuris, Winchester, MA (US); Michael J. Mendez, El Granada, CA (US); Mitchell H. Finer, Woodside, CA (US)

(73) Assignees: GPC Biotech Inc., Waltham, MA (US); Cell Genesys, Inc., Foster City, CA (US)

( * ) Notice: Subject to any disclaimer, the term of this patent is extended or adjusted under 35 U.S.C. 154(b) by 0 days.

(21) Appl. No.: 09/516,065

(22) Filed: Mar. 1, 2000

Related U.S. Application Data

(60) Provisional application No. 60/122,974, filed on Mar. 1, 1999, provisional application No. 60/128,271, filed on Apr. 8, 1999, and provisional application No. 60/128,515, filed on Apr. 9, 1999.

(51) Int. Cl.⁷ ............... A61K 48/00; C12N 15/62; C12N 15/85; C12N 15/861; C12N 15/867; C12N 15/869

(52) U.S. Cl. .......... 514/44; 424/93.2; 435/320.1; 435/455; 435/456; 536/23.1; 536/23.4; 536/23.72

(58) Field of Search ............ 514/44; 424/93.2; 435/320.1, 455, 456; 536/23.1, 23.4, 23.72

(56) References Cited

U.S. PATENT DOCUMENTS 5,672,508 A  *  9/1997  Gyuris et al. ............ 435/320.1

FOREIGN PATENT DOCUMENTS

| WO | 9727297 | 7/1997 |
| WO | 9801563 | 1/1998 |
| WO | 9903508 | 1/1999 |
| WO | WO 99/06540 | * 2/1999 |

OTHER PUBLICATIONS

*Biochemical and Biophysical Research Communications.* vol. 220, pp. 703–709 (1996). Kwon et al. "The cdk2 Binding Domain of p27$^{Kip}$ Correlates with the Inhibition of the Kinase Activity of cdk2/Clyclin Complexes."

*Proc. Amer. Assn. Cancer Res.* vol. 40, p. 630 (1999). McArthur et al., "Cancer Gene Therapy with Novel Chimeric p27/p16 Tumor Suppressor Genes."

* cited by examiner

*Primary Examiner*—Scott D. Priebe
(74) *Attorney, Agent, or Firm*—Roylance, Abrams et al.

(57) ABSTRACT

Disclosed is a nucleic acid composition consisting essentially of a first nucleic acid sequence encoding a chimeric CDKi protein and a second nudeic acid sequence encoding an adenovirus E4 protein, wherein the first and second nucleic acid sequences are operably linked to at least one regulatory sequence.

11 Claims, 18 Drawing Sheets

| | | CDK4/ cyclin D1 (nM) | CDK2/ cyclin E (nM) | CDC2/ cyclin B (nM) | HALF-LIFE (HRS) | |
|---|---|---|---|---|---|---|
| | | | | | $G_0$ | As |
| p16 | 1—156 | 100 | >1000 | >1000 | ~3 | ~3 |
| p27 | 1—198 | 23 | 2.4 | 12 | ~3 | ~4.5 |
| $\Delta p27^{12\text{-}178}$ | 12—178 | 52 | 11 | 44 | <2 | <1 |
| $\Delta p27^{25\text{-}93}$ | 25—93 | 30 | 8.3 | 31 | <1 | <1 |
| W3 | 1—198 2—156 | 17 | 3.0 | 18 | ~2.5 | ~6.5 |
| W4 | 1—198/2—156 | 39 | 8.9 | 15 | | |
| W5 | 1—156 2—198 | 44 | 11 | 18 | | |
| W6 | 1—156/2—198 | 26 | 8.4 | 17 | | |
| W8 | 12—178 2—156 | 23 | 4.4 | 17 | | |
| W7 | 12—178/2—156 | 16 | 2.6 | 9.2 | ~3 | ~20 |
| W10 | 25—93 2—156 | 38 | 3.0 | 17 | | |
| W9 | 25—93/2—156 | 47 | 3.5 | 18 | ~2 | ~4.5 |
| p27 + p16 | 1—156  1—198 | 25 | 1.7 | 12 | | |

FIG. 2A

W9 NUCLEIC ACID SEQUENCE

ATGGCCAAGCCCTCGGCCTGCAGGAACCTCTT
CGGCCCGGTGGACCACGAAGAGTTAACCCGGG
ACTTGGAGAAGCACTGCAGAGACATGGAAGAG
GCGAGCCAGCGCAAGTGGAATTTCGATTTTCA
GAATCACAAACCCCTAGAGGGCAAGTACGAGT
GGCAAGAGGTGGAGAAGGGCAGCTTGCCCGAG
TTCTACTACAGACCCCGCGGGTCGAGGATCC
GGCGGCGGGGAGCAGCATGGAGCCTTCGGCTG
ACTGGCTGGCCACGGCCGCGGCCCGGGGTCGG
GTAGAGGAGGTGCGGGCGCTGCTGGAGGCGGG
GGCGCTGCCCAACGCACCGAATAGTTACGGTC
GGAGGCCGATCCAGGTCATGATGATGGGCAGC
GCCCGAGTGGCGGAGCTGCTGCTGCTCCACGG
CGCGGAGCCCAACTGCGCCGACCCCGCCACTC
TCACCCGACCCGTGCACGACGCTGCCCGGGAG
GGCTTCCTGGACACGCTGGTGGTGCTGCACCG
GGCCGGGGCGCGGCTGGACGTGCGCGATGCCT
GGGGCCGTCTGCCCGTGGACCTGGCTGAGGAG
CTGGGCCATCGCGATGTCGCACGGTACCTGCG
CGCGGCTGCGGGGGGCACCAGAGGCAGTAACC
ATGCCCGCATAGATGCCGCGGAAGGTCCCTCA
GACATCCCCGATTGA

FIG. 2B-1

W9 AMINO ACID SEQUENCE

MAKPSACRNLFGPVDHEELTRDLEKHCRDMEE
ASQRKWNFDFQNHKPLEGKYEWQEVEKGSLPE
FYYRPPRVEDPAAGSSMEPSADWLATAAARGR
VEEVRALLEAGALPNAPNSYGRRPIQVMMMGS
ARVAELLLLHGAEPNCADPATLTRPVHDAARE
GFLDTLVVLHRAGARLDVRDAWGRLPVDLAEE
LGHRDVARYLRAAAGGTRGSNHARIDAAEGPS
DIPD

FIG. 2B-2

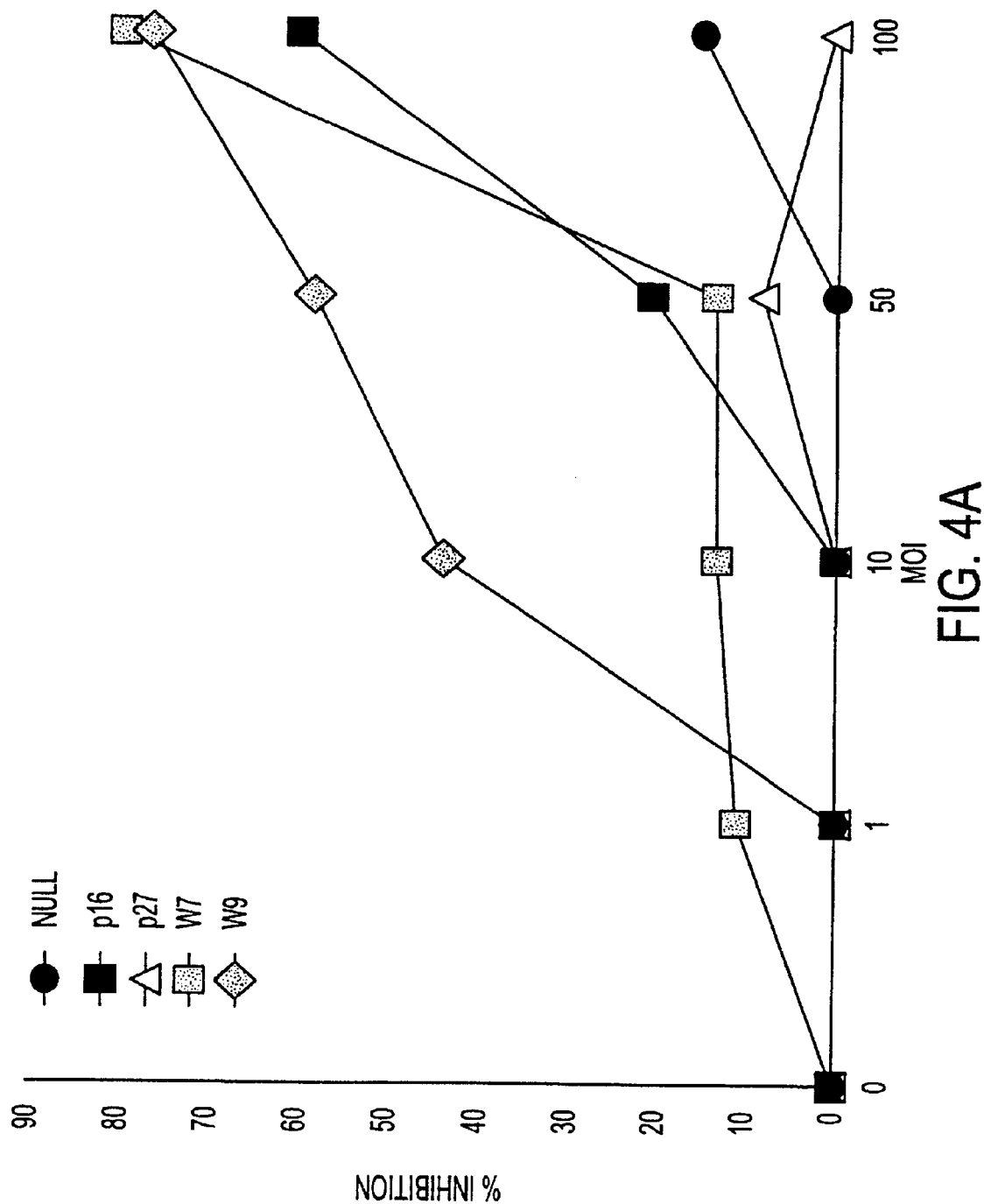

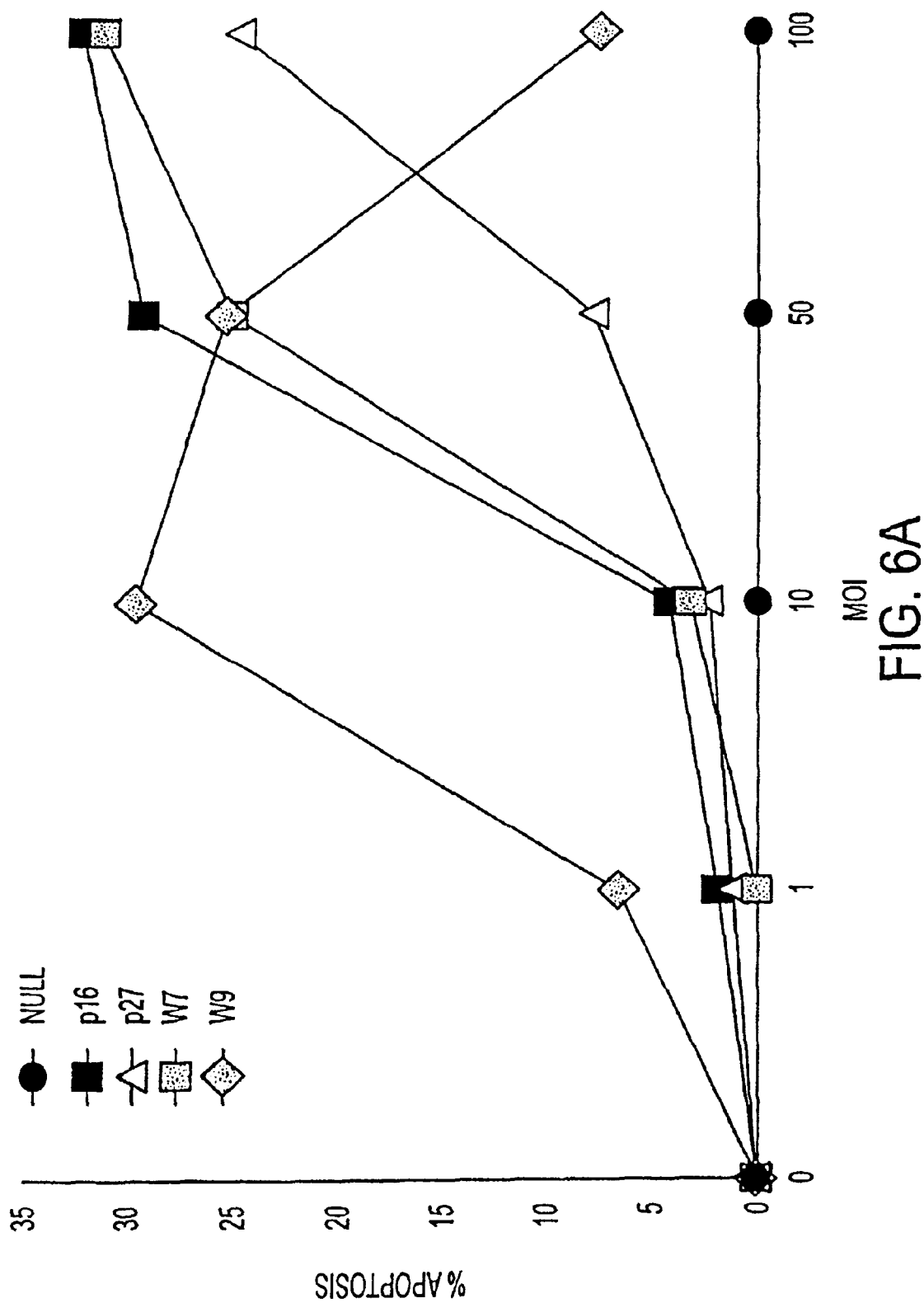

ANTI-NEOPLASTIC COMPOSITIONS AND USES THEREOF

The instant application claims benefit under 35 U.S.C. 119(e) to U.S. Ser. No. 60/122,974 filed Mar. 1, 1999; U.S. Ser. No. 60/128,271 filed Apr. 8, 1999; and U.S. Ser. No. 60/128,515 filed Apr. 9, 1999.

BACKGROUND OF THE INVENTION

The invention relates to therapy for treating neoplasia, particularly cancer.

In America, half of all men and one-third of all women will develop some form of neoplasia during their lifetimes. For example, millions of Americans are currently living with cancer or have been cured of the disease. Although cancer is frequently fatal, rapid treatment of the disease results in a better prognosis for recovery.

Neoplasia is caused by the abnormal growth and proliferation of cells in the body. While normal body cells grow, divide, and die in an orderly fashion, neoplastic cells grow and divide in a disorderly fashion. Such disorderly growth during neoplasia may be caused by abnormal dysregulation of the cell cycle leading to the hyper-proliferation of cells (Sherr (1996) *Science* 274: 1672–1677).

In eukaryotic cells, progression through the cell cycle is orchestrated by functionally distinct cydin-dependent kinases (CDK's). Complexes are formed via the association of different catalytic CDK domains and regulatory cyclin subunits. CDK4/cydin D and CDK6/cyclin D complexes regulate progression through $G_1$ phase; CDK2/cyclin E kinase regulates the $G_1$/S transition; CDK2/cyclin A complex drives the cells through S-phase; and CDC2/cyclin B complex controls the entry, and exit from mitosis (Sherr (1996) *Science* 274: 1672–1677). The activity of the CDKs is tightly regulated in response to a variety of extra- and intracellular signals, and is mediated through a combination of phosphorylation events and associations with cyclin-dependent kinase inhibitors (CDKi's) (Morgan (1995) *Nature* 374: 131–134). The redistribution of CDKi's between the different CDK/cyclin complexes during the cell cycle coordinates the timing of activation and de-activation of the kinase activities (Sherr and Roberts (1995) *Genes & Dev.* 9: 1149–1163).

Two classes of structurally distinct CDKi's, the CIP/KIP and the INK4 families, have been identified in mammalian cells. The CIP/KIP family includes p21/CIP1/WAF1, p27/KIP1, and p57/KIP2 (Sherr and Roberts, supra). CIP/KIP family members share a conserved N-terminal region of an inhibitory domain having a length of approximately 60 amino acids. The members of the CIP/KIP family are potent inhibitors of the CDK4, CDK2, and CDC2 kinases, although their over-expression in vivo predominantly leads to arrest in the $G_1$ phase of the cell cycle. The members of the INK4 family include p15/INK4a, p16/INK4b, p18/INK4c, and p19/INK4d (Serrano et al. (1993) *Nature* 366: 704–707; Hannon and Beach (1994) *Nature* 371: 257–261; Hirai et al. (1995) *Mol. Cell. Biol.* 15: 2672–2681; Chan et al. (1995) *Mol. Cell. Biol.* 15: 2682–2688; Guan et al. (1996) *Mol. Biol. Cell.* 7: 57–70). The INK4 proteins are comprised almost exclusively of the repetitions of a common structural motif, the ankyrin repeat (Bork (1993) *Proteins* 17: 363–374), and are highly specific inhibitors of the CDK4 and CDK6 associated kinases.

Biochemical analysis of the members of the CIP/KIP and INK4 families of inhibitors has suggested that their modes of action are different. p16, the prototypic member of the INK4 family, binds to both monomeric CDK4 and to the assembled, fully active CDK4/cyclin D1 kinase. The binding of p16 to CDK4 appears to prevent the formation of CDK4/cyclin D complexes, whereas binding of p16 to assembled CDK4/cyclin D complex produces a catalytically inactive ternary complex (Parry et al. (1995) *EMBO J.* 14: 503–511). p27 binds primarily to the active CDK2/cydinA and CDK2/cyclinE complexes, which leads to the formation of a catalytically inactive ternary complex (Polyak et al. (1994) *Cell* 78:1156–66; Polyak et al. (1994) *Genes & Dev.* 8: 9–22).

To inhibit cell cycle progression, the levels of the individual CDKi's must exceed the concentration of the active CDK/cyclin complexes. Control of cell proliferation has been shown to act through the regulation of the levels of various CDKi's. For example, under growth conditions that induce arrest of cell proliferation, the amount of p27 increases (Firpo et al. (1994) *Mol. Cell. Biol.* 14: 4889–4901; Kato et al. (1994) *Cell* 79: 487–496; Nourse et al. (1994) *Nature* 372: 570–573, Slingerland et al. (1994) *Mol. Cell. Biol.* 14: 3683–3694). As the cells are stimulated to reenter the cell cycle, the level of p27 is promptly reduced. Similarly, as cells become senescent, p16 gradually increases (Alcorta et al. (1996) *Proc. Natl. Acad. Sci. USA* 93: 13742–13747).

Given the large numbers of human deaths attributable to neoplasia, there is a need to develop useful methods and compositions to treat or prevent neoplasia, including hyperplasia and cancer. Moreover, given the important role that the cell cycle plays in several disease phenotypes, reagents that arrest cell growth are useful in allowing further study of the cell cycle for synchronizing and controlling growth of cells in culture.

SUMMARY OF THE INVENTION

The present features novel chimeric cyclin dependent kinase inhibitors (chimeric CDKi's) which, when combined with an adenovirus E4 protein (or active fragment thereof), not only inhibit neoplastic cell growth, but surprisingly also induce apoptosis in neoplastic cells. Using the chimeric CDKi protein, W9, apoptosis was induced in neoplastic cells regardless of their p53, Rb, p27, or p16 status. The combination of a chimeric CDKi with an adenovirus E4 protein does not induce apoptosis in most normal cells, but rather only induces cell growth arrest. These surprising discoveries have been exploited to provide the anti-neoplastic compositions and methods of the present invention.

Accordingly, in a first aspect, the invention features a nucleic acid composition consisting essentially of a first nucleic acid sequence encoding a chimeric CDKi protein and a second nucleic acid sequence encoding an adenovirus E4 protein, wherein the first and second nucleic acid sequences are operably linked to at least one regulatory sequence. Such nudeic add sequences are capable of being expressed in a cell. In certain embodiments, the chimeric CDKi protein is a W9 protein. In certain embodiments, the adenovirus E4 protein is encoded by E4orf6.

In another aspect, the invention features a composition comprising the chimeric CDKi protein/adenovirus E4 protein-encoding nudeic acid composition according to the first aspect of the invention and a pharmaceutically acceptable carrier. In one embodiment, the composition further comprises a delivery system that facilitates the internalization of the composition by a cell. Preferably, the delivery system is a recombinant virus particle. In other embodiments, the recombinant virus particle is selected from the group consisting of an adenovirus, a lentivirus, an adeno-associated virus, a retrovirus, a herpesvirus, and a vaccinia virus. Preferably, the recombinant virus particle is an adenovirus (e.g., an adenovirus lacking an entire E4 region). In another embodiment, the delivery system is a liposome.

In yet another aspect, the invention features a nucleic acid composition comprising a first nucleic acid sequence encoding a secretable, internalizable form of a chimeric CDKi protein and a second nudeic acid sequence encoding a secretable, internalizable form of an adenovirus E4 protein, wherein the first and second nudeic acid sequences are operably linked to at least one regulatory sequence. In certain embodiments, the chimeric CDKi protein is a W9 protein. In certain embodiments, the adenovirus E4 protein is encoded by E4orf6.

In another aspect, the invention features a composition comprising a nucleic acid composition comprising a first nucleic acid sequence encoding a secretable, internalizable form of a chimeric CDKi protein and a second nucleic acid sequence encoding a secretable, internalizable form of an adenovirus E4 protein, and a pharmaceutically acceptable carrier, wherein the first and second nucleic acid sequences are operably linked to at least one regulatory sequence. In certain embodiments, the composition further comprises a delivery system that facilitates the internalization of the composition by a cell. Preferably, the delivery system is a recombinant virus particle. In other embodiments, the recombinant virus particle is selected from the group consisting of an adenovirus, a lentivirus, an adeno-associated virus, a retrovirus, a herpesvirus, and a vaccinia virus. Preferably, the recombinant virus particle is an adenovirus. In another embodiment, the delivery system is a liposome.

In another aspect, the invention features a protein composition comprising a purified chimeric CDKi protein and a purified adenovirus E4 protein. In certain embodiments, the chimeric CDKi protein is a W9 protein. In certain embodiments, the adenovirus E4 protein is encoded by E4orf6.

In yet another aspect, the invention features a composition comprising a protein composition comprising a purified chimeric CDKi protein and a purified adenovirus E4 protein, and a pharmaceutically acceptable carrier. In one embodiment, the composition further comprises a delivery system that facilitates the internalization of the composition by a cell.

In still another aspect, the invention features a protein composition comprising a purified, internalizable form of a chimeric CDKi protein and a purified, internalizable form of an adenovirus E4 protein. In certain embodiments, the chimeric CDKi protein is a W9 protein. In certain embodiments, the adenovirus E4 protein is encoded by E4orf6.

In another aspect, the invention features a composition comprising a protein composition comprising a purified, internalizable form of a chimeric CDKi protein and a purified, internalizable form of an adenovirus E4 protein, and a pharmaceutically acceptable carrier.

In yet another aspect, the invention features a method for treating an animal with a neoplasm. The method includes administering to the animal a therapeutically effective amount of a composition according to the invention.

In another aspect, the invention features a cell containing a nucleic acid composition comprising a first nucleic acid sequence encoding a secretable, internalizable form of a chimeric CDKi protein and a second nucleic acid sequence encoding a secretable, internalizable form of an adenovirus E4 protein, wherein the first and second nucleic acid sequences are operably linked to at least one regulatory sequence. In certain embodiments, the chimeric CDKi protein is a W9 protein. In certain embodiments, the adenovirus E4 protein is encoded by E4orf6.

In yet another aspect, the invention features a method for treating an animal with a neoplasm, comprising introducing the nucleic acid composition comprising a first nucleic acid sequence encoding a secretable, internalizable form of a chimeric CDKi protein and a second nucleic acid sequence encoding a secretable, internalizable form of an adenovirus E4 protein, wherein the first and second nucleic acid sequences are operably linked to at least one regulatory sequence into a cell of the animal, wherein the introduced cell secretes the secretable, internalizable form of the chimeric CDKi protein and secretes the secretable, internalizable form of the adenovirus E4 protein.

In final aspect, the invention features a method for treating an animal with a neoplasm, comprising introducing the nucleic acid composition comprising a first nucleic acid sequence encoding a secretable, internalizable form of a W9 protein and a second nucleic acid sequence encoding a secretable, internalizable form of an adenovirus E4 protein, wherein the first and second nudeic acid sequences are operably linked to at least one regulatory sequence into a cell of the animal, wherein the introduced cell secretes the secretable, internalizable form of the W9 protein and secretes the secretable, internalizable form of the adenovirus E4 protein.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 2A is a diagrammatic representation showing non-limiting, representative recombinant CDK inhibitors of the invention tested in in vitro kinase assays, and the results of these assays. The p16 molecule is indicated by the open box; the p27 molecule and its derivatives are indicated by the hatched boxes; and the 15 amino acidslong $(Gly_4Ser)_3$ linker between the p16 and p27 moieties is indicated by the black boxes. Above the schematic for each molecule is the corresponding 5' and 3' amino acid from the parental molecule. The table in the middle shows the $IC_{50}$'S (in nM) of the purified inhibitors as determined by in vitro kinase assays that utilized CDK4/cyclin D1, CDK2/cyclin E, and CDC2/cyclin B kinases. At the right of FIG. 2A is listed the estimated half-life expression of the adenovirus encoded CDKi protein (in hours) as measured by pulse-chase experiments (see Example IV);

FIG. 2B is a schematic representation of the nucleic acid sequence, FIG. 2B-1 (SEQ ID NO:23) and amino acid sequence, FIG. 2B-2 (SEQ ID NO:24) of the W9 protein, a non-limiting, representative chimeric CDKi protein of the invention;

FIG. 4A is a representation of a line graph showing the ability of non-limiting, representative AV-CDKi's of the invention to inhibit proliferation of SW480 colon carcinoma cells. Shown is the percent inhibition of cell growth following transduction with adenovirus containing an entire E4 region and a CMV promoter operably linked to no insert (Null, circles), p16 (solid squares), p27 (triangles), W7 (hatched squares), and W9 (diamonds).

FIG. 6A is a representation of a line graph showing that a non-limiting, representative adenovirus of the invention, AV-W9, is more effective than AV-p16, AV-p27, or AV-W7 in inducing apoptosis in PC3 prostate tumor cells. Apoptosis was measured three days following transduction with the indicated AV-CDKi at equivalent MOI. Shown are the percentage of cells induced to undergo apoptosis following transduction by adenoviruses containing the entire E4 region (AV) and encoding p16 (solid squares), p27 (triangles), W7 (hatched squares), W9 (diamonds), or CMV promoter with no insert (Null, circles);

DESCRIPTION OF THE PREFERRED EMBODIMENTS

Figure 1:
FIG. 1 is a diagrammatic representation of a nucleic acid sequence encoding a secreted, internalizable form of a W9 protein, a non-limiting, representative chimeric CDKi of the invention. This sequence, when positioned for expression in a vector and introduced into a cell, will encode a protein that is secreted. The secreted protein is then internalized by another cell or by the cell in which it was expressed and secreted.

The patent and scientific literature referred to herein establishes knowledge that is available to those with skill in the art. The issued U.S. patents, allowed applications, published foreign applications, and references, including GenBank database sequences, that are cited herein are hereby incorporated by reference to the same extent as if each was specifically and individually indicated to be incorporated by reference.

The present invention provides compositions and methods for inhibiting the proliferation of, and inducing apoptosis in, neoplastic cells. By "neoplastic cell" is meant a cell that shows aberrant cell growth, such as increased cell growth. A neoplastic cell may be a hyperplastic cell, a cell that shows a lack of contact inhibition of growth in vitro, a tumor cell that is incapable of metastasis in vivo, or a cancer cell that is capable of metastasis in vivo.

The compositions and methods of the invention are based on the discovery that a chimeric CDKi protein (e.g., W9), when combined with an adenovirus E4 protein acts synergistically to induce apoptosis selectively in neoplastic cells, as well as to inhibit cell proliferation in these cells. Preferably, a chimeric CDKi protein, when combined with an adenovirus E4 protein or active fragment thereof, induces apoptosis in neoplastic cells at lower concentrations than concentrations required to induce apoptosis in non-neoplastic cells.

According to the invention, compositions are provided which include nucleic acids or proteins. The invention further provides methods for the in vitro and in vivo use of the compositions of the invention.

In one embodiment, the invention provides a nucleic acid composition consisting essentially of a first nucleic acid sequence encoding a chimeric cyclin dependent kinase inhibitor (chimeric CDKi) protein, and a second nucleic acid sequence encoding an adenovirus E4 protein.

In accordance with the invention, by "consisting essentially of" is meant that the indicated composition excludes ingredients that materially affect the characteristics of the composition. Thus, the composition of this embodiment of the invention does not, for example, comprise an adenovirus protein that materially affects the characteristics of the composition. An example of an adenovirus protein that materially affects the characteristics of the composition is the adenovirus E1 protein. A "nucleic acid" refers to single-stranded or double-stranded polynucleotides, such as deoxyribonucleic acid (DNA), ribonucleic acid (RNA), or analogs of either DNA or RNA. The first and second nucleic acid sequences are operably linked to regulatory sequences to ensure their transcription and translation into chimeric CDKi protein and adenovirus E4 protein, respectively, in a cell introduced with these nucleic acid sequences.

By "introduction" is meant the introduction of exogenous nucleic acid into a cell by any means, including, without limitation, transfection, transduction, infection, and tranformation. By the term "transfection" is meant the introduction of exogenous nucleic acid into a cell by physical means. As used herein, by "transduction" is meant the introduction of exogenous nucleic acid into a cell using a viral particle, preferably a genetically modified (i.e., recombinant) viral particle. For various techniques for manipulating mammalian cells, see Keown et al. (1990) *Methods of Enzymology* 185: 527–537.

As used herein, by "operably linked" is meant that a nucleic acid sequence encoding a polypeptide and transcriptional regulatory sequences are connected in such a way as to permit expression of the nucleic acid sequence when introduced into a cell. By "regulatory sequence" is meant nucleic acid sequences, such as initiation signals, IRES sequences, polyadenylation (polyA) signals, promoters, and enhancers which control cellular expression of protein coding sequences with which they are operably linked. By "expression" of a nucleic acid sequence encoding a protein or polypeptide fragment is meant expression in a cell of that nucleic acid as mRNA and production of that protein or polypeptide fragment.

The first and second nucleic acid sequences may be on a viral vector used to make a recombinant infectious virus particle. Useful recombinant infectious viruses include, without limitation, adenovirus, adenovirus lacking an entire E4 region, lentivirus, retrovirus, adeno-associated virus, herpesvirus, vaccinia virus, and RNA virus. The first and second nucleic acid sequences of the invention may also be on plasmids, such as an Epstein-Barr virus-based plasmid. The nucleic acid sequences of the invention may alternatively be combined with a non-nucleic acid delivery system, such as a liposome.

The nucleic acid sequences are operably linked to regulatory sequences such that they are positioned for expression. The nucleic acid sequences may then be incorporated into a plasmid, which is internalized by a cell. The nucleic acid sequences operably linked to regulatory sequences may also be incorporated into a liposome, whose membrane can fuse with a cell such that the nucleic acid sequence is deposited into the cell's cytoplasm, and so internalized by the cell. The nucleic acid sequences internalized by a cell will then enter the nucleus, where they will be expressed as chimeric CDKi protein (such as W9) and adenovirus E4 proteins. Thus, by "positioned for expression" is meant that a nucleic acid sequence encoding a polypeptide is operably linked to a regulatory sequence (e.g., a promoter), such that the nucleic acid sequence is transcribed and translated in a cell to produce the polypeptide.

In an additional aspect the invention provides a nucleic acid composition comprising a first nucleic acid sequence encoding a secretable, internalizable form of a chimeric CDKi protein and a second nucleic acid sequence encoding a secretable, internalizable form of an adenovirus E4 protein, wherein the first and second nucleic acid sequences are operably linked to at least one regulatory sequence. By "secretable, internalizable form" is meant a form of a protein that is modified using standard molecular biology techniques such that it can be discharged or released by the cell which produces it and such that it can be taken up by a cell into the cell's cytoplasm and/or nucleus, where the protein can participate in intracellular functions.

In other aspects, the invention provides a protein composition is provided which includes a purified chimeric CDKi protein and a purified adenovirus E4 protein. Preferably, the chimeric CDKi protein and the purified adenovirus E4 protein are modified such that they can be taken up by a cell into the cell's cytoplasm and/or nucleus, where the proteins can participate in intracellular functions.

As used herein, by "purified" is meant a protein that has been separated from components which naturally accompany it or, in the case of a protein generated by recombinant biology techniques, components that accompany it in the modified cell or virus. Of course, those of ordinary skill in protein chemistry will understand that water, buffers, and other small molecules may additionally be present in a purified protein preparation. Typically, a purified protein is pure when it is at least 60%, by weight, free from other accompanying proteins and organic molecules (e.g., nucleic acid). Preferably, a purified protein is at least 75%, more preferably, at least 90%, even more preferably, at least 95%, and most preferably at least 99% by weight, free from accompanying proteins and organic molecules. Preferably, a purified protein of the invention is obtained by expression in a cell of a nucleic acid sequence encoding the protein. Purity can be measured by any appropriate method including, without limitation, column chromatography, polyacrylamide gel electrophoresis, and HPLC analysis.

The invention further provides compositions for use in treating or preventing neoplasia. These compositions comprise nucleic acid compositions or protein compositions according to the invention in combination with a pharmaceutically acceptable carrier. A "pharmaceutically acceptable carrier" includes, without limitation, any and all solvents, dispersion media, coatings, antibacterial and antifungal agents, isotonic and absorption-delaying agents, and agents which improve composition internalization by a cell which are non-toxic to the cell, and which do not reduce the therapeutic activity of the nucleic acid or protein. Except insofar as any conventional medium or agent is incompatible with the active ingredient, its use as a pharmaceutically acceptable carrier in the therapeutic compositions of the invention is contemplated.

The nucleic acid compositions and protein compositions described above find use in vitro, for example, in functional assays where apoptosis is used as a read-out. In another example, these compositions also find use in vitro in methods to synchronize the cell cycle of normal cultured cells.

In vivo, the compositions of the invention find use as anti-neoplasia therapeutics. For example, a composition containing the nucleic acid composition described above combined with a pharmaceutically acceptable carrier may be used in a gene therapy approach to inhibit the growth of neoplastic cells. The protein composition described above may also be combined with a pharmaceutically acceptable carrier and may be delivered to a tumor to inhibit its growth.

In yet another embodiment, the invention features a cell that contains nucleic acid sequences encoding secretable, internalizable W9 protein and adenovirus E4 protein, where these sequences are operably linked to regulatory sequences such that they will be expressed in the cell. This cell finds use as a vehicle to deliver paracrine-acting proteins of the invention to cells in vivo. Preferably, the cell is derived from the animal which is being treated with the proteins of the invention.

In accordance with the present invention, the compositions (and components thereof are described in detail -below. Additionally, methods are provided which can be used to prepare the compositions (and components thereof) of the invention.

I. Preparation of Components of the Compositions of the Invention

The compositions of the invention require as one component a chimeric CDki protein, or a nucleic acid sequence encoding a chimeric CDKi protein. As a second component, the compositions of the invention require an adenovirus E4 protein, or a nucleic acid sequence encoding an adenovirus E4 protein.

A. Chimeric CDKi Proteins

By "chimeric CDKi protein" is meant a fusion protein comprising at least an active fragment of a protein from the INK4 family of CDKi protein and at least an active fragment of a protein from the CIP/KIP family of CDKi proteins. A "fusion protein" of the invention is a single polypeptide chain that comprises at least a active fragment of a first protein and at least a active fragment of a second protein, wherein the two fragments are joined either directly or indirectly with a peptide bond.

Proteins from the CIP/KIP family of CDKi proteins include, without limitation, human $p27^{kip1}$ (GenBank Accession No. U10906, Polyak et al. (1994) Cell 78:56–66); murine $p27^{kip1}$ (GenBank Accession No. U09968, Polyak et al. (1994) Cell 78:56–66); rat $p27^{kip1}$ (GenBank Accession Nos. D86924 and D83792, Nomura et al. (1997) Gene 191(2):211–218); human $p57^{KIP2}$ (GenBank Accession No. NM_000076, Matsuoka et al. (1995) Genes Dev. 9(6):650–662); murine $p57^{KIP}2$ (GenBank Accession No. U20553, Lee et al. (1995) Genes Dev. 9(6):639–649); canine $p21^{Waf1/Cip1}$ (GenBank Accession No. AF076469); and human $p21^{Waf1/Cip1}$ (GenBank Accession No. L25610; Harper et al. (1993) Cell 75:806–816, 1993). The INK4 family of CDKi proteins which includes, without limitation, human $p18^{CDKN2C}$ (GenBank Accession Nos. AF041248 and NM_001262, Blais et al. (1998) Biochem. Biophys. Res. Commun. 247(1):146–153); human Cdi1 (GenBank Accession No. NM_005192, Gyuris et al. (1993) Cell 75(4):791–803); human $p19^{INK4d}$ (GenBank Accession No. NM_001800, Guan et al. (1996) Mol. Biol. Cell 7(1):57–70); human p15 (GenBank Accession No. S75756, Jen et al. (1994) Cancer Res. 54(24):6353–6358); murine $p15^{INK4b}$ (GenBank Accession Nos. U80415, U79634, and U79639); murine $p16^{Ink4/MTS1}$ (GenBank Accession Nos. AF044336 and AF044335, Zhang et al. (1998) Proc. Natl. Acad. Sci. USA 95(5):2429–2434); and human $p16^{INK4}$ (GenBank Accession No. NM_000077; Serrano et al. (1993) Nature 366(6456):704–707 and Okamoto et al. (1994) Proc. Natl. Acad. Sci. USA 91(23):11045–11049).

Exemplary chimeric CDKi proteins according to the invention are the fusion proteins described herein and described in PCT Publication No. WO99/06540, hereby incorporated by reference. Preferably, a chimeric CDKi is selected from one of the following proteins described below: W3, W4, W5, W6, W7, W8, W9, W10, or W11, as described below in Example I. Most preferably, the chimeric CDKi protein of the invention is W9.

As used herein, by "active fragment" is meant a polypeptide that encompasses at least the amino acid sequence required for inhibition of the appropriate cyclin dependent kinase which is targeted by the indicated CDKi (e.g., for human p27, see, Russo et. al. (1998) Nature 395:237–243). In a preferred embodiment, the chimeric cyclin dependent kinase inhibitor is derived from a mammal (eg., a human).

As used herein, by "W9 protein" is meant the W9 protein which consists of an N-terminal portion containing the CDK inhibitory domain (amino acid residues 25–93) of human p27 covalently linked via a peptide bond to a C-terminal portion containing the entire human p16 (INK4) protein, as well as any equivalent protein that has either an activity equivalent to the W9 protein or has an amino acid sequence having at least one conservative amino acid substitution when compared to the amino acid sequence of the W9 protein. The W9 protein preferably has the amino acid sequence provided in FIG. 2B. The nucleic acid sequence and amino acid sequence of W9 (without the HA tag and six histidine residues) are provided in SEQ ID NOs: 23 and 24, respectively.

In the presence of an adenovirus E4 protein, a chimeric CDKi protein induces an arrest in cell proliferation in neoplastic cells, and induces neoplastic cells to apoptose. Preferably, in the presence of an adenovirus E4 protein, a chimeric CDKi protein kills neoplastic cells, but does not kill non-neoplastic cells.

The nucleic acid sequence and amino acid sequence of the chimeric CDKi proteins of the invention are provided in the Examples below. However, given the degenerative nature of the genetic code, any nucleic acid sequence encoding a chimeric CDKi protein is within the definition of a chimeric CDKi-encoding nudeic acid sequence. Nudeic acid sequences encoding a chimeric CDKi protein can also be made from the nucleic acid and amino acid sequences and descriptions provided herein according to standard techniques. The nudeic acid and amino acid sequence of, for example, human p27, is available as GenBank Accession No. U10906 (Polyak et al. (1994) *Cell* 78: 56–66). The nucleic acid and amino acid sequence of human p16 is available as GenBank Accession No. L27211 (Serrano et al. (1993) *Nature* 366: 704–707; Okamoto et al., (1994) *Proc. Natl. Acad. Sci. USA* 91: 11045–11049). Techniques to make a chimeric CDKi protein-encoding nucleic acid sequence include, without limitation, amplification by PCR of the nucleic acid sequences encoding a member of the CIP/KIP family of CDKi's and amplification by PCR of the nucleic acid sequences encoding a member of the INK4 family of CDKi's, identification of cDNA clones containing CDKi-encoding nudeic acid sequences using probes generated from the sequences provided herein followed by appropriate in-frame ligation, and PCR to generate the chimeric CDKi-encoding nucleic acid sequences using overlapping oligo-nucleotides. All of these techniques are well known (see, for example, Ausubel et al. (1994) *Current Protocols in Molecular Biology*, John Wiley & Sons, New York, N.Y.).

A chimeric CDKi protein may be made by any standard method well-known to one with skill in the art. Preferably, the chimeric CDKi protein is purified. Purified chimeric CDKi protein may be produced by chemical synthesis (see, e.g., *Solid Phase Synthesis*, 2nd ed. (1984) The Pierce Chemical Co., Rockford, Ill.). The chimeric CDKi protein can be made by subcloning a chimeric CDKi-encoding sequence into an expression plasmid, transfecting that plasmid into an appropriate cell, and purifying the synthesized chimeric CDKi protein from the cell using anti-p27 or anti-p16 antibodies. Alternative methods for protein purification include high performance liquid chromatography (HPLC; see, e.g., Fisher (1980) *Laboratory Techniques in Biochemistry and Molecular Biology*, Work and Burdon (eds.), Elsevier).

Chimeric CDKi proteins can be synthesized in any appropriate cell type including bacteria, insect, or mammalian, by recombinant techniques well known to those with skill in the art. For example, a chimeric CDKi-encoding nucleic acid sequence can be inserted into a baculovirus vector such that it is positioned for expression in the vector. The vector may then be used to generate recombinant baculovirus particles. Insect cells (e.g., Sf9 cells) transduced with the recombinant baculovirus will express the chimeric CDKi protein. Following lysis, the chimeric CDKi protein can be purified. Where the chimeric CDKi-encoding nudeic acid sequence has been modified using standard molecular biology techniques to encode a secreted protein (see below), the secreted chimeric CDKi protein can be isolated from the conditioned growth media of the transduced insect cells and purified.

"Chimeric CDKi protein," in accordance with the present invention, additionally encompasses all equivalents of a chimeric CDKi protein. A chimeric CDKi protein equivalent has an activity equivalent to that of the chimeric CDKi protein of which it is an equivalent or has an amino acid sequence having at least one conservative amino acid substitution when compared to the amino acid sequence of the chimeric CDKi protein of which it is an equivalent. Such conservative substitutions typically include substitutions within the following groups: glycine, alanine, valine, isoleucine, leucine; aspartic add, glutamic acid, asparagine, glutamine; serine, threonine; lysine, arginine; and phenylalanine, tyrosine.

A chimeric CDKi protein equivalent may be a fusion protein of a CDK inhibitory domain bonded to an INK4 family member CDKi (eg., p16). By "CDK inhibitory domain" is meant a domain of a CIP/KIP family member cyclin-dependent kinase inhibitor that contacts both the kinase and the cyclin binding subunit and is sufficient for kinase inhibition. Preferably, the CDK inhibitory domain lacks the nuclear localization signal and the QT domain. One or both of the CDK inhibitory domain and INK4 may be from a mammal, and preferably both are derived from the mammal that is being treated (e.g., a mouse is treated with a chimeric CDKi protein equivalent consisting of murine protein sequences). Where the chimeric CDKi protein is W9, preferably, a W9 protein equivalent contains at its N-terminal portion the CDK inhibitory domain and at its C-terminal portion the INK4 family member protein, or a fragment thereof.

Nucleic acid sequences encoding chimeric CDKi protein equivalents can be made by standard techniques including the in-frame ligation of known nucleic acid sequences encoding the CDK inhibitory domains of the various CIP/KIP family member CDKi's with the nucleic acid sequences encoding the INK4 proteins. The nucleic acid sequences encoding the human versions of these proteins is known (e.g., human p15, GenBank Accession No. S757756; human p16, GenBank Accession No.27211; human p18, GenBank Accession No. AF041248; human p19, GenBank Accession No. U20498; human p21, GenBank Accession No. L47232; human p27, GenBank Accession No. U10906).

Where a chimeric CDKi protein equivalent consists of non-human protein sequences, nucleic acid sequences encoding a chimeric CDKi protein equivalent can be made by using gene sequences from non-human animals. For example, a chimeric CDKi protein equivalent may consist of a CDK inhibitory domain from a murine CIP/KIP family member fused to full length murine p16. Transfection of these sequences into a cell, where the sequences are positioned for expression in that cell, allow for the production and purification of the encoded chimeric CDKi protein equivalent.

In addition, a chimeric CDKi protein equivalent of the invention can be made by fusing proteins, or fragments thereof (or encoding nucleic acids), from two different species (e.g., a murine p27 CDK inhibitory domain joined to a human p16). Preferably, the chimeric CDKi protein equivalent used to treat an animal will be derived from proteins from that animal. For example, a nucleic acid sequence encoding a canine chimeric CDKi protein equivalent made by fusing a nucleic acid sequence encoding canine CDK inhibitory domain to a nucleic acid sequence encoding a canine p16 molecule. This nucleic acid sequence, when expressed in a cell, generates a chimeric CDKi protein equivalent that may be used, for example, to treat a neoplasia in a domestic dog.

A chimeric CDKi protein equivalent may also be synthetic. In addition, the CDK inhibitory domain may be joined to the INK4 family member protein via a covalent peptide bond or a chemical crosslinker.

Preferably, the chimeric CDKi protein equivalent is a fusion protein of the CDK inhibitory domain of a p27 protein and a p16 protein or fragment thereof. More preferably, the chimeric CDKi protein equivalent (or encoding nucleic acid), when administered in the presence of an adenovirus E4 protein, has an anti-neoplastic activity that is comparable to that of the chimeric CDKi protein (or of the chimeric CDKi protein-encoding nucleic acid) to which it is equivalent administered under the same conditions (for example, a W9 protein equivalent has an anti-neoplastic activity comparable to that of W9 protein). Most preferably, a chimeric CDKi protein equivalent will, when combined with an adenovirus E4 protein or active fragment thereof, induce apoptosis in neoplastic cells at lower concentrations than concentrations required to induce apoptosis in nonneoplastic cells. Apoptosis may be readily assessed by, for example, staining the cells with Annexin and/or propidium iodide (PI), or by using the Tdt TUNEL assay. These apoptosis assays are well known (see, for example, Kishimoto et al. (1995) *J. Exp. Med.* 181: 649–655; Pepper et al. (1998) *Leuk Res.* 22(5):43944; and Walsh et al., (1998) *J. Immunol. Methods* 217(1–2):153–63).

B. Adenovirus E4 Protein

As used herein, the term "adenovirus E4 protein" encompasses at least one protein encoded by the E4 region of adenovirus, or an active fragment of an adenovirus E4 protein, or an equivalent of an adenovirus E4 protein. There are at least six different open reading frames (orfs) in the E4 region of adenovirus, of which there are at least 42 serotypes. Hence, an adenovirus E4 protein may be any one or more but not all of the adenovirus E4 orf proteins from any serotype of adenovirus. An active fragment of an adenovirus E4 protein is a fragment of an adenovirus E4 protein that, when administered with a W9 protein, provides an anti-neoplastic activity that is greater than the anti-neoplastic activity of a chimeric CDKi protein protein administered alone. An equivalent of an adenovirus E4 protein or active fragment thereof is meant a chemical (for example, without limitation, a protein, lipid, or carbohydrate) that, when administered with a W9 protein, provides an anti-neoplastic activity comparable to that provided by an adenovirus E4 protein or an active fragment of an adenovirus E4 protein.

One exemplary adenovirus E4 protein is the E4orf6 protein encoded by adenovirus E4orf6. A second exemplary adenovirus E4 protein is the E4orf3 protein encoded by adenovirus E4orf3. The adenovirus E4 protein may be from any serotype of adenovirus and may be from an adenovirus isolated from any species of animal (eg., human, bovine, avian).

The sequences of the E4 region of various adenovirus serotypes are publicly available, for example, from the GenBank database, and include, without limitation, GenBank Accession Nos. J01966, J01980, K02368, X02998, and Y09598 (type 5); AF030154 and AF083132 (type 3); L19443 (type 40); Y09598 (avian EDS); X73487 and X51800 (type 12); U77082 and J01917 (type 2); S82508 (type 9); AF108105 (type 17); and Y07760 and U55001 (type 1), each of which is hereby incorporated by reference. These adenovirus E4 region-containing sequences can be inserted with the E4 promoter into a vector or plasmid of choice (eg., adenovirus transfer vector lacking the entire E4 region). Alternatively, adenovirus E4 region-containing sequences can be inserted in a vector or plasmid of choice operably linked to an exogenous promoter, such as a constitutively active promoter (eg., CMV or SV40 early), or an inducible promoter (e.g., the MMTV promoter).

Nucleic acid sequences containing at least part of the E4 region of adenovirus can be introduced into a cell to generate E4 proteins. Since over-expression of the adenovirus E4 proteins is often toxic to the cell, it may be desirable to operably link adenovirus E4 region-containing nudeic acid sequences to an inducible promoter prior to transfection into a cell.

Any cell type may be used to express the adenovirus E4 proteins; however, preferably, the cell chosen is one in which the adenovirus E4 proteins may be appropriately folded and post-translationally modified.

Adenovirus E4 proteins produced by recombinant methods may be purified according to standard methods (eg., HPLC).

Various methods may be employed to identify active fragments and/or equivalents of the adenovirus E4orf6 protein, or other E4 orf proteins, that are sufficient to synergize with a chimeric CDKi protein to induce apoptosis in neoplastic cells. By "an active fragment of an adenovirus E4 protein" is meant a fragment of an adenovirus E4 protein that, when administered with a chimeric CDKi protein, provides an anti-neoplastic activity that is greater than the anti-neoplastic activity of a chimeric CDKi protein administered alone. Preferably, the active fragment of an adenovirus E4 protein is purified.

Deletional analysis may be employed to identify an adenovirus E4 protein, or active fragment thereof, capable of synergizing with a specific chimeric CDKi protein (e.g., W9) to induce apoptosis in neoplastic cells. In a non-limiting method, recombinant adenovirus encoding a specific chimeric CDKi protein may be modified such that portions of the E4 region are deleted. In this way, not all of the E4 orf proteins are produced and the deleted E4 orf protein may be identified by deletional mapping. For example, one recombinant adenovirus encoding a chimeric CDKi protein encodes only the E4orf6 protein, and none of the other E4orf proteins. Another recombinant adenovirus encoding a chimeric CDKi protein encodes only the E4orf3 and E4orf6 proteins, but does not encode any of the other E4orf proteins. Yet another recombinant adenovirus encoding a chimeric CDKi protein encodes only a fragment of E4orf6, and none of the other E4orf proteins. The E4orf6 fragment of this virus contains, of course, an ATG and a stop sequence, and produces a polypeptide fragment.

To determine which portions(s) of the E4 region are required for apoptosis in neoplastic cells, the different recombinant adenoviruses encoding a specific chimeric CDKi protein (e.g., W9) and the various fragments of E4 region proteins are titered, and the same MOI unit of each recombinant adenovirus is used to transduce a variety of normal and neoplastic cells, as described below in Examples IV and VI. The ability of these recombinant adenoviruses to induce apoptosis in neoplastic cells is compared to the adenovirus encoding W9 protein and containing the entire E4 region (AV-W9) described below in Example III. Thus, where a recombinant adenovirus encoding the specific chimeric CDKi protein (e.g., W9) and fewer than all of the E4 orf proteins (or fragments thereof) is sufficient to induce apoptosis in neoplastic cells, the E4 or proteins (or fragments thereof) encoded by that recombinant adenovirus identifies those E4 proteins (or active fragments thereof) that are sufficient to synergize with that specific chimeric CDKi protein (in this case W9) to selectively induce apoptosis in neoplastic cells.

In an alternate method to identify an adenovirus E4 protein, or active fragment thereof, required to enhance the apoptosis-inducing ability of a chimeric CDKi protein, an overlapping peptide library derived from all of the adenovirus E4 orf proteins may be produced. Pools of library members are then introduced into a normal or neoplastic cell expressing the chimeric CDKi protein to determine if a peptide within the pool induced apoptosis in that cell. Where apoptosis is induced, the pool is subdivided, such that eventually the peptide or peptides that are able to act synergistically with that specific CDKi protein to induce apoptosis in a cell are identified.

It will be understood that a polypeptide or chemical having an ability to synergize with a chimeric CDKi protein to produce the anti-neoplastic compositions of the invention need not be derived from an adenovirus. An equivalent of an adenovirus E4 protein, or active fragment thereof, may be a protein, lipid, or carbohydrate from another virus, from any type of cell (e.g., bacterial, insect, avian, mammalian), from a fungus, or may be a synthetic chemical.

For example, to identify an adenovirus E4 protein (or active fragment thereof) equivalent, a nucleic acid sequence encoding a chimeric CDKi protein and not encoding an adenovirus E4 protein is transfected into a neoplastic cell, such that the nucleic acid sequence is positioned for expression in the cell. Preferably, the nucleic acid sequence encoding the chimeric CDKi protein is stably transfected into the neoplastic cell. Pools of compounds thought to contain an adenovirus E4 protein (or active fragment) equivalent are then administered to the transfected neoplastic cell. A pool of compounds that induces apoptosis in the transfected neoplastic cell is subdivided, and the subdivided pools administered to transfected neoplastic cells until a purified compound (or mixture) able to induce the chimeric CDKi protein-transfected neoplastic cells to apoptose is identified.

As positive controls, nucleic acid sequences comprising the entire adenovirus E4 region, an adenovirus E4 protein, or an active fragment of an adenovirus E4 protein, are transfected into the chimeric CDKi protein-expressing cell, such that these sequences are positioned for expression in the cell. A compound that induces a chimeric CDKi protein-expressing neoplastic cell to undergo apoptosis at a rate comparable to that observed with chimeric CDKi protein-expressing cells transfected with nucleic acid sequences comprising the entire adenovirus E4 region, an adenovirus E4 protein, or an active fragment of an adenovirus E4 protein, is an equivalent of an adenovirus E4 protein.

II. Preparation of Protein Compositions of the Invention

A chimeric CDKi protein and an adenovirus E4 protein may be generated in vitro, purified, and administered either systemically or locally to the affected area (e.g., administered directly into the tumor). Preferably, the chimeric CDKi protein and the adenovirus E4 protein contain translocation sequences such that they are internalizable. An "internalizable" form of a protein is modified such that it will be internalized by a cell (e.g., modified to contain a translocation sequence), as described above in the first aspect of the invention.

For example, nucleic acid encoding an internalizable form of a chimeric CDKi protein may be transfected into a prokaryotic or eukaryotic cell in vitro, such that the protein is positioned for expression in that cell. The protein may also be secreted (i.e., a secretable), in which case it may be purified from the conditioned culture media of the transfected cell. Alternatively, if the internalizable form of the protein is not secreted, but is, rather, an internal protein, in which case the transfected cell is first lysed to release the internalizable chimeric CDKi protein, which can then be purified according to standard methods. Recombinant virus encoding a chimeric CDKi protein (e.g., encoding a internalizable form of a chimeric CDKi) may also be used to transduce eukaryotic cells. The chimeric CDKi protein may then be purified from the transduced cell either from the conditioned culture media (for secreted protein) or by lysis of the cell (for non-secreted protein). As described herein, the nucleic acid sequence encoding a chimeric CDKi protein may be readily modified through the attachment of a signal sequence to the protein-encoding sequences to encode a secretable chimeric CDKi protein. Likewise, the nucleic acid sequence encoding a chimeric CDKi protein may be modified through the attachment of a translocation sequence to the protein-encoding sequences to encode an internalizable chimeric CDKi protein.

An adenovirus E4 protein may be similarly expressed in vitro by the same cell that expresses the chimeric CDKi protein or by a different cell. The cell expressing the adenovirus E4 protein and the cell expressing the chimeric CDKi protein need not be the same type of cell. For example, the adenovirus E4 protein may be expressed by and purified from a bacterial cell, and the chimeric CDKi protein may be expressed by and purified from an insect cell.

It will be understood that the components of the protein compositions of the invention (e.g., chimeric CDKi and adenovirus E4 proteins) may be completely synthetic and produced on a peptide synthesizer. For example, if a small adenovirus E4 protein, or an active fragment thereof, is found to complement the anti-neoplastic effects of a chimeric CDKi protein, such a small protein or polypeptide fragment may be chemically synthesized by a peptide synthesizer.

Purified protein compositions of the invention may be administered to target cells in vitro or in vivo by any suitable method. For example, compositions that comprise internalizable proteins may be diluted in culture media and added to cells cultured in vitro. Similarly, for in vivo delivery, compositions comprising internalizable proteins may be combined with a pharmaceutically acceptable carrier, such as buffered saline (see below), and administered (eg., to the site of the tumor) by injection with a syringe or catheter.

For the delivery of protein compositions comprising proteins lacking translocation sequences such that they will not be internalized by target cells, the composition is preferably first combined with a delivery system that will facilitate the internalization of the composition by cells. For example, the composition may first be packaged in a liposome that bears a surface positive charge. Upon delivery to a cell either in vitro or in vivo, the liposome will fuse with the cell membrane and deposit the protein composition contained within the liposome into the cytoplasm of the cell.

III. Preparation of Nucleic Acid Compositions of the Invention

The invention provides a nucleic acid composition comprising a nucleic acid sequence encoding a chimeric CDKi protein and a second nucleic acid sequence encoding an adenovirus E4 protein.

A. Virus Based Nucleic Acid Compositions

The nucleic acid sequences encoding a chimeric CDKi protein may be incorporated into a viral vector that can be used to generate recombinant virus partides (such as an adenovirus) that contains at least part of the adenovirus E4 region and encodes a chimeric CDKi protein and at least one adenovirus E4 protein (eg., E4orf6).

Where the virus is a recombinant adenovirus, the adenovirus may be of any serotype. Preferably, the adenovirus lacks the entire E4 region such that not all of the E4 orf proteins are encoded by the adenovirus. The chimeric CDKi protein-encoding sequences may be inserted into one of the regions of the adenovirus genome whose removal is not lethal. One known region of the adenovirus genome that may be non-lethally removed is the E1 region, which controls adenovirus replication. Into this region may be inserted promoter and/or enhancer sequences using standard molecular biology techniques (see, for example, Ausubel et al. (1994) *Current Protocols in Molecular Biology* John Wiley & Sons, New York, N.Y.). Such promoter/enhancer sequences may be constitutively active (e.g., the CMV promoter or the EF1α promoter), cell-type specific (e.g., the SM22α gene promoter that is specifically expressed in smooth muscle cells), or inducible (e.g., the cytokine-stimulated inducible nitric oxide synthase (iNOS) gene promoter). Numerous promoter/enhancer sequences are well known and their sequences available, for example, in the GenBank database (National Center for Biotechnology Information, National Institutes of Health, Bethesda, Md.). The inserted promoter (eg., the CMV promoter) may then be operably linked to the nucleic acid sequence encoding a chimeric CDKi protein and to a poly A signal sequence (from, e.g., SV40 virus) to create a transgene. By "transgene" is meant a nudeic acid sequence encoding a desired protein or polypeptide fragment operably linked to regulatory sequences such that the nudeic add sequence is transcribed and translated when the transgene is introduced into a cell. Transgenes typically comprise a promoter/enhancer::protein-encoding nucleic acid sequence::polyA signal. A polycistronic transgene comprising two protein encoding nucleic acid sequences separated by an IRES sequence is also within this definition; consequently an IRES is also a "regulatory sequence" as used herein.

In an embodiment in which the delivery virus is a recombinant adenovirus, while the transgene may be inserted into the E1 region of an adenovirus vector containing at least part of the E4 region, it will be understood that the transgene may be inserted at any non-lethal position in the adenovirus genome to encode for a chimeric CDKi protein and at least one adenovirus E4 protein or active fragment thereof (e.g., the chimeric CDKi protein-encoding transgene may be inserted into the E3 region). One non-limiting way to make a recombinant adenovirus encoding a chimeric CDKi protein and an adenovirus E4 protein is to insert a chimeric CDKi protein-encoding transgene comprising a chimeric CDKi protein-encoding nucleic acid sequence operably linked to a CMV promoter/enhancer and an SV40 poly A signal and an adenovirus E4 protein-encoding transgene comprising an adenovirus E4 protein-encoding nucleic acid sequence operably linked to a CMV promoter/enhancer and an SV40 poly A signal into the E1 region of a recombinant replication-deficient adenovirus type 5 (Ad5) vector lacking both the E1 and E4 regions. The recombinant retrovirus vector containing transgenes encoding a chimeric CDKi protein and an adenovirus E4 protein is then packaged in 293 cells to produce infectious recombinant adenovirus particles.

The recombinant adenoviruses encoding a chimeric CDKi protein and at least one E4 protein may be used to transduce cells in vivo or in vitro. Such administration may be standardized by determining the multiplicity of infection (MOI) of the recombinant adenovirus, or by determining the actual number of viral particles based on the amount of viral DNA. Such standardization of viral particles is routine and is generally described in Phillipson et al. (1975) *Molecular Biology of Adenoviruses*, Virology Monograph, Springer Verlag, New York.

In another embodiment, the virus which does not contain any adenovirus sequences. For example, if the virus is a lentivirus, viral vectors that are used to generate recombinant lentivirus may be genetically modified to contain nucleic acid sequences encoding a chimeric CDKi protein and at least one adenovirus E4 region-encoded protein (eg., E4orf6). The use of recombinant lentivirus as gene therapy delivery vehicles is well known in the art (see, e.g., Dull et al. (1998) *J. Virol.* 72: 8463–8471). One or both of the inserted nucleic acid sequences may be operably linked to exogenous promoter/enhancer and polyA signal sequences (e.g., the E4 region promoter or the CMV promoter). Alternatively, the nucleic acid sequences can be inserted such that their expression is directed by a lentivirus promoter and polyA signal. A standard lentivirus transfer vector has a capacity of 7 kB. Thus, to generate a recombinant lentivirus encoding both a chimeric CDKi protein and an adenovirus E4 protein, both nucleic acid sequences (i.e., the sequence encoding a chimeric CDKi protein and the sequence encoding an adenovirus E4 protein) can be separated by an IRES sequence (Jang and Wimmer (1990) *Genes & Dev.* 4: 1560–1572) such that a polycistronic mRNA encoding both proteins (i.e., chimeric CDKi protein and adenovirus E4 protein) may be generated by the same lentivirus or exogenous promoter/enhancer. Such a polycistronic mRNA will reduce the size of the inserted transgene (i.e., the inserted nudeic acid sequence containing a promoter/enhancer and polyA signal operably linked to a chimeric CDKi protein-encoding nucleic acid sequence and an adenovirus E4 protein-encoding nucleic acid sequence). Following appropriate packaging and titering, infectious recombinant lentivirus encoding at least one adenovirus E4 protein and a chimeric CDKi protein may be used to transduce cells. The anti-neoplastic efficacy of the chimeric CDKi protein paired with an adenovirus E4 protein may be tested in in vivo or in in vitro model systems.

Where the virus lacking any adenovirus sequences is an adeno-associated virus (AAV), standard recombinant DNA techniques may be employed to generate recombinant AAV encoding an adenovirus E4 protein and a chimeric CDKi protein (such as W9). Recombinant AAV can be made by transfecting a producer cell with two trans-complementing plasmids, one plasmid encoding the rep and cap proteins, and the other plasmid encoding the transgene with the AAV inverted terminal repeat (ITR) sequences. The transfected producer cell line then produces recombinant AAV infectious viral particles, which can be used to transduce cells. The transgene size capacity of an AAV transgene-ITR plasmid is typically approximately 4.5 kB. The preferred chimeric CDKi protein of the invention, W9, is encoded by a nucleic sequence that is less than 0.7 kB. Thus, a transgene encompassing, for example, a CMV promoter/enhancer::W9-encoding nucleic acid sequence::IRES sequence::adenovirus E4 protein-encoding nucleic acid sequence::SV40 polyA signal may be readily accommodated by a standard AAV transgene-ITR plasmid and may be used to generate recombinant AAV partides encoding both an adenovirus E4 protein and W9 protein.

Where the virus lacking any adenovirus sequences is a standard retrovirus, such as a Moloney murine leukemia virus (MMLV), recombinant MMLV encoding a chimeric CDKi protein and an adenovirus E4 protein may be generated. In a standard MMLV transfer vector, such as the rkat43.3 vector (Finer et al. (1994) *Blood* 83: 43–50), the transgene(s) are inserted between the gag-encoding region and the 3' LTR. A standard MMLV transfer vector has a 7 kB transgene(s) capacity.

Other types of viruses that may be used to package and deliver the nudeic acid compositions of the invention include, without limitation, vaccinia virus, herpes virus, and various RNA based viruses. Because recombinant viruses are used to facilitate the internalization of the nucleic acids they carry by a transduced cell, these recombinant viruses are referred to as delivery systems.

In all of the above methods for packaging the nucleic acid compositions of the invention in recombinant viruses, infectious viral particles are harvested from packaging cell lines (or the medium in which these cells are cultured) transfected with viral vectors modified to contain the nucleic acid sequences encoding W9 and an adenovirus E4 protein. First, the nucleic acid sequences encoding a chimeric CDKi protein (such as W9) and an adenovirus E4 protein are inserted into the viral vector in such a manner as to be positioned for expression in the viral vector. An appropriate packaging cell is then transfected with the viral vector. The transfected packaging cell then produces infectious recombinant viral particles carrying the inserted nucleic acid sequences. The infectious viral particles may be purified from the conditioned medium in which the transfected packaging cells are cultured. Alternatively, the infectious recombinant viral particles may be purified by lysing the cells, generally with repeated rapid freeze/thaw cycles, and centrifugation to remove the cellular debris. Following separation from cellular debris, viral particles are isolated, titered according to standard methods (Phillipson et al., supra; Synder et al., (1996) *Current Protocols in Human Genetics*, John Wiley & Sons, New York, N.Y.), and stored at minus 70° C. To use, the viral particles are thawed, diluted (if appropriate) with a pharmaceutically acceptable carrier (e.g., buffered saline), and administered.

B. Non-Virus Based Nucleic Acid Compositions

In another embodiment, a nucleic acid composition of the invention may feature a non-virus vector, such as a plasmid comprising chimeric CDKi protein-encoding nucleic acid sequences and the adenovirus E4 protein-encoding nudeic acid sequences. Here, the delivered sequences are positioned for expression in the plasmid such that they will be expressed in a cell transfected with the plasmid. In one non-imiting example, the non-virus vector is an Epstein Barr Virus (EBV) based plasmid. If the EBV-based plasmid also contains the EBV origin of replication (oriP) and encodes the EBV nuclear protein, EBNA-1, the resulting plasmid will be capable of autonomous replication within a transfected cell. Such autonomous replication-capability will serve to enhance the amount of chimeric CDKi protein and adenovirus E4 protein expressed by a cell transfected with the EBV plasmid.

If desired, a transgene(s) encoding the chimeric CDKi protein and an adenovirus E4 protein may be separated from other plasmid sequences and administered. For example, the transgenes may be modified to be flanked with the recognition sites of a rare-cutting restriction endonuclease. Following digestion with the rare-cutting endonuclease, the transgene(s) encoding a chimeric CDKi protein and an adenovirus E4 protein may be separated from the remaining plasmid sequences by electrophoretic separation on an agarose gel, purified according to standard techniques, and delivered to a neoplastic cell to induce apoptosis.

In the above methods to deliver the nudeic acid compositions of the invention in non-virus plasmids or on transgene(s), the plasmid or transgene is preferably combined with a delivery system to facilitate its internalization by a neoplastic cell. Preferably, the delivery system will rely on the endocytic pathways for the internalization of the nucleic acid composition by the target cell. Exemplary delivery systems include liposomal-derived systems, polylysine conjugates, and artificial viral envelopes.

The nucleic acid compositions of the invention may be delivered to cells or tissues via a number of different delivery systems. Such systems are generally described in PCT Publication No. WO99/06540 (herein incorporated by reference).

In one preferred, non-limiting example, a transgene consisting of: CMVpromoter/enhancer::W9-encoding nucleic acid sequence::IRES::adenovirus E4orf6-encoding nucleic acid sequence::SV40 polyA signal is entrapped in a liposome bearing positive charges on its surface (e.g., lipofectins). Such a liposome containing a nucleic acid composition of the invention may also be tagged with antibodies that specifically find a cell surface antigen of the target tissue. For example, where a B cell lymphoma is known to express a B cell receptor having a certain idiotype, a liposome may be coated with anti-idiotype antibodies, enabling the antibody-coated liposome to bind to cells of the B cell lymphoma, and, thus, be internalized.

C. Nucleic Acid Compositions for Paracrine Delivery

The virus vectors and non-viral plasmids encoding a chimeric CDKi protein and an adenovirus E4 protein may be used to introduce virus or plasmid sequences into cells, such that the cells express and secrete chimeric CDKi and adenovirus E4 proteins which act in a paracrine fashion by being internalized by surrounding cells. By "paracrine" is meant action by a protein on a cell in which that protein was not synthesized.

For example, using a virus-based gene therapy approach, a recombinant virus may be modified to encode two different forms of a chimeric CDKi protein and an adenovirus E4 protein.

In one form, the chimeric CDKi protein and adenovirus E4 protein lack sequences enabling their secretion by the cell. These proteins, therefore, act in an autocrine fashion in the cell in which they are generated. By "autocrine" is meant action by a protein on a cell in which that protein was synthesized.

In a second form, both the chimeric CDKi protein and the adenovirus E4 protein are modified to contain a leader (secretion) sequence directing their localization to the endoplasmic reticulum, Golgi apparatus, and eventual secretion from the cell. The leader sequence can be any leader sequence from any nucleic acid sequence encoding a secreted protein. In addition, these secreted forms of the chimeric CDKi protein and adenovirus E4 proteins require translocation sequences that facilitate the translocation of the proteins across the cell membrane of a second cell, allowing the proteins to be internalized by that cell. These proteins are called "secretable, internalizable forms" of the proteins. Such translocation sequences sufficient to direct protein internalization are known and indude portion of the Drosophila antepennepedia protein (GenBank Accession No. E01911; Asato et al. (1989) Japanese Patent No. 1989085092-A1; Derossi et al. (1996) *J. Biol. Chem.* 271: 18188–18193; Derossi et al. (1994) *J. Biol. Chem.* 269:

10444–10450; Perez et al. (1992) *J. Cell. Sci.* 102: 717–722) the HIV transactivator (TAT) protein (Kuppuswamy et al. (1989) *Nucl. Acids Res.* 17:3551–3561; Frankel and Pabo (1989) *Cell* 55: 1189–1193; Green and Lowenstein (1989) *Cell* 55: 1179–1188), and mastoparan (Higashijima et al. (1990) *J. Biol. Chem.* 265: 14176–141860). Preferably, the translocation sequence is the sequence encoding amino acids 48–60 or amino acids 47–72 of the full length HIV tat protein.

FIG. 1 is a schematic diagram showing a non-limiting example of a paracrine-acting W9 encoding nucleic acid sequence. The W9-encoding nucleic acid sequence of FIG. 1 is modified to have a leader (secretion) sequence from any source and a translocation sequence from the HIV tat sequence. The leader sequence allows the encoded W9 protein to be secreted, while the HIV tat translocation sequence allows the internalization of the W9 protein by a neighboring cell and, further, guides the W9 protein into the nucleus of the cell.

In one embodiment, the secretable, internalizable form of a chimeric CDKi protein or the secretable, internalizable form of an adenovirus E4 proteins of the invention has the following sequence: N terminus-(Leader peptide) bonded to (HIV tat amino acids 1–72 peptide) bonded to (chimeric CDKi protein or adenovirus E4 protein)-C terminus. In yet additional embodiments, where the secretable, internalizable form of a CDKi protein or an adenovirus E4 protein of the invention has a signal (leader) sequence from proinsulin, and a translocation sequence from HIV tat amino acids 1–72. For example, a secretable, internalizable form of a W9 protein having a signal (leader) sequence from proinsulin, and a translocation sequence from HIV tat amino acids 1–72 has the nudeic acid sequence provided in SEQ ID NO:29, and the amino acid sequence provided in SEQ ID NO:30.

In addition, the signal peptide and translocation sequences may be separated from a chimeric CDKi protein or an adenovirus E4 protein with a linker, such as a $(Gly_4Ser)_3$ linker. In the case of a secretable, internalizable form of a W9 protein, where the linker is the $(Gly_4Ser)_3$ linker, the translocation sequence is HIV tat amino acids 1–72, and the signal (leader) sequence is from proinsulin, the nucleic acid sequence is provided in SEQ ID NO:31, and the amino acid sequence is provided in SEQ ID NO:32.

In a non-limiting example of a gene therapy approach to deliver paracrine-acting chimeric CDKi and adenovirus E4 proteins to a neoplastic cell, a non-viral replication-deficient plasmid encoding secretable, intemalizable adenovirus E4 protein and secretable, internalizable W9 protein is used to transfect non-neoplastic cells. The plasmid may contain a selectable marker gene (eg., neo) to allow its stable integration into transfected cells exposed to that marker (e.g., G418). To reduce the size of the plasmid, the two protein-encoding nucleic acid sequences may be positioned bi-directionally on the plasmid, each having its own promoter while sharing the same poly A signal. The transfected non-neoplastic cell then secretes secretable, internalizable adenovirus E4 protein and secretable, internalizable W9 protein, which are internalized by neoplastic cells and thereby act in a paracrine fashion to induce apoptosis in the non-transfected neoplastic cells.

IV. Preparation of Therapeutic Compositions of the Invention

The nucleic acid and protein compositions of the invention may be combined with pharmaceutically acceptable carriers to generate therapeutic compositions for use in vivo. Accordingly, the nucleic acid and protein compositions of the invention may be formulated for administration with pharmaceutically acceptable carriers such as water, buffered saline, polyol (e.g., glycerol, propylene glycol, liquid polyethylene glycol), or suitable mixtures thereof. In one embodiment, the nucleic acids or proteins of the invention are dispersed in liquid formulations, such as micelles or liposomes, which closely resemble the lipid composition of natural cell membranes. Methods for making pharmaceutically acceptable carriers and formulations thereof are found, for example, in *Remington's Pharmaceutical Sciences* (18th edition), ed. A. Gennaro (1990) Mack Publishing Company, Easton, Pa.

Formulations for parenteral administration may, for example, contain sterile water, or saline, polyalkylene glycols such as polyethylene glycol, oils of vegetable origin, or hydrogenated napthalenes.

Biocompatible, biodegradable lactide polymer, lactide/glycolide copolymer, or polyoxyethylene-poloxypropylene copolymers may be used to control the release of the chimeric CDKi and adenovirus E4 proteins. Other potentially useful parenteral delivery systems include ethylenevinyl acetate copolymer particles, osmotic pumps, implantable infusion system, and liposomes.

V. Preparation of Cells of the Invention

Any cell, but preferably an animal cell, can be transfected or transduced with the nucleic acid sequences of the invention which encode secretable, intemalizable forms of chimeric CDKi protein and adenovirus E4 protein. Cells transfected or transduced in vitro may be implanted back into the animal from which they were collected. In vivo, the cells containing the nucleic acid sequences of the invention will express and secrete chimeric CDKi and adenovirus E4 proteins, which are internalized by surrounding cells. If the cell internalizing the secretable, internalizable forms of the chimeric CDKi and adenovirus E4 proteins is neoplastic, apoptosis will be induced in that cell. If the cell internalizing the secretable, intemalizable forms of the chimeric CDKi and adenovirus E4 proteins is non-neoplastic, the proteins will not induce apoptosis, but may induce growth arrest. Eventually, the cell secreting the secretable, internalizable forms of the chimeric CDKi and adenovirus E4 proteins may internalize enough of these proteins to itself apoptose or be arrested in growth.

In one non-limiting example, an animal cell may be transfected with a linearized plasmid. The plasmid comprises nucleic acid sequences encoding secretable, internalizable form of a W9 protein and secretable, internalizable form of an adenovirus E4 protein, where the sequences are positioned for expression in the cell. The plasmid may also contain a transgene encoding a selectable marker (e.g., resistance to a drug). Following transfection, the cells are incubated in culture medium containing an amount of drug sufficient to kill non-plasmid containing cells. The plasmid-containing cells are thus selected for. Because the cells secrete an internalizable form of the W9 protein and an internalizable form of an adenovirus E4 protein, these proteins can be readily obtained from the conditioned medium of the cells. Preferably, the cell to be stably transfected is a non-neoplastic cell, so that if the transfected cell should internalize any of the W9 protein and adenovirus E4 protein it has secreted, it will be growth arrested, but will not be induced to undergo apoptosis unless it internalizes a concentration of proteins much higher than that required to induce apoptosis in neoplastic cells.

The plasmid used to generate the cells of the invention may comprise nucleic acid sequences encoding a secretable, internalizable form of a chimeric CDKi protein and a secretable, internalizable form of an adenovirus E4 protein, where the sequences are operably linked to a constitutive promoter or an inducible promoter. It will be understood that the secretable, internalizable form of a chimeric CDKi protein and secretable, internalizable form of an adenovirus E4 protein need not share the same type of regulatory sequences. For example, the nucdeic acid sequence encoding a secretable, internalizable form of a chimeric CDKi protein may be operably linked to a constitutive promoter and the nucleic acid sequence encoding a secretable, internalizable form of an adenovirus E4 protein may be operably linked to an inducible promoter.

It will also be understood that the cells of the invention need not be transfected or transduced with only one plasmid and/or recombinant virus. For example, a cell may first be transfected with a plasmid encoding a secretable, internalizable form of a chimeric CDKi protein and a hygromycin resistance marker. After a stable cell line expressing and secreting a secretable, internalizable form of a chimeric CDKi protein is established, that cell line may be transduced with a replication-deficient virus encoding a secretable, internalizable form of an adenovirus E4 protein and a neomycin resistance marker.

In addition, the cells of the invention need not be transfected with an entire plasmid. For example, transgenes comprising nudeic acid sequences encoding a chimeric CDKi protein, an adenovirus E4 protein, and a resistance marker gene may be excised from plasmids prior to their transfection into a cell. The transgenes alone will then be incorporated into a transfected cell, which will express the chimeric CDKi protein, the adenovirus E4 protein, and the resistance marker gene.

In accordance with the present invention, the compositions of the invention may be used in the following in vitro and in vivo methods.

I. In Vitro Use of the Compositions of the Invention

The nucleic acid and protein compositions of the invention find use in a variety of in vitro methodologies. For example, the compositions may be used in assays to eliminate a specific subpopulation of cultured cells. Additionally, the compositions of the invention may be used in assays to determine which type of neoplastic cell is susceptible to treatment with the compositions of the invention. The compositions of the invention also find use in assays to synchronize cell growth in cultured cells.

The nudeic acid compositions can be used, for example, in vitro in cell-based assays used to eliminate a subpopulation of cells by apoptosis. These assays may be used, for example, to screen for reagents that inhibit a particular signal transduction pathway. In this example, it may be desired to identify molecules that block a signal transduction pathway induced by a hormone. A549 cells may be stably transfected with plasmids comprising both a chimeric CDKi protein-encoding nucleic acid sequence and an adenovirus E4 protein-encoding nucleic acid sequence, where the sequences are operably linked to a promoter inducible by the hormone. When the transfected cells are treated with the hormone, they will be induced to undergo apoptosis. A retroviral or plasmid library encoding peptides may be generated and introduced into the stably transfected A549 cells. When these cells are treated with the hormone, the majority of the cells will die. However, the cells containing a peptide from the library that inhibits the signal transduction pathway induced by the hormone will not die. These cells, thus isolated by their survival, can be expanded, and the library member rescued to isolate the peptide capable of inhibiting the signal transduction pathway induced by the hormone.

In another example, an in vitro assay may be used to determine the genotype of neoplastic cells most susceptible to induction of apoptosis following the in vitro administration of the nucleic acid compositions of the invention. Following methods similar to those described below in Examples IV and V, a number of different normal and neoplastic cells were transduced with an adenovirus (AV-W9) containing the entire E4 region and encoding a specific chimeric CDKi protein, namely W9, and three days post-transduction, apoptosis was assessed using a an Annexin/pI apoptosis-detection assay. The different neoplastic cells were selected for transduction based on the different tissues from which they arose. Moreover, because a majority of human tumors lack normal gene expression of the tumor suppressor gene, p53, and inactivation of the retinoblastoma- susceptibility gene RB is associated with the pathogenesis of several human cancers, the p53 and Rb status of these cells was considered. Also considered was the status of the endogenous p16 and p27 genes in these cells.

Tables IA and IB below show the ability of AV-W9 to induce apoptosis in neoplastic and normal cells, respectively.

TABLE IA

Neoplastic Cells

| AV-W9 induced Apoptosis? | Cell Name | Cell Type |
|---|---|---|
| YES | DU145 | prostate |
| YES | PC3 | prostate |
| YES | LnCAP | prostate |
| YES | A549 | lung |
| YES | SW480 | colon |
| YES | LS174 | colon |
| YES | Y79 | retinablastoma |
| Growth Arrest | Capan-1 | pancreatic |
| Growth Arrest | Hep-G2 | liver |

TABLE IB

Normal Non-Neoplastic Cells

| AV-W9 induced Apoptosis? | Cell Name | Cell Type |
|---|---|---|
| NO | coronary artery smooth muscle cells (CASMC) | smooth muscle cell |
| Minimal | coronary artery epithelial cells (CAEC) | endothelium |
| Minimal | lung epithelial | epithelium |
| Minimal | prostate stromal | stromal |
| YES | prostate epithelial | epithelium |

As shown in Tables IA and IB above, in addition to inducing cell growth arrest in both normal and neoplastic cells, AV-W9 induced apoptosis in a variety of tumor derived cell lines. However, in a variety of non-tumorigenic primary cell types, little to no AV-W9 mediated cytopathology was observed.

The non-limiting adenovirus of the invention containing the entire E4 region and encoding the chimeric CDKi, W9 (AV-W9) induced apoptosis in neoplastic cells derived from a variety of tissues, including colon, lung, liver, pancreas and prostate tumors. AV-W9 did not induce (or minimally induced) apoptosis in non-neoplastic cells derived from arteries, veins, lung, liver, pancreas and prostate. Surprisingly, the induction of tumor cell apoptosis by AV-W9 was independent of the p16, p27, p53, and Rb status of the target neoplastic cell. For example, A549 lung carcinoma cells were induced to apoptose by AV-W9 despite having normal Rb, p53, p16, and p27. PC3 prostate tumor cells, which have a functionally inactive p53 gene and normal Rb, p16, and p27 genes, were killed by AV-W9, as were Y79 retinoblastoma cells, which have homozygous deletion of the Rb gene, and normal p53, p16, and p27 genes.

In another example, the protein compositions of the invention may be used to synchronize normal cultured cells. Such synchronization may be useful, for example, to study DNA replication. In this example, a purified internalizable form of a chimeric CDKi protein and a purified internalizable form of an adenovirus E4 protein are added to cultured cells. Following administration, the cells are growth arrested, and can, thus, be synchronized at a specific point in the cell cycle upon restimulation for example, by addition of serum-rich media or by removal of the added protein with, e.g., neutralizing antibodies.

II. In Vivo Use of the Compositions of the Invention

The nucleic acid and protein compositions of the invention find use in vivo as anti-neoplastic therapeutics.

Gene therapy approaches may be employed to introduce nucleic acid compositions of the invention to neoplastic cells in vivo. These gene therapy approaches may utilize viruses, such as adenovirus, retrovirus, adeno-associated virus, lentivirus, vaccinia virus, RNA virus, or herpesvirus, or may utilize non-viral nucleic acids, such as plasmids, to introduce nucleic acid sequences encoding a chimeric CDKi protein and an adenovirus E4 protein into a cell.

The preferred gene therapy approach for delivering the nucleic acid composition to an animal having or suspected of having a neoplasm is by the packaging of the composition within a recombinant infectious virus, such as an adenovirus. Once delivered into the body (e.g., by injection), the infectious virus particles are able to transduce a cell and deliver into the transduced cell the nucleic acid composition of the invention. Viral particles may be harvested from a packaging cell following its transfection with the appropriate viral vectors.

Non-viral plasmids or transgenes comprising the nucleic acid compositions of the invention can be delivered to cells in vitro or in vivo, preferably combined with a delivery system which, for example, exploits the endocytic pathways for internalization by the target cell. Exemplary gene delivery systems of this type include liposome-derived systems, poly-lysine systems, and artificial viral envelopes. Standard transfection protocols (e.g., electroporation, calcium phosphate precipitation, biolistic transformation, and DEAE-dextran precipitation) may be used to deliver the nucleic acid composition of the invention to cells in vitro. For in vivo delivery of non-viral plasmids or transgenes, preferably, the nucleic acid is combined with a pharmaceutically acceptable carrier and combined with a gene delivery system, such as that described in Wu and Wu, U.S. Pat. No. 5,166,320, to allow internalization of the nucleic acid by a targeted cell.

Protein compositions preferably are administered in combination with a delivery system that facilitates the internalization of the composition by a target cell.

Therapeutic protein compositions that are not combined with a delivery system facilitating the internalization of the composition preferably comprise purified internalizable chimeric CDKi protein (e.g. W9) and purified internalizable adenovirus E4 protein. The protein composition may be diluted in, for example, buffered saline, and administered i.v. to the patient.

The anti-neoplastic compositions of the invention, protein compositions comprising a chimeric CDKi protein and an adenovirus E4 protein, or the nucleic acid compositions comprising a chimeric CDKi protein-encoding nucleic acid and an adenovirus E4 protein-encoding nudeic acid, may be administered by any appropriate means. For example, the anti-neoplastic compositions of the invention may be administered to an animal within a pharmaceutically-acceptable diluent, carrier, or excipient, in unit dosage form according to conventional pharmaceutical practice. Administration may begin before the animal is symptomatic.

Any appropriate route of administration may be employed, including, without limitation, parenteral intravenous, intra-arterial, subcutaneous, intramuscular, intraperitoneal, intranasal, aerosol, by suppositories, or oral administration. Therapeutics may be in the form of liquid solutions or suspensions; for oral administration, formulations may be in the form of tablets or capsules; and for intranasal formulations, in the form of powders, nasal drops, or aerosols. The anti-neoplastic compositions may be administered locally to the affected area (eg., directly into the tumor mass), or may be administered systemically. Since, with a few exceptions, the anti-neoplastic compositions of the invention kill neoplastic cells, but do not kill normal cells, the compositions of the invention may be administered systemically in situations where, for example, the cancer has metastasized throughout the body.

For example, where the anti-neoplastic compositions of the invention are nucleic acid sequences (e.g., nucleic acid sequences encoding a chimeric CDKi protein and at least one E4 protein), a plasmid encoding these sequences may be locally administered by a velocity-driven method, such as biolistic transformation to introduce foreign molecules into a cell using velocity driven microprojectiles, such as tungsten or gold particles. Other velocity-driven methods originate from pressure bursts which include, without limitation, helium-driven, air-driven, and gunpowder-driven techniques. Biolistic transformation may be applied to intact tissues, such as an intact tumor within a cancer patient.

Similarly, a chimeric CDKi protein (e.g., W9) and an adenovirus protein may be administered locally by direct injection into a tumor mass. Preferably, where the proteins themselves are injected, the proteins are purified, administered with a pharmaceutically acceptable carrier (e.g., physiological saline), and are internalizable by tumor cells.

Viral particles, such as recombinant retroviruses, carrying transgenes encoding a chimeric CDKi protein and an adenovirus E4 protein may be administered in a pharmaceutically acceptable formulation systemically via the blood stream or lymphatic system, or may be administered locally to the tumor site using a programmable pump micro-syringe, such as the micro-syringes commercially available from KD Scientific (Boston, Mass.). Other devices, such as cannulas and i.v. lines supplying virus particles to an artery supplying blood to the targeted tumor mass, may also be used for local administration of an anti-neoplastic viral particle of the invention.

If desired, treatment of a cancer patient with the anti-neoplastic compositions of the invention may be combined with more traditional therapies such as surgery, steroid therapy, radiation therapy, or chemotherapy.

Below are listed methods for delivering the compositions of the invention to the liver, the pancreas, and to the head and neck. Of course, compositions of the invention may be delivered to other organs (e.g., the kidney), and may be delivered to, for example, the liver, via the hepatic artery or vein, or systemically via any major blood vessel of the body.

For patients with hepatocellular carcinomas or colon tumor metastases, the compositions of the invention may be administered in combination with an intrahepatic delivery system.

In a non-limiting example, where the reagent of the invention is an adenovirus containing the all or part of the E4 region and encoding the W9 protein (such as the AV-W9 recombinant adenovirus described below), approximately $5\times10^{12}$ virus particles per dose are delivered through a pump connected hepatic cannula, such as those commercially available from SIMS Deltec Inc., St. Paul, Minn., in a volume of about 100 ml over 30 to 60 minutes. Administration of doses may be repeated as necessary.

For patients with pancreatic cancer, where the composition of the invention is an adenovirus encoding at least one E4 protein and the W9 protein, a therapeutically effective amount of the recombinant adenovirus may be delivered via CT-guided administration into the pancreatic vasculature. Preferably, the adenovirus lacks the entire E4 region such that not all adenovirus E4 proteins are encoded and/or expressed in an adenovirus-infected cell.

For patients with solid tumors of the head and/or neck, where the reagent of the invention is, for example, AV-W9, a therapeutically effective amount of the recombinant adenovirus may be delivered via direct injection into the tumor at multiple points.

When administered to an animal having, or suspected of having, a neoplasm, the anti-neoplastic compositions of the invention are delivered in a therapeutically effective amount. By "animal" is meant any animal, preferably a warm-blooded animal, more preferably a mammal, and most preferably a human. As used herein, the term "therapeutically effective amount" means the total amount of each active component of a therapeutic composition that is sufficient to show a meaningful patient benefit. When administered to an animal having a solid tumor, a therapeutically effective amount is an amount sufficient to slow tumor growth, more preferably, to arrest tumor growth, and, most preferably, to diminish tumor size. Where the neoplasm is a non-solid tumor, the neoplastic cells may be counted, and a therapeutically effective amount of the compositions of the invention will slow the increase in number of neoplastic cells, more preferably, prevent an increase in the number of neoplastic cells, and, most preferably, reduce the number of neoplastic cells.

When applied to an individual active component, administered alone, a therapeutically effective amount refers to that component alone. When applied in combination, the term refers to the combined amounts of the active components that result in the therapeutic effect, whether the components are administered in combination, serially, or simultaneously. What constitutes a therapeutically effective amount is within the skill of one of ordinarily skill, and can be readily determined in non-human mammals prior to use in human patients.

Where the anti-neoplastic compositions of the invention are purified chimeric CDKi protein and purified adenovirus E4 protein, a therapeutically effective amount will differ depending on a number of factors. including, without limitation, whether the proteins are internalizable by a cell, and whether the proteins are injected directly into a solid tumor or delivered systemically. It will be understood that a therapeutically effective amount does not necessarily consist of equal amounts of chimeric CDKi protein and adenovirus E4 protein. For example, in a therapeutically effective amount, there may be two chimeric CDKi protein molecules for every one adenovirus E4 protein molecule.

Where the anti-neoplastic reagent of the invention is a recombinant virus particle encoding a chimeric CDKi protein and an adenovirus E4 protein, the therapeutically effective amount will depend on, for example, whether the virus is delivered systemically or directly into a tumor, and whether the virus is replication-deficient or replication-capable. Also, the therapeutically effective amount of the recombinant virus may differ if the proteins act within the transduced cell only, or whether they also comprise a leader sequence and translocation sequence, thus allowing them to be secreted and act in a paracrine-fashion on surrounding cells. In one non-limiting example of a therapeutically effective amount, where the reagent of the invention is the replication-deficient adenovirus containing an entire E4 region and encoding the chimeric CDKi protein, W9 (AV-W9 described below), and is administered directly into a solid tumor of approximately 40 mm, approximately $1\times10^{11}$ viral particles per injection are administered per day for 3 days. A larger number of viral particles and/or administration for more than 3 days is used for solid tumors larger than approximately 40 mm$^3$.

III. Use for the Cells of the Invention

Cells containing introduced nucleic acid encoding secretable, internalizable forms of chimeric CDKi protein and adenovirus E4 protein may be used in vitro as a permanent source for secretable, internalizable chimeric CDKi protein and secretable, internalizable adenovirus E4 protein. Since the proteins are secreted, they may be purified from the conditioned medium of the cells without having to kill the cells. Where nucleic acid sequences encoding the proteins are operably linked to a constitutive promoter, it may be advisable to harvest the media frequently, to prevent internalization of the proteins by the cells.

The cells of the invention introduced with nucleic acids encoding a secretable, internalizable form of a chimeric CDKi protein and a secretable, internalizable form of an adenovirus E4 protein also find use in vivo, for example, as delivery vehicles for paracrine-acting secretable, internalizable chimeric CDKi protein and secretable, internalizable adenovirus E4 protein in an animal with a neoplasm. Preferably, the cell has the same MHC genotype as the animal being treated. Less preferably, the cell is of the same species as the animal being treated.

The use of the cells of the invention may be exemplified with the case of a patient diagnosed with prostate cancer. While the patient is being treated with other therapies, such as gene therapy with the nucleic acid compositions of the invention, a normal epithelial cell may be taken from the patient, and expanded in vitro. The expanded cells may then be stably transfected with nucleic acid sequences encoding secretable, internalizable forms of chimeric CDKi protein and adenovirus E4 protein, where the sequences are operably linked to drug-inducible promoters and are positioned for expression in the transfected cells. After a sufficient number of stably transfected cells expressing secretable, internalizable chimeric CDKi protein and adenovirus E4 protein are obtained, these cells are implanted into the patient, preferably near sites of cancerous cells. The inducing drug is then administered to the patient, and the stably transfected cells express proteins which act in a paracrine fashion and serve to induce apoptosis in the nearby cancerous cells. Once the cancer has subsided, the patient is no longer administered the inducing drug.

In a second example, a patient diagnosed with cancer given an implant of stably transfected cells lacking any MHC expression. The stably transfected cells contain nucleic acid sequences encoding secretable, internalizable forms of chimeric CDKi protein and adenovirus E4 protein, where the sequences are operably linked to constitutive promoters and are positioned for expression in the transfected cells. Once implanted, the stably transfected cells express and secrete paracrine-acting chimeric CDKi and adenovirus E4 proteins. Once the cancer has subsided, the stably transfected cells may be surgically removed.

The following examples illustrate the preferred modes of making and practicing the present invention, but are not meant to limit the scope of the invention since alternative methods may be utilized to obtain similar results.

EXAMPLE I

Generation of p27/p16 Fusion Proteins

To create more potent anti-proliferative molecules that possess the activities of both the INK4 (p16) and CIP/KIP (p27) families, a number of recombinant CDKi's were created that fused the parental human p16 and p27 molecules, or their derivatives. The modified CDKi's included fusion proteins of p16 fused to 5' and 3' truncated p27 molecules. These fusion proteins were designed to increase the protein's half-life and eliminate potential phosphorylation sites involved in the negative regulation of CDKi activity. The p27-p16 fusion proteins interacted with the CDK4/cyclinD, CDK2/cyclinA, and CDK2/cyclinE complexes and inhibited cell cycle progression at multiple points.

To generate the following non-limiting, representative CDKi fusion proteins of the present invention (and nucleic acid sequences encoding these proteins), the published sequences of the human p16 and p27 molecules were utilized. The nucleic acid (SEQ ID NO: 25) and amino acid (SEQ ID NO: 26) sequence of human p27 is available as GenBank Accession No. U10906 (Polyak et al. (1994) *Cell* 78: 56–66). The nucleic acid (SEQ ID NO: 27) and amino acid (SEQ ID NO: 28) sequence of human p16 is available as GenBank Accession No. L27211 (Serrano et al. (1993) *Nature* 366: 704–707; Okamoto et al. (1994) *Proc. Natl. Acad. Sci. USA* 91: 11045–11049). To construct the representative, non-limiting CDKi fusion proteins of the invention, in general, PCR primers were used to insert a NdeI cloning site followed by sequence encoding 6×His and an epitope tag from the influenza virus hemagglutinin protein (HA tag) at the 5' end of full length p27 or truncated p27$_{25-93}$ and p2712-178. In each instance, the CDKi gene was followed by an amber stop codon with SalI cloning site. The NdeI-SalI fragments were amplified by Deep Vent polymerase (commercially available from New England Biolabs, Beverly, Mass.) and cloned into plasmid pT7-7 (commercially available from US Biological (USB), Swampscott, Mass.) to yield pT7-His6-HA-p27, pT7-His6-HA-p27$_{25-93}$ and pT7-His6-HA-p27$_{12-178}$. To generate fragments without a stop codon and a (Gly$_4$Ser)$_3$ linker, an alternate set of 3' PCR primers were used to insert sequence coding for a (Gly$_4$Ser)$_3$ linker in place of the stop codon with SalI cloning site at the 3' end. These NdeI-SalI amplified fragments were then subcloned into a NdeI and XhoI digested pKS plasmid containing full length p16, with the initiating ATG removed, generating an open reading frame in which the various p27 derivatives and full length p16 are linked by (Gly$_4$Ser)$_3$, histidine, and aspartic acid. The representative, non-limiting CDKi proteins of this example are schematically depicted in FIG. 2A, and were constructed as follows:

To construct the nucleic acid sequence encoding the p27-p16 fusion protein (i.e., N-terminal p27 and C-terminal p16) having a (Gly$_4$Ser)$_3$ hinge region between the p27 and p16 portions (W3), the p27 coding sequence was first PCT amplified using the following primers:

N-terminal primer, which carries an NdeI site and 6 histidine codons that are inserted between the ATG and the second amino acid of p27 (SEQ ID NO: 1): 5'-GCGGCCGGTCATATGCACCACCATCACCA TCACTCAAACGTGCGAGTGTCT-3'; and C-terminal primer, which carries the (Gly$_4$Ser)$_3$repeat and EcoRI, SalI, and HindII restriction sites and eliminates the stop codon of p27 (SEQ ID NO: 2): 5'-GCCGCCGG CGTCGACTCGGC-CGAATTCGGATCCACCCCCGCCGGAACCGCCACC CCCGCTGCCCCCGCCACCCGTTTGACGTCTTCTGA GGCCAGG-3'.

The p27 PCR product was digested with NdeI and HindIII and inserted into pT7-7 linearized with NdeI and HindIII. The resulted construct was digested with EcoRI and SalI and a full length p16 PCR product was inserted as an EcoRI-XhoI fragment. The position of the EcoRI site allows the in-frame insertion of p16. The rest of the hinge region between the p27 and p16 coding sequences is derived from the 5' end of the p16 cDNA. The nucleic acid and amino acid sequence of W3 are provided, respectively, in SEQ ID NO: 3 and SEQ ID NO: 4.

A nucleic acid sequence encoding a second p27-p16 fusion protein, W4, was generated, where the p27 and p16 portions were not separated by a (Gly$_4$Ser)$_3$ hinge region. The W4-encoding nucleic acid sequence construct indudes a 5' EcoRI site, along with the coding sequence for a N-terminal HA tag, and a 3' NotI site. The nudeic acid and amino acid sequence of W4 are provided, respectively, in SEQ ID NO: 5 and SEQ ID NO: 6.

Two p16-p27 fusion proteins (i.e., N-terminal p16 and C-terminal p27), W5 (having a (Gly$_4$Ser)$_3$ hinge region located between the p16 and p27 portions) and W6 (not having a a (Gly$_4$Ser)$_3$ hinge region) were similarly generated. The nucleic acid and amino add sequence of W5 are provided, respectively, in SEQ ID NO: 7 and SEQ ID NO: 8. The nucleic acid and amino acid sequence of W6 are provided, respectively, in SEQ ID NO: 9 and SEQ ID NO: 10.

In addition, a series of a series of truncated versions of p27 designed to increase the protein half-life were fused to full-length p16 at the N-terminus. In one p27 truncation, p27$_{12-178}$, the first 12 N-terminal and the last 20 C-terminal amino acids were removed from full length p27 to remove a CDK consensus phosphorylation site (TPKK) at amino acids 187–190, two other potential phosphorylation sites for proline directed kinases, at amino acids 178–181 (SPN), and a weak CDK phosphorylation site (SPSL) at amino acids 10–13 (Sheaff et al. (1997) *Genes & Dev.* 11: 1464–1478; Morisaki et al. (1997) *Biochem. Biophys. Res. Commun.* 240: 386–390). The nucleic acid and amino acid sequences of this truncated p27 protein (12aa–178aa) are shown in SEQ ID NO: 11 and SEQ ID NO: 12, respectively, which provide a polypeptide of the formula EcoRI-ATG-HA epitope-p27 (12–178aa)-Stop-NotI.

W7 comprises amino adds 12–178 of p27 fused to full length p16, where the p27 and p16 portions are separated by a (Gly$_4$Ser)$_3$ hinge region. The nucleic acid and amino acid sequence of W7 are provided, respectively, in SEQ ID NO: 13 and SEQ ID NO: 14. W8 comprises amino acids 12–178 of p27 fused to full length p16, where the p27 and p16 portions are not separated by a (Gly$_4$Ser)$_3$ hinge region. The nucleic acid and amino acid sequence of W8 are provided, respectively, in SEQ ID NO: 15 and SEQ ID NO: 16.

In a second truncation of p27, p27$_{25-93}$, only the CDK inhibitory domain of p27 (amino acids 25–93) was retained. This domain contacts both the CDK and cyclin binding subunits and is sufficient for kinase inhibition, while lacking the nuclear localization signal at amino acids 152–166 and the QT domain, a potential site for protein interactions, at amino acids 144–194 (Russo et al. (1998) *Nature* 395: 237–243). Thus, the p27$_{25-93}$ CDKi was created to eliminate amino acid residues that may play a role in targeting the parental p27 molecule to the ubiquitin- proteosome degradation pathway or may play a role in p27 phosphorylation. The nucleic acid and amino add sequences of this truncated p27 protein (25aa–93aa) are shown in SEQ ID NO. 17 and SEQ ID NO: 18, respectively, which provide a polypeptide of the formula EcoRI-ATG-HA epitope-p27 (25–93aa)-Stop-NotI.

The p27$_{22-93}$ fragment were fused to the N-terminus of p16 with (W10) or without (W9) the (Gly$_4$Ser)$_3$ hinge (FIG. 2A). The nucleic acid and amino acid sequence of W9 are provided, respectively, in SEQ ID NO: 19 and SEQ ID NO: 20. The nucleic acid and amino acid sequence of W10 are provided, respectively, in SEQ ID NO: 21 and SEQ ID NO: 22.

W3, W8, and W10 were further subcloned into a modified pGEX4T-1 plasmid (Pharmacia Biotech, Uppsala, Sweden) (where a NdeI cloning site was inserted between the BamHI and EcoRI sites) as NdeI-NotI fragments to generate glutathione S-transferase (GST) tagged fusion proteins. A similar strategy was used to generate fusion proteins without the (Gly$_4$Ser)$_3$linker (i.e., W4 (p27-p16), W7 (p27$_{12-178}$-p16), and W9 (p27$_{25-93}$-p16)). The nucleic acid and amino acid sequences of the p27$_{25-93}$-p16 fusion CDKi, W9, without the HA tag and six histidine residues are provided in SEQ ID NO: 23 and SEQ ID NO: 24, respectively, and in FIG. 2B.

p27, p27$_{25-93}$, and p27$_{12-178}$ proteins were expressed in *E. coli* BL21 strain using the pT7 plasmids described above. For protein expression, cells were grown in LB+50 mg/ml ampicillin at 37° C. to OD$_{600}$=0.8 and protein expression was induced by IPTG (final; conc.: 20 mM) for 4 hours as 37° C. Cells were collected and the pellet was frozen at −80° C. The preparation of the cell lysate and binding to a Ni$^{2+}$ charged sepharose resin (Invitrogen Corp, San Diego, Calif.; Catalog no. R801) was done according to the manufacturer's instruction (Invitrogen; see also Hochuli et al. (1987) *J. Chromatography* 411:177–184; Janknecht et al. (1991) *Proc. Natl. Acad. Sci. USA* 88:8972–8976). The bound proteins were eluted with 50 mM, 200 mM, 350 mM, and 500 mM imidazol and the fractions were analyzed on SDS/PAGE. The 200 mM, 350 mM, and 500 mM imidazol fractions were collected, dialysed against 1×PBS (1 mM KH$_2$PO$_4$, 10 mM Na$_2$HPO$_4$, 137 mM NaCl, 2.7 mM KCl, pH 7.4)+10% glycerol and stored at −80° C. in aliquots. Approximately 25% of the prep was the protein.

p27$_{25-93}$ and p27$_{12-178}$ were further purified by gel filtration column chromatography using a Superdex 75 FPLC column equilibrated with 10% glycerol in PBS. Expression and purification of the GST-tagged W3, W4, W7, W8, W9, and W10 fusion proteins was essentially as described (Gyuris et al. (1993) *Cell* 75: 791–803). The purified GST-fusion proteins were then buffer exchanged by dialysis into 50 mM Tris-HCl pH 8.0, 150 mM NaCl, 2 mM CaCl$_2$. The GST domain was removed from the fusion proteins by enzymatic cleavage with 1 unit (USB units) of thrombin/mg of protein/hour (thrombin commercially available from USB). Following cleavage, the thrombin was inactivated with 2 fold molar excess of PPACK (USB). The cleaved GST moiety was then removed by passing the protein solution over a column of glutathione-Sepharose. Protein concentration was determined using a protein assay (BioRad, Cambridge, Mass.) with bovine serum albumin (BSA) as a standard. In order to more accurately determine the concentration and purity of the specific proteins in each of the preparations, the protein samples were subjected to SDS-PAGE, and stained with coomassie blue. The stained gels were analyzed using the Gel Doc 1000 image analysis system and Molecular Analyst software (BioRad).

The p27 and p16 CDKi's appear to fold correctly in all of the fusion protein CDKi's, as the biochemical data indicates that the p27 moieties were functional and intra-cellular staining with anti-p16 antibodies indicate that at least at a gross level, the p16 molecules were folded correctly.

EXAMPLE II

In Vitro Kinase-Inhibiting Activities of the CDKi Proteins

The natural substrates for p27 and p16 CDKi's are cyclin-dependent kinase (CDK) complexes that are formed via the association of different catalytic CDK and regulatory cyclin subunits. The CDK4/cyclin D and CDK6/cyclin D complexes regulate progression through G$_1$ phase, the CDK2/cycin E kinase regulates the G$_1$/S transition, the CDK2/cyclin A complex drives the cells through S-phase, and the entry and exit from mitosis is controlled by the CDC2/cyclin B complex (Sherr, C. J. (1996) *Science* 274: 1672–1677). CDKi's regulate the activity of the CDK complexes through a combination of phosphorylation events and physical association (Morgan, M. (1995) *Nature* 374: 131–134). The redistribution of CDKi's between the different CDK/cyclin complexes during the cell cycle coordinates the timing of activation and de-activation of their kinase activity (Sherr and Roberts (1995) *Genes and Dev.* 9: 1149–1163).

To determine the ability of the CDKi proteins of the invention, their abilities to inhibit the in vitro kinase activity of CDK4/cyclin D1, CDK2/cyclin E, and CDC2/cyclin B complexes was determined. The purity of the various p27-p16 fusion proteins, p27, and p16 preparations were normalized using p16 and p27 specific antibodies.

Active CDK4/cyclin D1, CDK2/cyclin E, and CDC2/cyclin B complexes were obtained from Sf9 insect cells transfected with baculoviruses expressing recombinant cyclins and CDK's. Briefly, the assay employed Sf9 cell extracts that were made from cells that were coinfected with the proper CDK and cyclin expression constructs. Typically, 44 mg of Sf9 extract in 50 ml of 50 mM Tris-HCl pH 7.6, 10 mM MgCl$_2$, 1 mM DTT, 25 mM ATP, 10 mCi $^{32}$P-γ-ATP was used in the absence of the presence of the particular inhibitor (inhibitor concentration was between 25 nM to 1 mM). Partial purification of CDK4/cyclin D1 was achieved by a 20–40% ammonium sulfate preparation of the cell lysate and was used in the assays. CDK2/cydin E was purified to greater than 90% and pretreated with CDKactivating kinase (CAK) (Morgan, M., supra) for full activation. CDC2/cyclin B was expressed as a GST fusion protein (CDC2/GST-cyclin B) and purified on glutathione-Sepharose column, cleaved by thrombin, and followed by another glutathione-Sepharose separation for the removal of the cleaved GST. GST-fused Rb (glutathione S-transferase fusion with amino acids 379–928 from the C terminus of pRB; GST-Rb) was used as a substrate for the CDK4/cyclin D1 and CDK2/cyclin E assays; histone H1 was the substrate for CDC2/cydin B. The reaction was carried out at 30° C. for 30 minutes using 2 mg of substrate. These assays were carried out in 96 well plates (Nunc, Naperville, Ill.) and monitored by $\gamma$-$^{32}$P-ATP incorporation.

The reactions were initiated by addition of the insect cell-expressed CDK (eg., CDC2/cyclin B) and the *E. coli*-expressed CDKi (eg., p27 and W9). The concentrations of GST-Rb and histone H1 were 4.4 mM and 19 mM, respectively, and the concentration of ATP was 50–60 mM. The reaction mixtures contained 50 mM Tris-Cl pH 7.5, 10 mM MgCl$_2$, and 1 mM DTT in a total volume of 50 or 100 $\mu$l. After incubation at 30° C. for 10–20 minutes, the reaction was terminated by the addition of a stop solution containing EDTA. The phosphorylated substrates were captured either by GST-Sepharose or TCA precipitation and then monitored for radioactivity (Microplate Scintillation Counter, Packard, Meriden, Conn.).

The concentration of CDKi protein at which 50% of the kinase activity was blocked (IC$_{50}$) was calculated for various cyclin/CDK pairs. The results are indicated in Table II (below) and in FIG. 2A (three columns labeled CDK4/cyclin D1 (nM), CDK2/cyclin E (nM), and CDK2/cyclin B (nM)). Moreover, the inhibition constant, K$_i$ for the inhibition of CDK4/cyclin D1 by p27/p16 fusion protein was determined to be 23 nM, compared to a K$_i$ of 75 nM for p16 inhibition of the same CDK4 complex.

TABLE II

Inhibition of cyclin dependent kinase complexes by p27-p16 fusion protein

| inhibitor | CDK4/ cyclin D1 | CDK2/ cyclin E | CDK2/ cyclin A | cdc2/ cyclin B |
|---|---|---|---|---|
| p27-p16 | 25 nM | 30 nM | 25 nM | 15 nM |
| p27 | 63 nM | 52 nM | 65 nM | 20 nM |
| p16 | 250 nM | >500 nM | >500 nM | >500 nM | nM = nanomolar

As shown in Table II and FIG. 2A, p16 was a potent inhibitor of the CDK4/cyclin D1 kinase. In contrast, p27 was a powerful inhibitor of all three kinase complexes. The various p27 modifications did not positively impact the monomeric or fusion protein CDKi's inhibitory activity in vitro (see FIG. 2A). In general, the order of the p16 and p27 CDK in the fusion CDKi does not appear to impact the activity of the fusion CDKi. Moreover, the (Gly$_4$Ser)$_3$ hinge region is not necessary to retain p27 function in the fusion CDKi.

Thus, in vitro kinase inhibition experiments indicated that the potency of the purified p27$_{12-178}$, p27$_{25-93}$ or the fusion p27/p16 proteins (W3, W4, W7, W8, W9, and W10) were not appreciably different from that of full-length p27 or an equimolar mixture of p16 and p27. The activity of the CDK4/cyclin D1 complex was inhibited by both p16 and p27.

EXAMPLE III

Construction of Recombinant Adenoviruses Encoding p16, p27, and the p27/p16 Fusion Proteins The adenovirus vector system used for the construction of replication deficient, E1 region- and E3 region-deleted, E4 region-containing adenovirus 5 (AdS) recombinants was purchased from Microbix Biosystems Inc. (Toronto, Ontario, Canada). The six-his residue, HA-tagged inhibitors were positioned for expression under the control of the CMV promoter/enhancer and the SV40 polyA signal.

Figure 3:
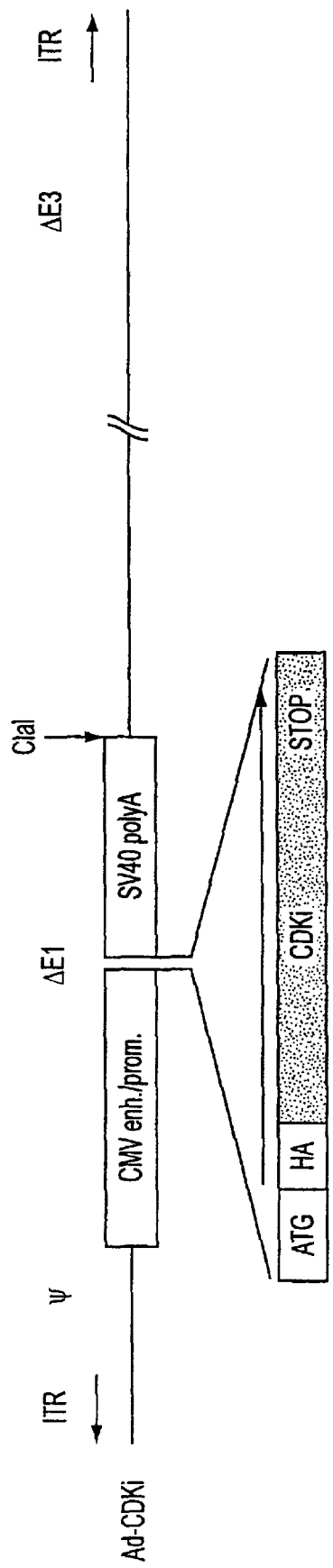
FIG. 3 is a diagrammatic representation showing the structure of non-limiting, representative replication-deficient recombinant adenoviruses of the invention that encode CDKi's (AV-CDKi's). These recombinant adenoviruses contain the entire E4 region, which is located between the deleted E3 region (ΔE3) and the left ITR; thus these adenoviruses also encode all of the E4 region proteins. The expression of the CDKi's is regulated by the CMV enhancer and promoter and the SV40 poly A sequence. Each CDKi was fused to the HA epitope tag. The ATG is in the context of the optimal Kozak sequence. ClaI is the restriction site used for construction of the recombinant viruses.

The adenovirus containing the E4 region and encoding p27 (AV-p27) was constructed by in vivo recombination in 293 cells following the manufacturer's instructions (Microbix). AV-p27 DNA was isolated from the amplified virus and digested with ClaI. This digest removed the p27 expression cassette and the left inverted terminal repeat (ITR) and packaging signals of Ad5 (see FIG. 3). HA-tagged p16, p27$_{25-93}$, p27$_{12-178}$, W3, W7, and W9 molecules were cloned into a plasmid, pKS-ITR-CMV, which contains the expression cassette as well as the left ITR and packaging signals with flanking EcoRV and ClaI restriction sites. The order of the functional elements is the following from 5' to 3': EcoRV-left ITR-packaging signal-CMV enhancer/promoter-CDKi insert-SV40 polyA-ClaI. The EcoRV-ClaI fragments containing the CDKi inserts were ligated to the deleted, large Ad5 DNA in vitro and the ligated DNA was transfected into 293 cells (commercially available from the American Type Culture Collection (ATCC), Manassas, Va.).

Infectious, recombinant virus particles were rescued from 293 cells. The unligated, large Ad5 fragment was unable to generate infectious viruses alone because of the lack of the left ITR and packaging signal that are essential for virus replication. Infectious recombinants formed only when the small EcoRV-ClaI fragment containing the left ITR, packaging signal, the expression cassette and the CDKi insert was ligated to the ClaI digested end of the Ad5 DNA re-creating an infectious Ad5 recombinant virus DNA.

EXAMPLE IV

Stability of p16, p27, and the p27/p16 Fusion Proteins Delivered by an Adenovirus Containing the Entire E4 Region p27 has been reported to be a short lived protein in proliferating cells (Pagano et al. (1995) *Science* 269: 682–685; Hengst and Reed (1996) *Science* 271: 1861–1864). To determine the half-life of the various CDKi in CASMC's, pulse-chase experiments were performed using CASMC's transduced with the adenoviruses containing the entire E4 region and encoding the various CDKi (AV-CDKi's).

Human coronary artery smooth muscle cell (CASMCs) were obtained from Clonetics (Walkersville, Md.). Low passage CASMC (less than passage 10) were plated at 3500 cells/cm in complete SMC media (Clonetics, plus 5% FBS and growth factors) and allowed to recover overnight. For proliferating cells, cultures were maintained throughout in complete SMC. For quiescent cells, cultures were serum starved for 48 hours in low serum media (SMC media with 0.05% FBS and 1:100 growth factors).

Growth arrested (G$_0$) and proliferating (A$_s$) CASMC were transduced at a multiplicity of infection (MOI) of 50 with the various recombinant adenoviruses containing the E4 region and encoding CDKi's. Twenty-four hours later, the cells were radiolabeled ("pulsed") for 2 hours in media containing $^{35}$S-methionine. The $^{35}$S-methionine containing media was then removed and replaced with media containing an excess of non-radiolabeled amino acids, and the cells "chased" for 0, 1, 3, 9, 18 hours and 0, 1, 2,3,4, and 5 days. Cell pellets were lysed in 50 mM Tris-Cl pH 7.5,250 mM NaCl, 0.5% NP-40, 50 mM NaF, 5 mM EDTA, 1 mM PMSF, 1 mM Sodium Vanadate, and protease inhibitors. Protein concentrations were determined using a protein assay (Biorad) with bovine serum albumin (BSA) as a standard. Equivalent amounts of total protein from the cells were then immunoprecipitated using antibodies bound to protein A-sepharose. The antibodies used were p27 (Kip1, commercially available from Transduction Laboratories, Lexington, Ky.), and p16-C20 (commercially available from Santa Cruz Biotech., Santa Cruz, Calif.). The immunoprecipitates were separated by SDS-PAGE, and the gels vacuum dried and exposed to film. The radiolabeled proteins on the autoradiographs were analyzed using the Gel Doc 1000 image analysis system and Molecular Analysts software (Biorad).

The observed molecular weights of the expressed, HA epitope tagged proteins corresponded to the expected sizes: p27, approximately 30 kD; $p27_{12-178}$, approximately 28 kD; $p27_{25-93}$, approximately 10 kD; p16, approximately 19 kD; W3, approximately 48 kD; W7, approximately 46 kD; and W9, approximately 30 kD (data not shown).

The kinetics of signal decay from the immunoprecipitated CDKi's was assessed by autoradiography at specific timepoints (see FIG. 2A). The half-life of the CDKi's was estimated as the time-point at which half the original CDKi protein signal remained. In quiescent CASMC ($G_0$ cells), the p16, p27, W3, W7, and W9 proteins all had half-lives of 2 to 3 hours (FIG. 2A). The only significant difference was observed in proliferating cells($A_S$), where the W7 protein demonstrated a half-life of 20 hours.

EXAMPLE V

AV-W9 Has a Potent Anti-Proliferative Activity in Neoplastic Cells

Figure 4B:
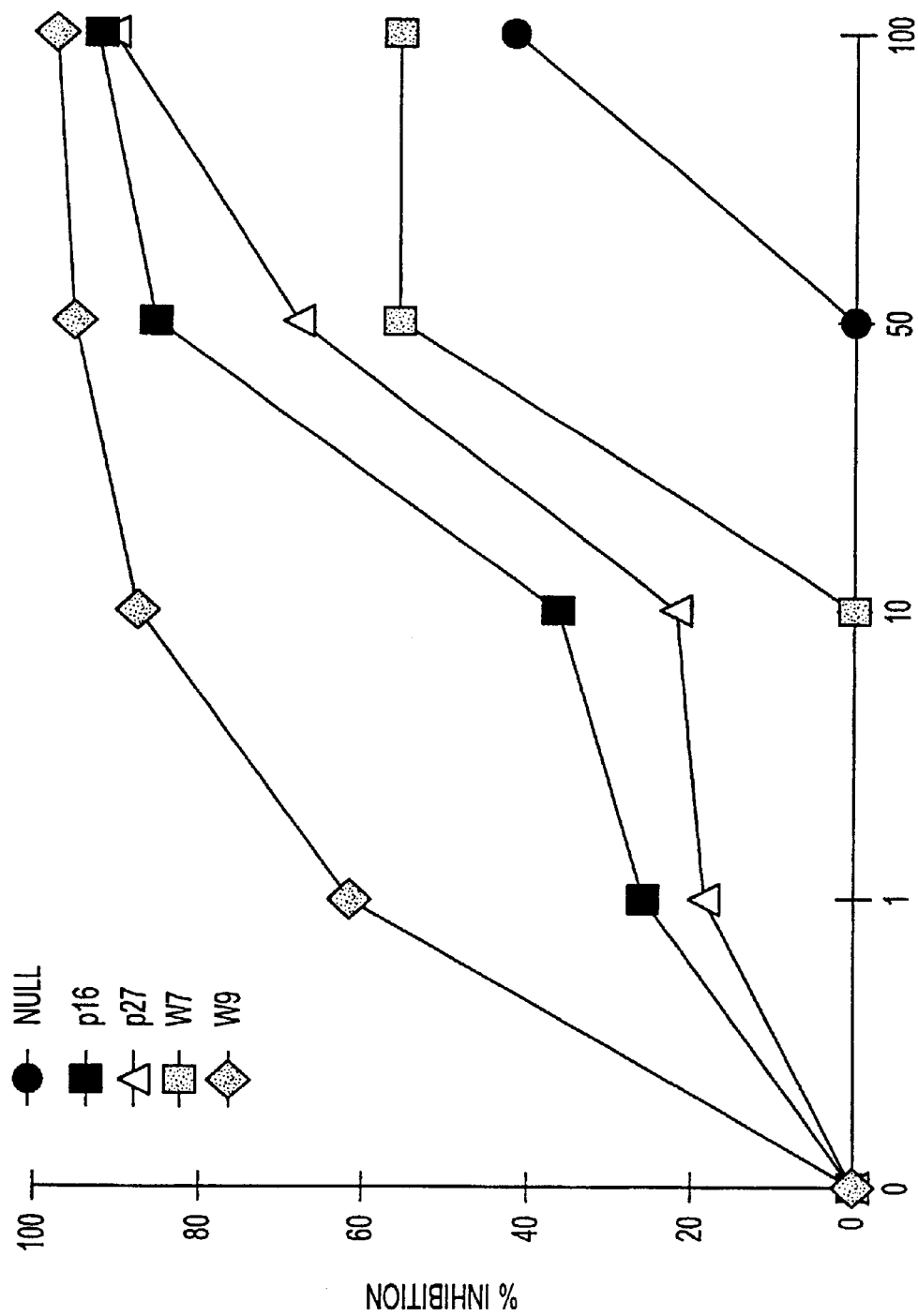
FIG. 4B is a representation of a line graph showing the ability of non-limiting, representative AV-CDKi's of the invention to inhibit proliferation of A549 lung carcinoma cells. Shown is the percent inhibition of cell growth following transduction with adenovirus containing an entire E4 region (AV) and a CMV promoter operably linked to no insert (Null, circles), p16 (solid squares), p27 (triangles), W7(hatched squares), and W9 (diamonds)

AV-W9 inhibited cell proliferation of SW480 colon carcinoma cells (FIG. 4A) and A549 lung carcinoma cells (FIG. 4B) at lower MOI than AV-delivered parental molecules p16 or p27, AV-W7, and AV-Null. The ratio of virus particle/plaque forming units for the p16, p27, W7, and W9 were similar (305 vp/pfu, 267 vp/pfu, 141 vp/pfu, and 197 vp/pfu, respectively). For these experiments, $1 \times 10^5$ cells were plated per well in a 6 well plate. Following cell adherence, the media was partially aspirated, and virus was added at the indicate MOI's. After 2 hours, fresh media was added to each well, and the cells were incubated for 1–3 days. For analysis, cells were harvested, washed with PBS, and assessed for apoptosis using the TdT TUNEL assay (Pheonix Flow Systems, San Diego, Calif.) and/or the Annexin binding assay (R&D Systems, Minneapolis, Minn.) according to manufacturers' instructions. Cells were also analyzed for viability using Trypan blue labelling and cell cycle arrest by counting the number of viable cells to estimate cell growth and proliferation.

EXAMPLE VI

AV-W9 Induced Apoptosis in Neoplastic Cells

Figure 5B:
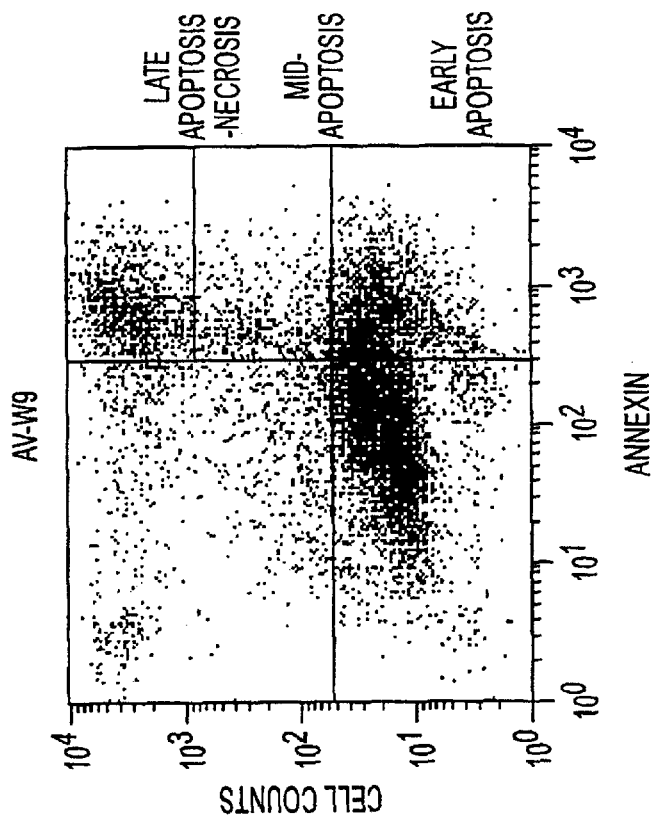
FIG. 5B is a representation of a FACS histogram showing the induction of apoptosis in A549 lung carcinoma cells by a non-limiting, representative adenovirus of the invention containing the entire E4 region and encoding W9 (AV-W9). A549 cells were transduced AV-W9, harvested 2 days later, and the level of apoptosis ascertained by Annexin-PI staining, followed by FACS analysis.
Figure 5A:
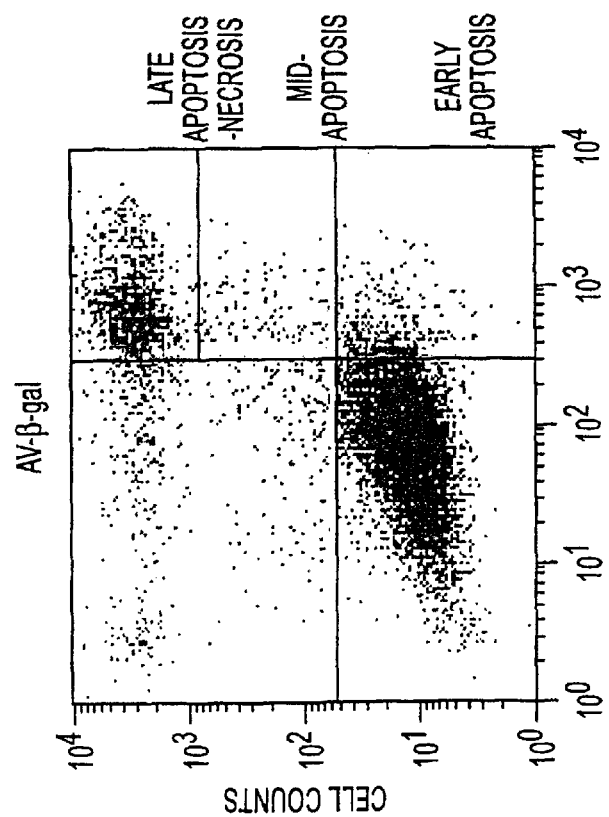
FIG. 5A is a representation of a FACS histogram showing the lack of induction of apoptosis in A549 lung carcinoma cells by an adenovirus containing the entire E4 region and encoding β-gal (AV-β-gal). A549 cells were transduced with AV-β-gal, harvested 2 days later, and the level of apoptosis ascertained by Annexin-PI staining, followed-by FACS analysis.

The ability of AV-W9 to induce apoptosis in neoplastic cells was examined. First, A549 lung carcinoma cells were transduced with equivalent amounts of adenovirus containing the E4 region and encoding either β-gal or W9 (FIGS. 5A and 5B, respectively). Transduced cells were harvested 2 days later and the level of apoptosis ascertained by Annexin-PI staining. With this double staining, non-apoptotic cells appear in the lower left quadrant of the histogram; nuclei from dead cells appear in the upper left quadrant of the histogram. The apoptotic cells appear in the right half of the histogram, with late apoptotic/necrotic cells appearing at the top right corner of the histogram, mid-stage apoptotic cells appearing in the middle of the right half of the histogram, and early stage apoptotic cells appearing at the lower right corner of the histogram.

Although there was some necrosis in cells transduced with AV-β-gal (FIG. 5A), transduction with AV-W9 induced early, middle, and late stage apoptosis in lung carcinoma cells (FIG. 5B).

The ability of AV-W9 to induce apoptosis in PC3 prostate tumor cells, SW480 colon carcinoma cells, and A549 lung carcinoma cells was also examined. To do this, PC-3, SW480, or A549 cells were transduced as before with the indicated AV-CDKi at multiplicity of infection (MOI) of 1, 10, 50, and 100 and apoptosis was assessed after 3 days using a TdT TUNEL based apoptosis assay according to manufacturer's instructions (Pheonix Flow Systems, San Diego, Calif.).

Figure 6B:
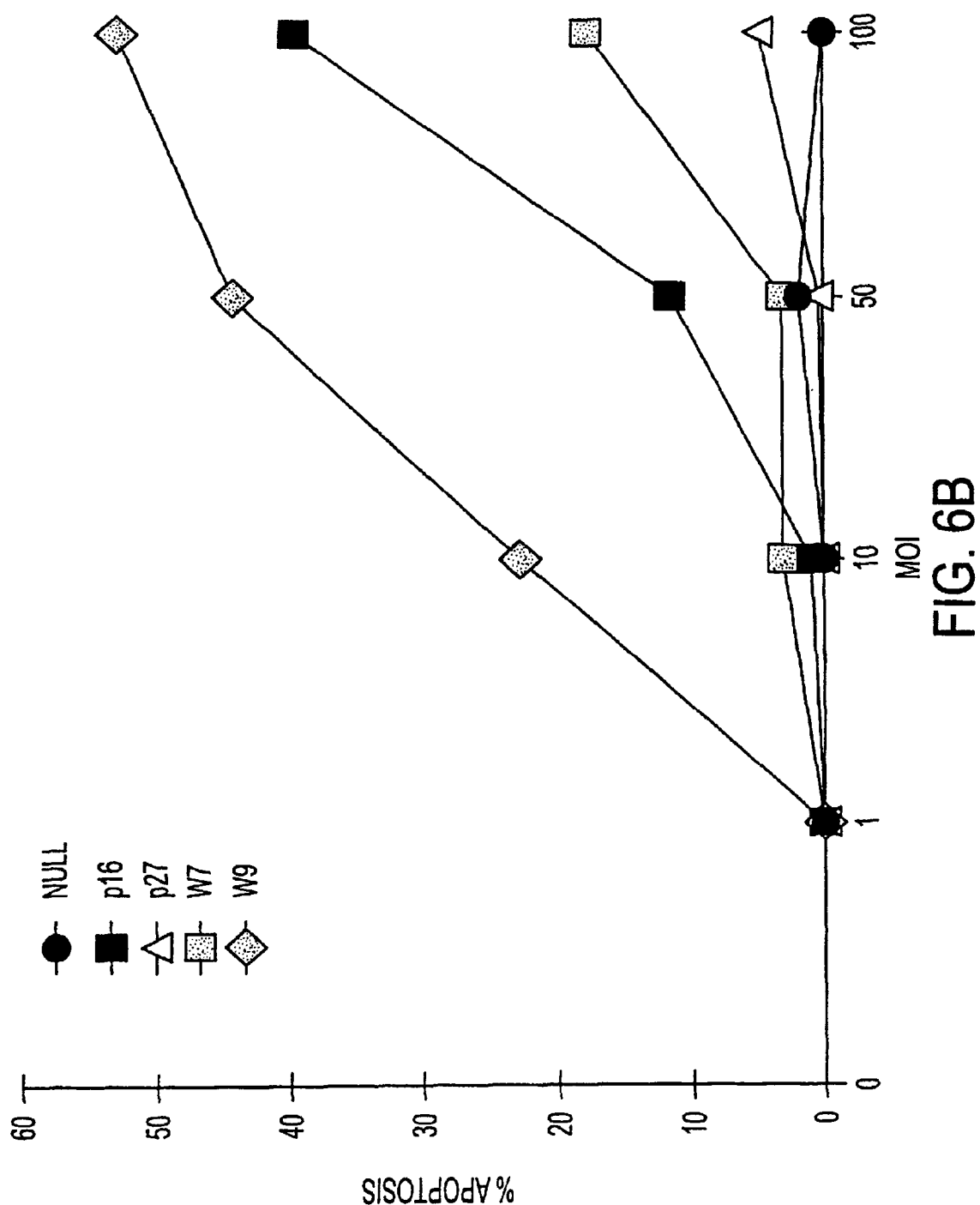
FIG. 6B is representation of a line graph showing that a non-limiting, representative adenovirus of the invention, AV-W9, is more effective than similarly delivered p16, p27, or W7 in inducing apoptosis in SW480 colon carcinoma cells. Apoptosis was measured three days following transduction with the indicated AV-CDKi at equivalent MOI. Shown are the percentage of cells induced to undergo apoptosis following transduction by adenoviruses containing the entire E4 region and encoding p16 (solid squares), p27 (triangles), W7 (hatched squares), W9 (diamonds), or CMV promoter with no insert (Null, circles)
Figure 6C:
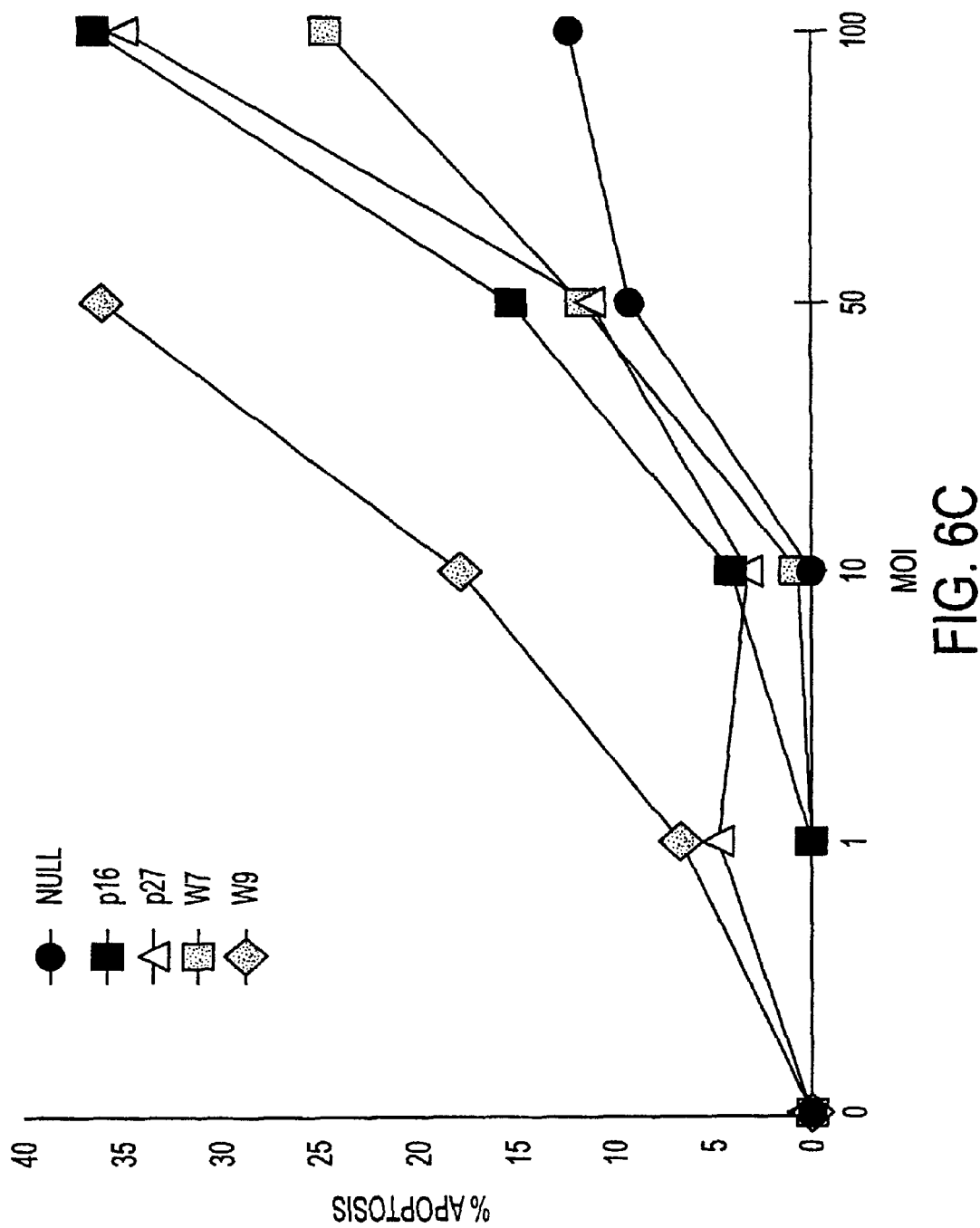
FIG. 6C is a representation of a line graph showing that a non-limiting, representative adenovirus of the invention, AV-W9, is more effective than similarly delivered p16, p27, or W7 in inducing apoptosis in A549 lung carcinoma cells. Apoptosis was measured three days following transduction with the indicated AV-CDKi at equivalent MOI. Shown are the percentage of cells induced to undergo apoptosis following transduction by adenoviruses containing the entire E4 region and encoding p16 (solid squares), p27 (triangles), W7 (hatched squares), W9 (diamonds), or CMV promoter with no insert (Null, circles)

As can be seen in FIG. 6A, AV-W9 was more effective than AV-p16, AV-p27, or AV-W7 in inducing apoptosis in PC3 prostate tumor cells. It should be noted that because the apoptosis data shown in FIG. 6A was measured three days following transduction, at MOI of AV-W9 of greater than 10, fewer apoptotic cells were detected using the TdT TUNEL method because, as assessed by microscope analysis, many of the cells were dead and had started to degrade. FIG. 6B shows that AV-W9 was more effective than AV-p16, AV-p27, or AV-W7 in inducing apoptosis in SW480 colon carcinoma cells. FIG. 6C shows that in A549 lung carcinoma cells, AV-W9 was more effective in inducing apoptosis than AV-p16, AV-p27, or AV-W7.

EXAMPLE VII

Efficacy of AV-W9

To determine whether or not the potent apoptosis-inducing ability of AV-W9 was due to an enhanced level of expression in a cell, adenoviruses having the E4 region and encoding W9 (AV-W9), p16 (AV-p16), p27 (AV-p27), or no insert (AV-Null) were titered. Then DU145 prostate tumor cells were transduced with equivalent amounts of each virus. Following transduction, the levels of expression of each of these recombinant adenoviruses and their abilities to induce apoptosis in DU145 cells were examined. To measure expression, transduced cells were permeabilized, and intracellularly stained with anti-p16 or anti-p27 antibodies (commercially available from Pharmingen). Apoptosis was measured using a TdT TUNEL FACS-based assay according to manufacturer's instructions (Pheonix Flow Systems).

Figure 7A:
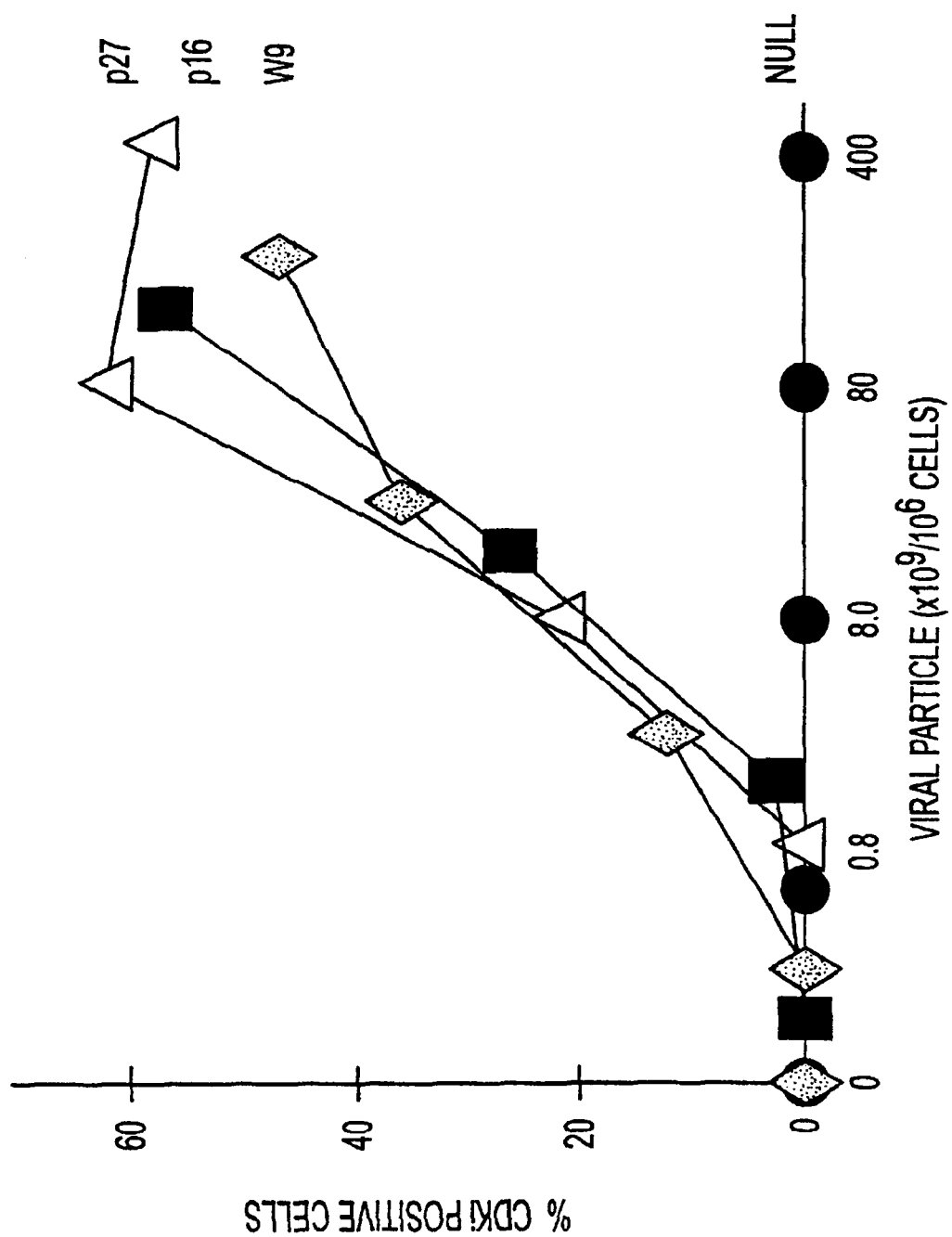
FIG. 7A is a representation of a line graph showing that a non-limiting, representative adenovirus of the invention, AV-W9, is expressed at similar levels in neoplastic cells compared to similarly delivered parental p16 and p27. DU145 prostate tumor cells were transduced with AV-W9 (diamonds), AV-p16 (squares), AV-p27 (triangle) and AV-no insert (Null, circles). After two days, the cells were assessed for expression by intracellular staining with anti-p16 and anti-p27 antibodies.
Figure 7B:
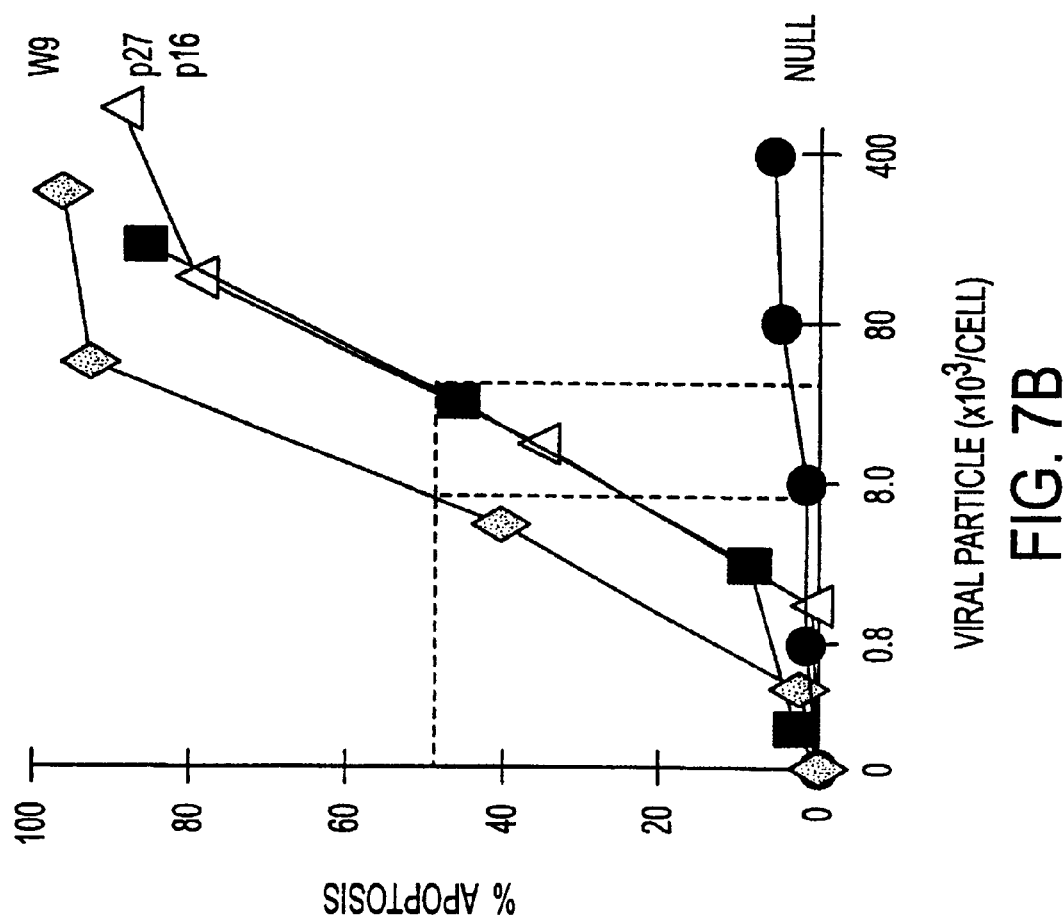
FIG. 7B is a representation of a line graph showing that a non-limiting, representative adenovirus of the invention, AV-W9, is more efficacious at inducing apoptosis in neoplastic cells than similarly delivered parental p16 and p27. The same DU145 prostate tumor cells transduced and assessed for intracellular expression of W9, p16, and p27 from FIG. 7A were also assessed for apoptosis by FACS-based TdT TUNEL assay two days following transduction.

Approximately the same amount of viral units was required to achieve the same level of expression in DU145 cells (FIG. 7A); however, a lower amount of viral units of AV-W9 was required to induce apoptosis in DU145 cells as compared to the parental strains (AV-p16 and AV-p27) (FIG. 7B). In FIGS. 7A and 7B, the same DU145 cells were transduced with AV-W9, AV-p16, and AV-p27. Two days following transduction, the level of apoptosis (FIG. 7B) and the level of expression of the delivered CDKi (FIG. 7A) was assessed. AV-W9 elicited apoptosis required threefold less virus than AV-p16 or AV-p27 demonstrating that AV-W9 is more efficient in eliciting apoptosis than either parental molecule. Thus, AV-W9 at a lower dosage is a more potent inducer of apoptosis than either AV-p16 or AV-p27.

Figure 7C:
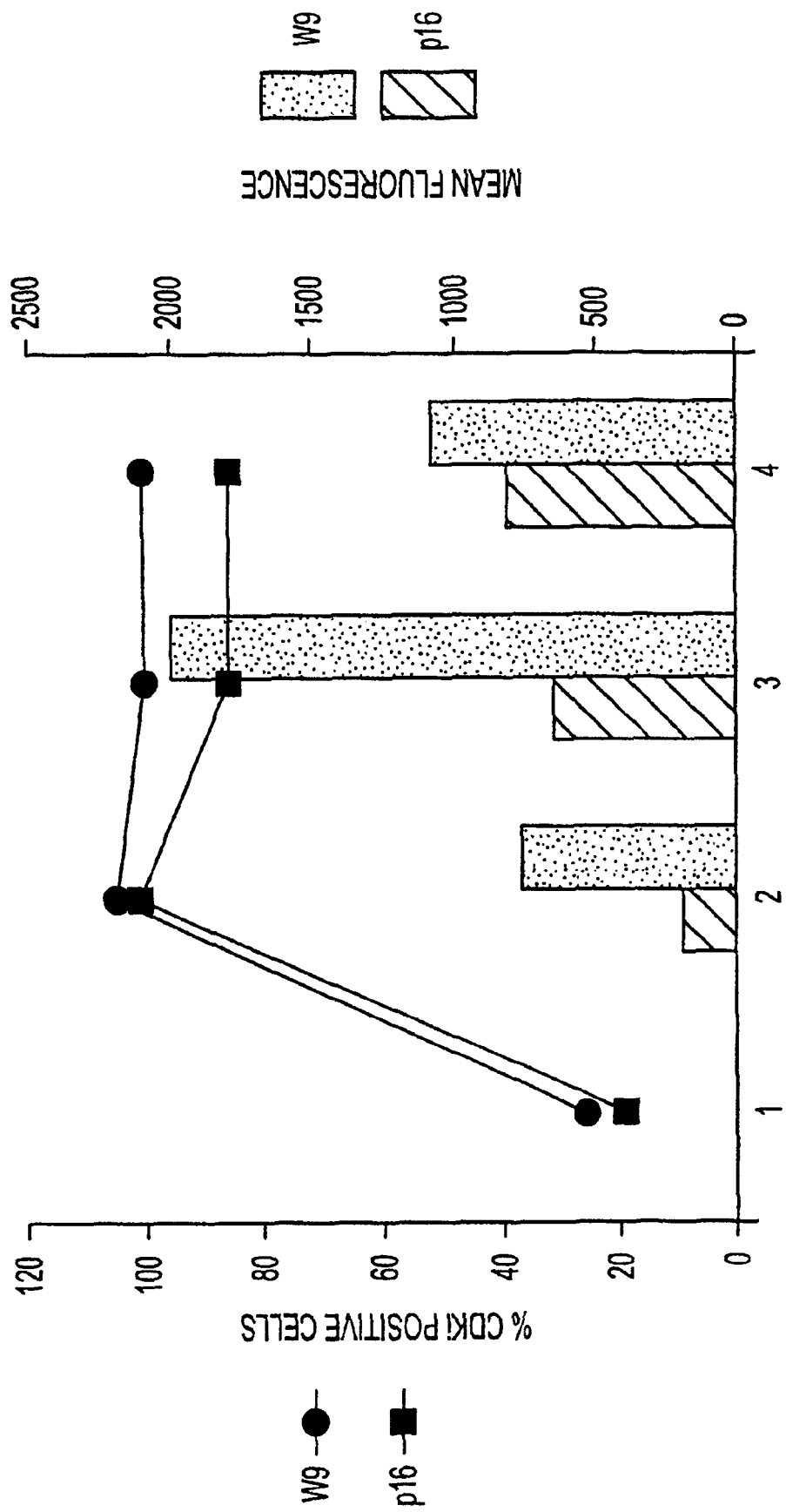
FIG. 7C is a representation of a line/bar graph showing a time course of W9 and p16 expression efficiency and level of expression in AV-W9 and AV-p16 transduced A549 cells, respectively. A549 cells were transduced with equivalent amounts of AV-W9 (circles) or AV-p16 (squares) and assessed for CDKi expression over a period of 4 days using an anti-p16 antibody. The line graph shows the number of transduced cells expressing either W9 or p16, while the bar graph shows the levels of expression of W9 and p16 in the transduced cells.

Expression levels of AV-W9 and AV-p16 were also assessed in A549 lung cells. A549 cells were transduced with equivalent amounts of AV-W9 or AV-p16, and the level of expression was assessed with an anti-p16 antibody (which binds to the C-terminal p16 portion of the W9 fusion protein). As can be seen in FIG. 7C, although 80% of the transduced cells expressed p16 and W9 after 2 days (compare the lines on the graph), the number of W9-expressing cells was significantly higher than p16-expressing cells by day 3, demonstrating that W9 is more stable than the parental p16 molecule. Moreover, the level of expression of W9 in the transduced cells was higher than the level of p16 (compare bars on the graphs). Thus, although AV-W9 and AV-p16 had an equal ability to transduce A549 cells, the expression level of the W9 protein was higher in these cells, indicating that W9 was more stable than p16 in these cells.

EXAMPLE VIII

Tumor Cells Transduced In Vitro with AV-W9 Failed to Form Tumors In Vivo

The tumor-forming ability of human tumor cells transduced in vitro with the AV-CDKi prior to implantation into immunodeficient mice nude mice was also studied. $1 \times 10^6$ A549 lung carcinoma cells or PC3 prostate tumor cells were transduced with 50 million infectious units of adenovirus encoding W9, p16, p27, W7, or no insert (PBS; adenovirus bearing only the CMV promoter, but no insert). The cells were then harvested and washed. Sixteen hours following transduction, the one million pretreated cells were implanted subcutaneously into 6–8 weeks old, BALB/c nude mice of mixed genders (commercially available from Taconic Labs, Germantown, N.Y.). Tumor formation was tracked over a 2–3 month period using calipers.

Figure 8A:
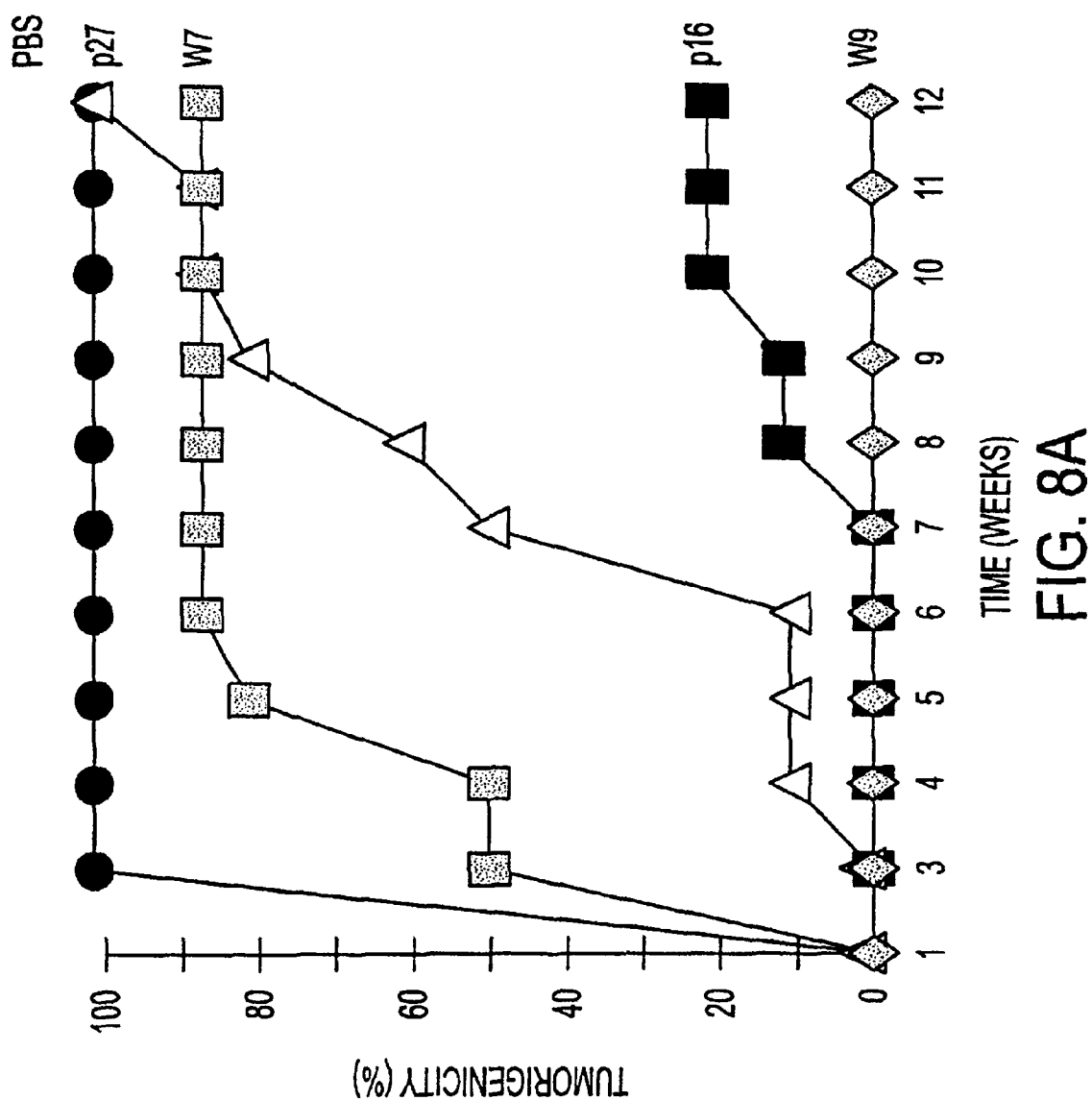
FIG. 8A is a representation of a survival chart showing that a non-limiting, representative adenovirus of the invention, AV-W9, prevented tumor formation in a lung carcinoma xenograft model. $1 \times 10^6$ A549 cells were transduced at a MOI of 50 with AV-no insert (PBS, circles), and the different AV-CDKi (AV-p27, triangles; AV-p16, solid squares; AV-W7, hatched squares; AV-W9, diamonds). The transduced cells were introduced subcutaneously into Balb-nude mice (n=10), and tumor formation was tracked for 12 weeks.
Figure 8B:
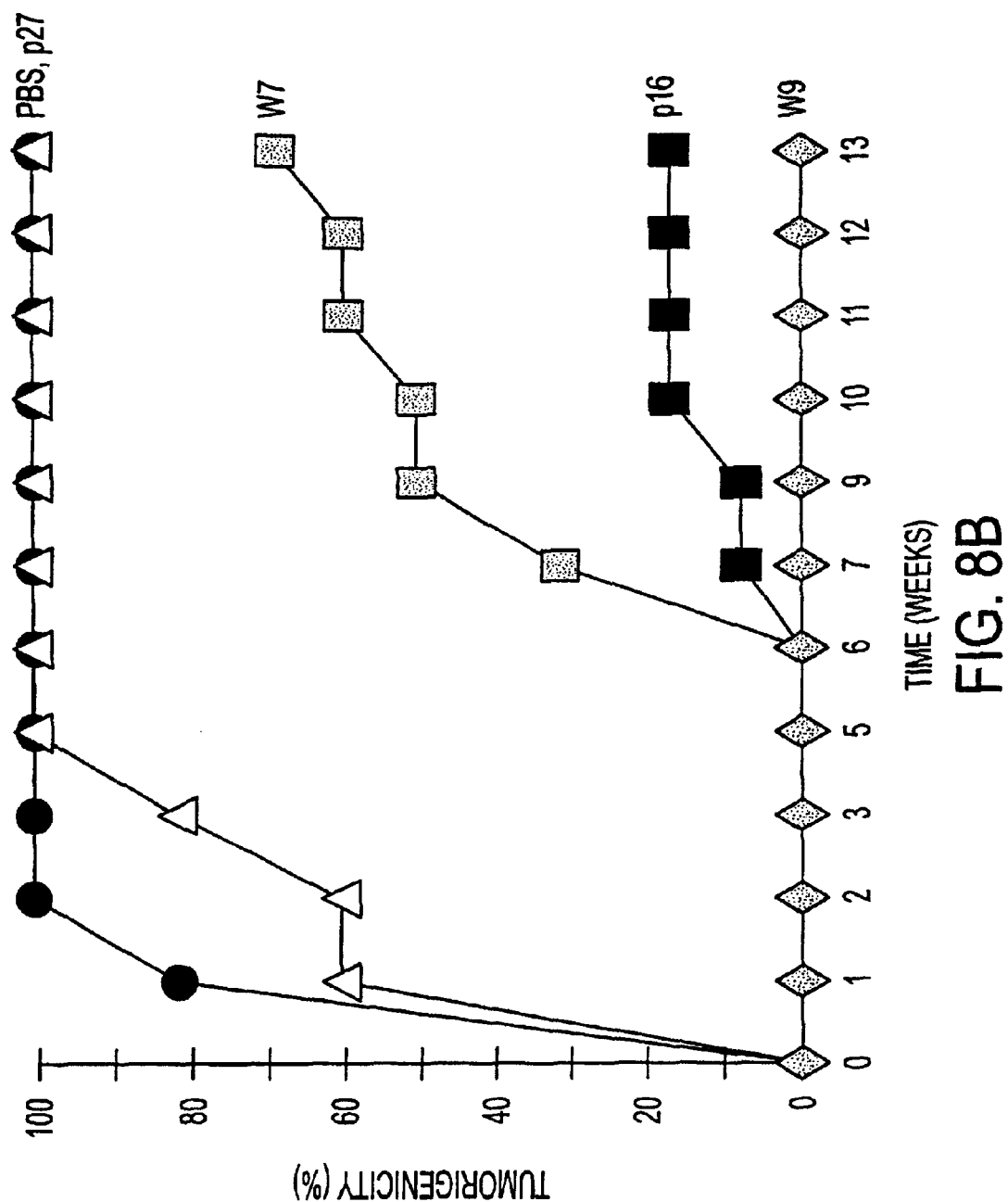
FIG. 8B is a representation of a survival chart showing that a non-limiting, representative adenovirus of the invention, AV-W9, prevented tumor formation in a prostate tumor xenograft model. $1 \times 10^6$ PC3 cells were transduced at a MOI of 50 with AV-no insert (PBS, circles), and the different AV-CDKi (AV-p27, triangles; AV-p16, solid squares; AV-W7, hatched squares; AV-W9, diamonds). The transduced cells were introduced subcutaneously into Balb-nude mice (n=10), and tumor formation was tracked for 13 weeks.

Following implantation, the AV-W9 transduced human tumor cells did not produce tumors while mice that received tumor cells transduced with AV encoding the p27, p16, or an alternative p27-p16 fusion molecule, W7, did develop tumors. Thus, as shown on FIG. 8A, after 12 weeks, no animals developed tumors from A549 cells transduced in vitro with AV-W9. Similarly, following implantation with PC3 cells transduced with AV-W9, no animals developed tumors at 13 weeks (FIG. 8B).

Thus, only W9 delivered by an adenovirus containing the E4 region (AV-W9) completely prevented tumor formation in immunodeficient mice by both PC3 and A549 cells. AV-p16 prevented formation in 80% of the mice, while at least 70% of the mice treated with AV-W7, AV-p27, or AV-null (i.e., PBS) succumbed to tumors (FIGS. 8A and 8B).

EXAMPLE IX

Direct Injection of AV-W9 into Pre-Existing Tumors In Vivo Inhibited Tumor Growth The ability of AV-W9 to inhibit tumor growth was next examined following direct injection into a pre-existing tumor in vivo. To do this, $1 \times 10^6$ DU145 human prostate tumor cells were injected subcutaneously into Balb/c nude mice. Seven to ten days later, established tumors were observed and measured. The tumors measured approximately 40 mm$^3$. The tumors were treated with $1.25 \times 10^{11}$ particles of AV-W9, AV-p16, or no insert (PBS; adenovirus containing the E4 region and bearing the CMV promoter with no insert) introduced intratumorally by direct injection on days 1, 3, and 5 using a programmable pump microsyringe (the KDS 100 infusion pump, KD Scientific, Boston, Mass.) formatted to inject 30 microliters per minute. Tumors were tracked over 2–3 months.

Figure 9:
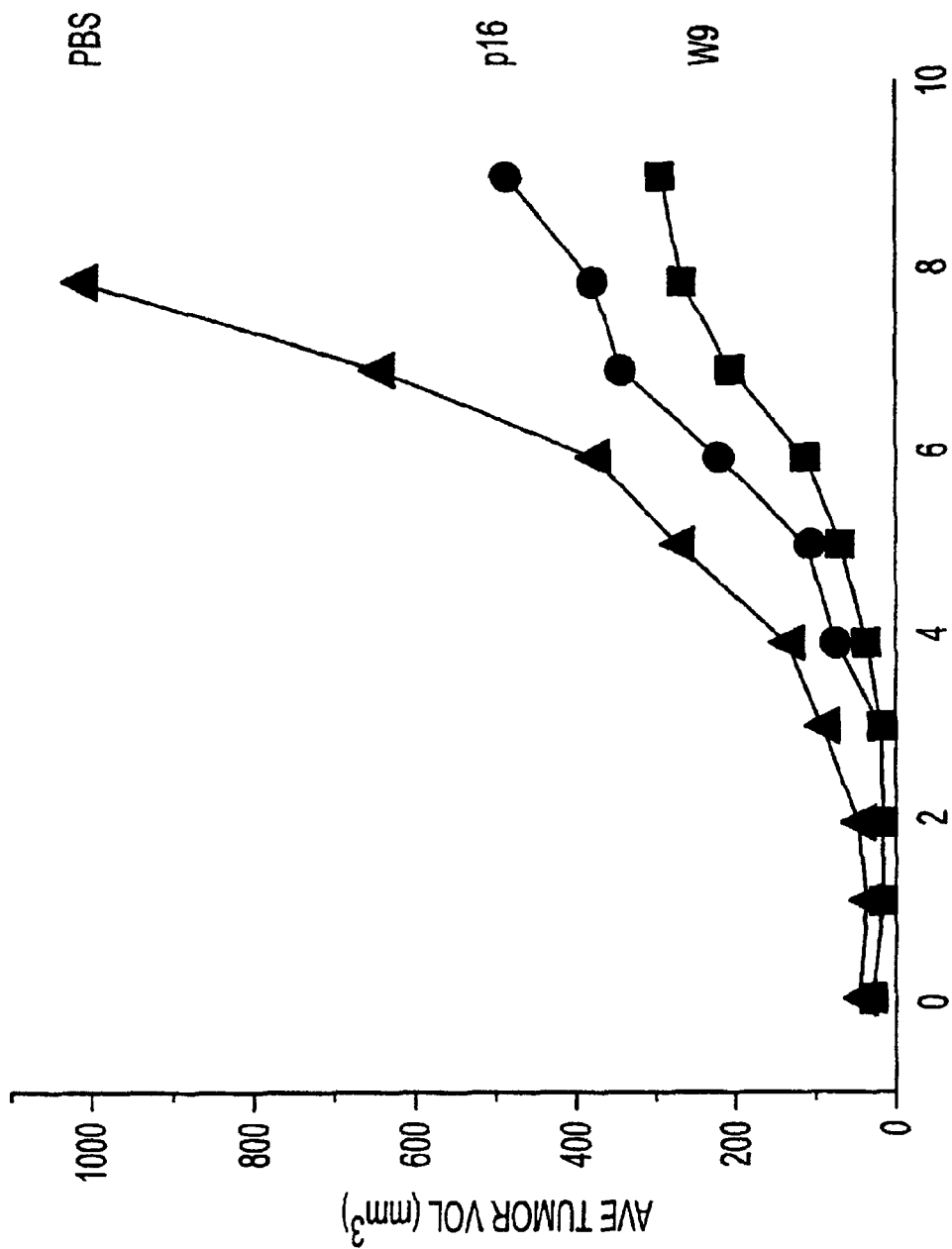
FIG. 9 is a representation of a line graph showing that a non-limiting, representative adenovirus of the invention, AV-W9, slows tumor growth in a prostate xenograft tumor model. Subcutaneous DU145 prostate tumor xenografts (induced using one million cells) were treated with AV-W9, AV-p16, or AV-no insert (PBS) by intratumoral injections at day 1, 3, and 5 using $1.25 \times 10^{11}$ virus particles per injection. The average starting volumes of the tumors was 40 mm$^3$ (n=10). Tumor size was followed for a 10 week period.
Figure 10A:
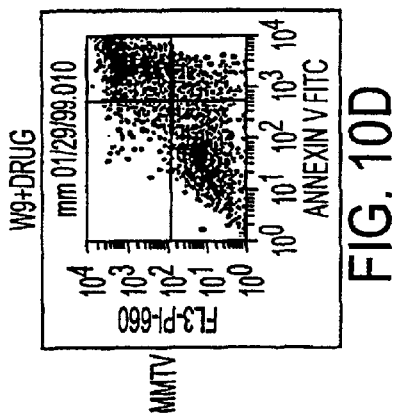
FIGS. 10A–10L are representations of a series of FACS histograms showing the apoptosis-inducing ability of the entire adenovirus E4 region (or just the adenovirus E4orf6 protein alone) expressed with the W9 protein "No drug" indicates untransduced cells with no added drug (negative control); "+drug" indicates untransduced cells with the addition of dexamethasone (to MMTV cells) or IMX (to 293-E4 cells and to 34X cells); "W9" indicates transduction of the cells with an adenovirus lacking an entire E4 region and encoding W9 in the absence of drug; "W9+drug" indicates transduction of the cells with an adenovirus lacking an entire E4 region and encoding W9 in the presence of dexamethasone (MMTV cells) or IMX (293-E4 cells and 34X cells).
Figure 10B:
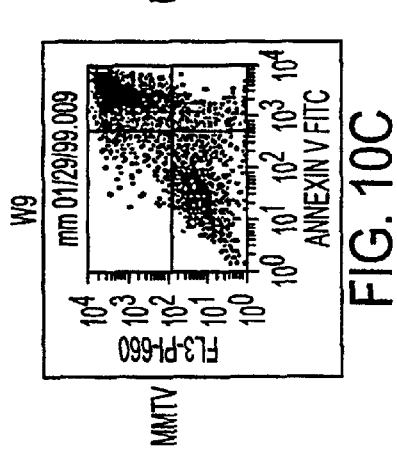
Figure 10C:
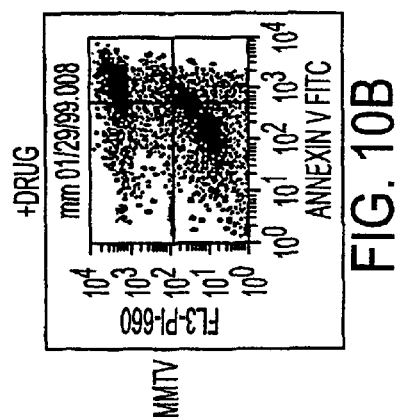
Figure 10D:
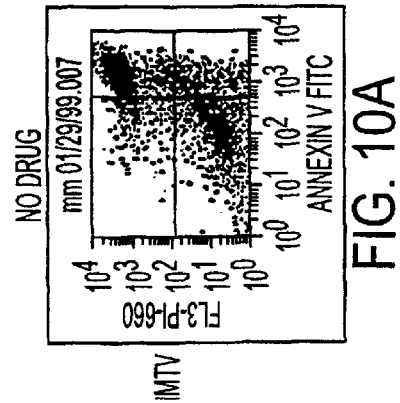
Figure 10E:
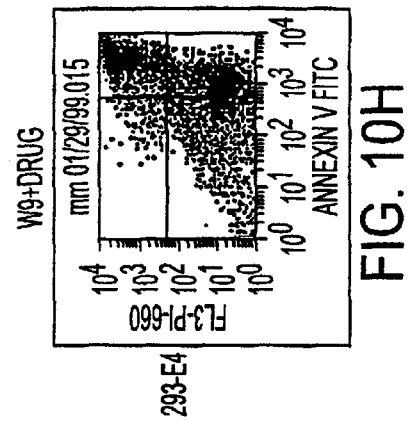
Figure 10F:
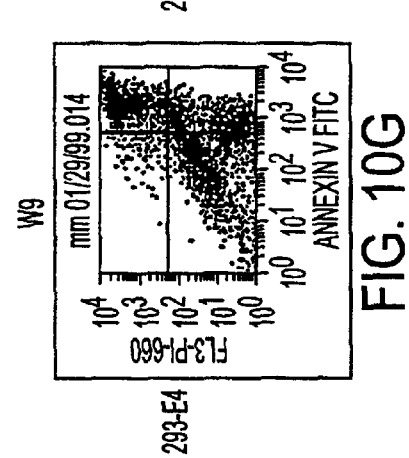
Figure 10G:
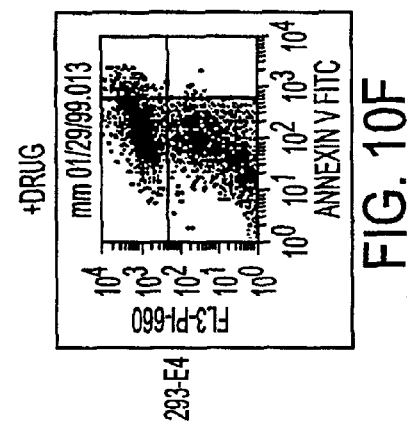
Figure 10H:
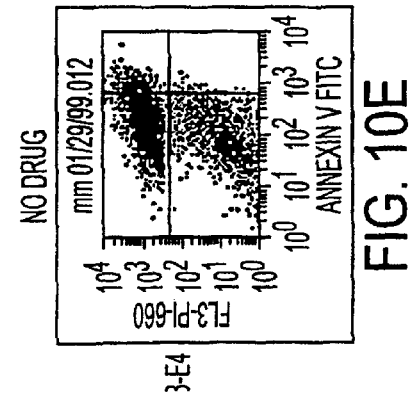
Figure 10I:
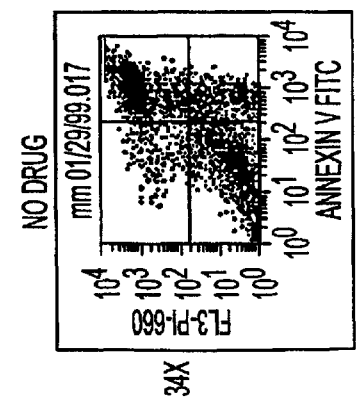
Figure 10J:
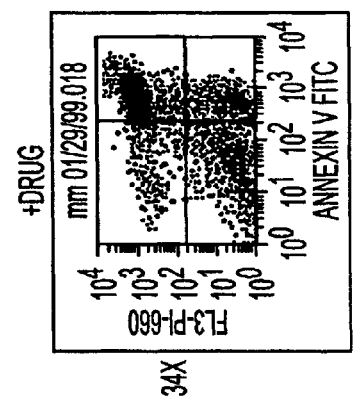
Figure 10K:
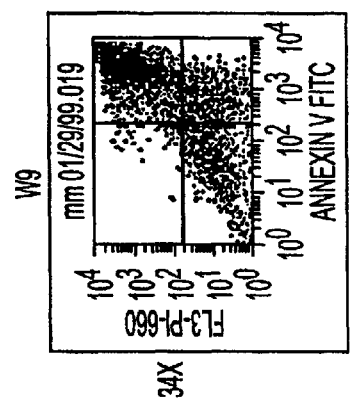
Figure 10L:
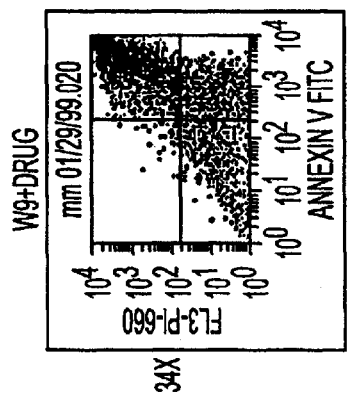

As shown in FIG. 9, delivery of AV-W9 to pre-existing tumors resulted in the regression or suppression of tumor growth, compared to tumors injected with "PBS" (i.e., adenovirus with no insert). Treatment of pre-existing tumors with the AV-p16 was less efficacious.

In a second experiment, twenty animals were implanted with one million A549 tumor cells, and five animals per group were injected with $1.25 \times 10^{11}$ particles of AV-W9, AV-p16, AV-p27, and AV-Null on days 1, 3, and 7. Table III shows the overall results from the ability of injected AV-CDKi to inhibit tumor growth of an existing tumor, where "Complete Response" means a complete remission of the tumor following injection, "Partial Response" means a retardation in the growth of the tumor compared to the Null tumor, and "No Response" means the tumor continued to grow as well as the Null injected tumor.

TABLE III

| AV-CDKi | Complete Response | "Partial" Response | No Response |
|---------|-------------------|--------------------|-------------|
| AV-W9   | 1/5               | 2/5                | 2/5         |
| AV-p16  | 0/5               | 0/5                | 5/5         |
| AV-p27  | 0/5               | 0/5                | 5/5         |
| AV-Null | 0/5               | 0/5                | 5/5         |

Thus, as shown in FIG. 9 and Table III, the AV-W9 anti-neoplastic reagent of the invention was able to inhibit tumor growth following localized administration in vivo, and was superior than either similarly delivered parental molecule (i.e., AV-p16 and AV-p27).

EXAMPLE X

A Recombinant Lentivirus Encoding the W9 Fusion Protein in the Absence of Any Adenovirus E4 Proteins Failed to Induce Apoptosis in Neoplastic Cells A second virus-based delivery vehicle for the W9 fusion protein was generated. Here, a lentivirus vector previously described (see Dull et al. (1998) *J. Virol.* 72: 8463–8471) was used to generate recombinant lentiviruses encoding W9, W7, p16, and p27. Transgenes similar to those described in Example I (i.e., a transgene consisting of CMV enhancer/promoter-CDKi insert-SV40 polyA) were inserted into the lentivirus transfer vector, pRRL.sin-18, between the splice acceptor cite and the 3' LTR (Dull et al., supra). It should be noted, however, that these lentivirus-encoded CDKi did not have the 6 His, HA tag.

The recombinant lentiviruses were packaged essentially as described in Dull et al., supra. The recombinant lentiviruses were used to transduce neoplastic cells according to the methods generally described above for the recombinant adenoviruses. For example, for A549 cells, the cells were seeded at $10^5$ cells/well in a 12 well plate in DMEM$^{high}$ supplemented with 10% FBS. The following day, the media was aspirated, and new media (1 ml/well) was added with or without polybrene at a final concentration of 8pg/ml. The cells were then transduced with an equivalent number of viral particles of lentiviruses encoding W7, W9, p16, or p27. Twenty-four hours following transduction, the media of the cells was changed, and apoptosis was tested forty-eight hours later (i.e., three days post-transduction).

These studies showed that W9 delivered by lentivirus in the absence of any adenovirus E4 region-encoded proteins did not induce apoptosis in neoplastic cells, but did inhibit cell proliferation of these cells (data not shown).

EXAMPLE XI

Adenovirus E4 Region is Required to Facilitate the Apoptosis-Inducing Ability of W9

Because W9 encoded by lentivirus did not induce apoptosis when expressed in neoplastic cells, replicationdefective recombinant adenoviruses encoding W9, but lacking not only the E1 region, but also the E4 region, were generated. The only adenovirus E4 region protein encoded by these E4 region-deleted adenoviruses was the E4orf4 protein, and that was expressed in cells infected with the E4 region-deleted adenoviruses in very low amounts. These recombinant adenoviruses were generated using the methods and cells generally described in McArthur et al., "Adenoviral Delivery of Novel CDK Inhibitors for Preventing Proliferation of Smooth Muscle Cells," U.S. patent application Ser. No. 60/122,974, filed Mar. 1, 1999 (herein incorporated by reference). Because deletion of the adenovirus E4 region is a lethal mutation to adenoviruses, these recombinant adenoviruses were packaged in a cell, 293-E4, that was stably transfected with nucleic acid comprising the entire adenovirus E4 region under the control of the inducible promoter. When this W9-encoding adenovirus, lacking both the E1 region and the E4 region, was used to transduce cells, no induction of apoptosis occurred (FIG. 10, W9). Accordingly, the E4 region of adenovirus, or a protein (or active fragment) encoded thereby, is the region of adenovirus necessary and sufficient to synergize with the W9 protein to produce an anti-neoplastic reagent of the invention. Moreover, since the E4 region-deleted adenovirus expressed small amounts of E4orf4 protein in infected cells, the adenovirus E4 protein necessary and sufficient to synergize with W9 to induce apoptosis in neoplastic cells is not likely to be E4orf4.

To determine the fragment within the adenovirus E4 region that is sufficient to facilitate the apoptosis-inducing ability of W9, an adenovirus lacking both the E1 region and E4 region and encoding W9 was constructed and used to transduce three cell lines: MMTV, a cell which expresses the adenovirus E4orf6 protein under the control of the MMTV promoter, inducible by the drug dexamethasone; 293-E4, a 293 cell which expresses the entire adenovirus E4 region under the control of a promoter, inducible by the drug 3-isobutyl-1-methylxanthine (MX, Catalog No. I-7018, Sigma Chemical Co., St. Louis, Mo.); and 34X, a 293 cell that expresses the adenovirus E4orf6 under the control of a promoter inducible by IMX. In each of these cell lines, some low level of E4 or E4orf6 expression can occur without drug induction due to the leakiness of the MMTV promoter and the IMXA-inducible promoter.

For this study, 1×10$^5$ cells were transduced with lysate from an E1 region-deleted, E4 region-deleted adenovirus containing the W9-encoding nucleic acid sequence operably linked to the CMV promoter. The cells were transduced in the presence (+drug) or absence (no drug) of either IMX or dexamethasone. IMX was prepared as a 45 mM stock solution in water titrated with 10N NaOH drop-wise until dissolved. At the time of transduction of 293-E4 and 34X cells, virus was added in the presence of IMX (final concentration of 0.5 mM). For MMTV cells (293 MMTV orf6), dexamethasone (1000×=3 mM; Catalog No. D-2915, Sigma) was added at the time of infection at a final concentration of 3 µM.

Cells were harvested two days later and analyzed by Annexin/pI double staining to assess the level of apoptosis.

In the absence of transduction with the E1 region-deleted, E4 region-deleted adenovirus encoding W9, 293-E4 cells showed no apoptosis, even with the addition of the drug (FIG. 10, 293-E4). However, when the cells were transduced, apoptosis was seen even in the absence of the drug, which was presumably due to the low level of leaky E4 expression. The level of apoptosis in the transduced cells, however, increased in the presence of the drug, demonstrating that the W9 and the adenovirus E4 proteins synergistically induce apoptosis.

In the case of the adenovirus E4orf6-expressing lines, MMTV and 34X, there were low levels of apoptosis in the absence of transduction of the cells by the E1 region-deleted, E4 region-deleted adenovirus encoding W9. This apoptosis was likely due to the leakiness of the promoters, and the known ability of E4orf6 to elicit apoptosis. However, when the cells were transduced, the level of apoptosis rose, with a dramatic increase in the level of late apoptotic cells (FIG. 10, MMTV and 34X).

Since the cell lines tested are immortalized, they are analogous to neoplastic cells in vivo. These results demonstrate that the adenovirus E4orf6 protein acts synergistically with W9 to induce apoptosis in neoplastic cells.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A nucleic acid composition comprising a first nucleic acid sequence encoding a secretable, internalizable form of a chimeric CDKi protein and a second nucleic acid sequence encoding a secretable, internalizable form of an adenovirus E4 protein,
   wherein the first and second nucleic acid sequences are operably linked to at least one regulatory sequence.

2. The nucleic acid composition of claim 1, wherein the chimeric CDKi protein is a W9 protein.

3. The nucleic acid composition of claim 1, wherein the adenovirus E4 protein is encoded by E4orf6.

4. A composition comprising the nucleic acid composition of claim 1 and a pharmaceutically acceptable carrier.

5. The composition of claim 4, further comprising a delivery system that facilitates the internalization of the composition by a cell.

6. The composition of claim 5, wherein the delivery system is a recombinant virus particle.

7. The composition of claim 6, wherein the recombinant virus particle is selected from the group consisting of an adenovirus, a lentivirus, an adeno-associated virus, a retrovirus, a herpesvirus, and a vaccinia virus.

8. The composition of claim 7, wherein the recombinant virus particle is an adenovirus.

9. A method for treating an animal with a neoplasm, the method comprising administering to the animal a therapeutically effective amount of the composition of claim 4.

10. A method for treating an animal with a neoplasm, comprising introducing the nucleic acid composition of claim 1 into a cell of the animal, wherein the introduced cell secretes the secretable, internalizable form of the chimeric CDKi protein and secretes the secretable, internalizable form of the adenovirus E4 protein.

11. A method for treating an animal with a neoplasm, comprising introducing the nucleic acid composition of claim 2 into a cell of the animal, wherein the introduced cell secretes the secretable, internalizable form of the W9 protein and secretes the secretable, internalizable form of the adenovirus E4 protein.

* * * * *

SEQUENCE LISTING

<160> NUMBER OF SEQ ID NOS: 32

<210> SEQ ID NO 1
<211> LENGTH: 51
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 1
gcggccggtc atatgcacca ccatcaccat cactcaaacg tgcgagtgtc t             51

<210> SEQ ID NO 2
<211> LENGTH: 96

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 2
gccgccggcg tcgactcggc cgaattcgga tccaccccg ccggaaccgc caccccgct    60 gccccgcca cccgtttgac gtcttctgag gccagg                              96

<210> SEQ ID NO 3
<211> LENGTH: 1420
<212> TYPE: DNA
<213> ORGANISM: Homo sapiens

<400> SEQUENCE: 3
catatgcacc accatcacca tcactcaaac gtgcgagtgt ctaacgggag ccctagcctg    60
gagcggatgg acgccaggca ggcggagcac cccaagccct cggcctgcag gaacctcttc   120
ggcccggtgg accacgaaga gttaacccgg gacttggaga agcactgcag agacatggaa   180
gaggcgagcc agcgcaagtg gaatttcgat tttcagaatc acaaacccct agagggcaag   240
tacgagtggc aagaggtgga gaagggcagc ttgcccgagt tctactacag accccgcgg   300 ccccccaaag gtgcctgcaa ggtgccggcg caggagagcc aggatgtcag cgggagccgc   360
ccggcggcgc cttaattgg ggctccggct aactctgagg acacgcattt ggtggaccca    420
aagactgatc cgtcggacag ccagacgggg ttagcggagc aatgcgcagg aataaggaag   480
cgacctgcaa ccgacgattc ttctactcaa acaaaagag ccaacagaac agaagaaaat   540
gtttcagacg gttccccaaa tgccggttct gtggagcaga cgcccaagaa gcctggcctc   600
agaagacgtc aaacgggtgg cggggcagc ggggtggcg gttccggcgg gggtggatcc     660
gaattctgcg gccgcgcgtg cgctcggcgg ctgcggagag gggagagcat gcagcgggcg   720
gcggggagca gcatggagcc ttcggctgac tggctggcca cggccgcggc ccggggtcgg   780
gtagaggagg tgcgggcgct gctggaggcg gtggcgctgc ccaacgcacc gaatagttac   840
ggtcggaggc cgatccaggt catgatgatg ggcagcgccc gagtggcgga gctgctgctg   900
ctccacggcg cggagcccaa ctgcgccgac cccgccactc tcacccgacc cgtgcacgac   960
gctgcccggg agggcttcct ggacacgctg gtggtgctgc accgggccgg ggcgcggctg  1020
gacgtgcgca tgcctggggg ccgtctgccc gtggacctgg ctgaggagct gggccatcgc  1080
gatgtcgcac ggtacctgcg cgcggctgcg ggggcacca gaggcagtaa ccatgcccgc   1140
atagatgccg cggaaggtcc ctcagacatc cccgattgaa agaaccagag aggctctgag  1200
aaacctcggg aaacttagat catcagtcac cgaaggtcct acagggccac aactgccccc   1260
gccacaaccc accccgcttt cgtagttttc atttagaaaa tagagctttt aaaaatgtcc   1320 tgcctttaa cgtagatata agccttcccc cactaccgta aatgtccatt tatatcatt    1380 tttatatatt cttataaaaa tgtaaaaaag aaaactcgag                        1420

<210> SEQ ID NO 4
<211> LENGTH: 391
<212> TYPE: PRT
<213> ORGANISM: Homo sapiens

<400> SEQUENCE: 4

Met His His His His His His Ser Asn Val Arg Val Ser Asn Gly Ser
  1               5                  10                  15
```

-continued

```
Pro Ser Leu Glu Arg Met Asp Ala Arg Gln Ala Glu His Pro Lys Pro
            20                  25                  30
Ser Ala Cys Arg Asn Leu Phe Gly Pro Val Asp His Glu Glu Leu Thr
        35                  40                  45
Arg Asp Leu Glu Lys His Cys Arg Asp Met Glu Glu Ala Ser Gln Arg
    50                  55                  60
Lys Trp Asn Phe Asp Phe Gln Asn His Lys Pro Leu Glu Gly Lys Tyr
65                  70                  75                  80
Glu Trp Gln Glu Val Glu Lys Gly Ser Leu Pro Glu Phe Tyr Tyr Arg
                85                  90                  95
Pro Pro Arg Pro Pro Lys Gly Ala Cys Lys Val Pro Ala Gln Glu Ser
            100                 105                 110
Gln Asp Val Ser Gly Ser Arg Pro Ala Ala Pro Leu Ile Gly Ala Pro
        115                 120                 125
Ala Asn Ser Glu Asp Thr His Leu Val Asp Pro Lys Thr Asp Pro Ser
    130                 135                 140
Asp Ser Gln Thr Gly Leu Ala Glu Gln Cys Ala Gly Ile Arg Lys Arg
145                 150                 155                 160
Pro Ala Thr Asp Asp Ser Ser Thr Gln Asn Lys Arg Ala Asn Arg Thr
                165                 170                 175
Glu Glu Asn Val Ser Asp Gly Ser Pro Asn Ala Gly Ser Val Glu Gln
            180                 185                 190
Thr Pro Lys Lys Pro Gly Leu Arg Arg Arg Gln Thr Gly Gly Gly Gly
        195                 200                 205
Ser Gly Gly Gly Gly Ser Gly Gly Gly Ser Glu Phe Cys Gly Arg
210                 215                 220
Ala Cys Ala Arg Arg Leu Arg Arg Gly Glu Ser Met Gln Arg Ala Ala
225                 230                 235                 240
Gly Ser Ser Met Glu Pro Ser Ala Asp Trp Leu Ala Thr Ala Ala Ala
                245                 250                 255
Arg Gly Arg Val Glu Glu Val Arg Ala Leu Leu Glu Ala Val Ala Leu
            260                 265                 270
Pro Asn Ala Pro Asn Ser Tyr Gly Arg Arg Pro Ile Gln Val Met Met
        275                 280                 285
Met Gly Ser Ala Arg Val Ala Glu Leu Leu Leu Leu His Gly Ala Glu
    290                 295                 300
Pro Asn Cys Ala Asp Pro Ala Thr Leu Thr Arg Pro Val His Asp Ala
305                 310                 315                 320
Ala Arg Glu Gly Phe Leu Asp Thr Leu Val Val Leu His Arg Ala Gly
                325                 330                 335
Ala Arg Leu Asp Val Arg Asp Ala Trp Gly Arg Leu Pro Val Asp Leu
            340                 345                 350
Ala Glu Glu Leu Gly His Arg Asp Val Ala Arg Tyr Leu Arg Ala Ala
        355                 360                 365
Ala Gly Gly Thr Arg Gly Ser Asn His Ala Arg Ile Asp Ala Ala Glu
    370                 375                 380
Gly Pro Ser Asp Ile Pro Asp
385                 390

<210> SEQ ID NO 5
<211> LENGTH: 1121
<212> TYPE: DNA
<213> ORGANISM: Homo sapiens

<400> SEQUENCE: 5
```

-continued

```
gaattcgccg ccaccatggg ataccettat gatgtgccag attatgcctc aaacgtgcga      60
gtgtctaacg gccgcccctag cctggagcgg atggacgcca ggcaggcgga gcaccccaag    120
ccctcggcct gcaggaacct cttcggcccg gtggaccacg aagagttaac ccgggacttg    180
gagaagcact gcagagacat ggaagaggcg agccagcgca agtggaattt cgattttcag    240
aatcacaaac ccctagaggg caagtacgag tggcaagagg tggagaaggg cagcttgccc    300
gagttctact acagaccccc gcggcccccc aaaggtgcct gcaaggtgcc ggcgcaggag    360
agccaggatg tcagcgggag ccgccgcgcg gcgcctttaa ttggggctcc ggctaactct    420
gaggacacgc atttggtgga cccaaagact gatccgtcgg agagccagac ggggttagcg    480
gagcaatgcg caggaataag gaagcgacct gcaaccgacg attcttctac tcaaaacaaa    540
agagccaaca gaacagaaga aaatgtttca gacggttccc caaatgccgg ttctgtggag    600
cagacgccca gaagcctggc ctcagaaga cgtcaaacgg tcgaggatcc ggcggcgggg     660
agcagcatgg agccttcggc tgactggctg ccacggccg cggcccgggg tcgggtagag    720
gaggtgcggg cgctgctgga ggcgggggcg ctgcccaacg caccgaatag ttacggtcgg    780
aggccgatcc aggtcatgat gatgggcagc gcccgagtgg cggagctgct gctgctccac    840
ggcgcggagc ccaactgcgc cgaccccgcc actctcaccc gacccgtgca cgacgctgcc    900
cgggagggct tcctggacac gctggtggtg ctgcaccggg ccggggcgcg gctggacgtg    960
cgcgatgcct ggggccgtct gcccgtggac ctggctgagg agctgggcca tcgcgatgtc   1020
gcacggtacc tgcgcgcggc tgcgggggc accagaggca gtaaccatgc ccgcatagat   1080
gccgcggaag gtccctcaga catccccgat tgagcggccg c                      1121
```

<210> SEQ ID NO 6
<211> LENGTH: 365
<212> TYPE: PRT
<213> ORGANISM: Homo sapiens

<400> SEQUENCE: 6

```
Met Gly Tyr Pro Tyr Asp Val Pro Asp Tyr Ala Ser Asn Val Pro Val
  1               5                  10                  15

Ser Asn Gly Arg Pro Ser Leu Glu Arg Met Asp Ala Arg Gln Ala Glu
             20                  25                  30

His Pro Lys Pro Ser Ala Cys Arg Asn Leu Phe Gly Pro Val Asp His
         35                  40                  45

Glu Glu Leu Thr Arg Asp Leu Glu Lys His Cys Arg Asp Met Glu Glu
     50                  55                  60

Ala Ser Gln Arg Lys Trp Asn Phe Asp Phe Gln Asn His Lys Pro Leu
 65                  70                  75                  80

Glu Gly Lys Tyr Glu Trp Gln Glu Val Glu Lys Gly Ser Leu Pro Glu
                 85                  90                  95

Phe Tyr Tyr Arg Pro Pro Arg Pro Lys Gly Ala Cys Lys Val Pro
            100                 105                 110

Ala Gln Glu Ser Gln Asp Val Ser Gly Ser Arg Pro Ala Ala Pro Leu
        115                 120                 125

Ile Gly Ala Pro Ala Asn Ser Glu Asp Thr His Leu Val Asp Pro Lys
    130                 135                 140

Thr Asp Pro Ser Asp Ser Gln Thr Gly Leu Ala Glu Gln Cys Ala Gly
145                 150                 155                 160

Ile Arg Lys Arg Pro Ala Thr Asp Asp Ser Ser Thr Gln Asn Lys Arg
                165                 170                 175
```

-continued

Ala Asn Arg Thr Glu Glu Asn Val Ser Asp Gly Ser Pro Asn Ala Gly
            180                 185                 190

Ser Val Glu Gln Thr Pro Lys Lys Pro Gly Leu Arg Arg Arg Gln Thr
        195                 200                 205

Val Glu Asp Pro Ala Ala Gly Ser Ser Met Glu Pro Ser Ala Asp Trp
    210                 215                 220

Leu Ala Thr Ala Ala Arg Gly Arg Val Glu Val Arg Ala Leu
225                 230                 235                 240

Leu Glu Ala Gly Ala Leu Pro Asn Ala Pro Asn Ser Tyr Gly Arg Arg
                245                 250                 255

Pro Ile Gln Val Met Met Met Gly Ser Ala Arg Val Ala Glu Leu Leu
            260                 265                 270

Leu Leu His Gly Ala Glu Pro Asn Cys Ala Asp Pro Ala Thr Leu Thr
        275                 280                 285

Arg Pro Val His Asp Ala Ala Arg Glu Gly Phe Leu Asp Thr Leu Val
    290                 295                 300

Val Leu His Arg Ala Gly Ala Arg Leu Asp Val Arg Asp Ala Trp Gly
305                 310                 315                 320

Arg Leu Pro Val Asp Leu Ala Glu Glu Leu Gly His Arg Asp Val Ala
                325                 330                 335

Arg Tyr Leu Arg Ala Ala Ala Gly Gly Thr Arg Gly Ser Asn His Ala
            340                 345                 350

Arg Ile Asp Ala Ala Glu Gly Pro Ser Asp Ile Pro Asp
        355                 360                 365

<210> SEQ ID NO 7
<211> LENGTH: 1143
<212> TYPE: DNA
<213> ORGANISM: Homo sapiens

<400> SEQUENCE: 7
atgggatacc cttatgatgt gccagattat gccgatccgg cggcggggag cagcatggag      60
ccttcggctg actggctggc cacggccgcg gcccgggtc gggtagagga ggtgcgggcg     120
ctgctggagg cggggggcgct gcccaacgca ccgaatagtt acggtcggag gccgatccag    180
gtcatgatga tgggcagcgc ccgagtggcg gagctgctgc tgctccacgg cgcggagccc    240
aactgcgccg accccgccac tctcacccga cccgtgcacg acgctgcccg ggagggcttc    300
ctggacacgc tggtggtgct gcaccgggcc ggggcgcggc tggacgtgcg cgatgcctgg    360
ggccgtctgc ccgtggacct ggctgaggag ctgggccatc gcgatgtcgc acggtacctg    420
cgcgcggctg cggggggcac cagaggcagt aaccatgccc gcatagatgc cgcggaaggt    480
ccctcagaca tccccgatgg tggcgggggc agcgggggtg gcggttccgg cggggtggga    540
tccgtcgagt caaacgtgcg agtgtctaac gggcgcccta gcctgagcg atggacgcc     600 aggcaggcgg agcaccccaa gccctcggcc tgcaggaacc tcttcggccc ggtggaccac    660 gaaagttaa cccgggactt ggagaagcac tgcagagaca tggaagaggc gagccagcgc    720
aagtggaatt cgattttca gaatcacaaa ccctagagg gcaagtacga gtggcaagag    780
gtggagaagg gcagcttgcc cgagttctac tacagacccc gcggccccc caaaggtgcc    840 tgcaaggtgc cggcgcagga gagccaggat gtcagcggga gccgcccggc ggcgccttta    900 attgggctc cggctaactc tgaggacacg catttggtgg acccaaagac tgatccgtcg    960
gacagccaga cggggttagc ggagcaatgc gcaggaataa ggaagcgacc tgcaaccgac   1020

-continued

```
gattcttcta ctcaaaacaa aagagccaac agaacagaag aaaatgtttc agacggttcc   1080
ccaaatgccg gttctgtgga gcagacgccc aagaagcctg gcctcagaag acgtcaaacg   1140
taa                                                                 1143
```

<210> SEQ ID NO 8
<211> LENGTH: 380
<212> TYPE: PRT
<213> ORGANISM: Homo sapiens

<400> SEQUENCE: 8

```
Met Gly Tyr Pro Tyr Asp Val Pro Asp Tyr Ala Asp Pro Ala Ala Gly
 1               5                  10                  15

Ser Ser Met Glu Pro Ser Ala Asp Trp Leu Ala Thr Ala Ala Ala Arg
            20                  25                  30

Gly Arg Val Glu Glu Val Arg Ala Leu Leu Glu Ala Gly Ala Leu Pro
        35                  40                  45

Asn Ala Pro Asn Ser Tyr Gly Arg Arg Pro Ile Gln Val Met Met Met
    50                  55                  60

Gly Ser Ala Arg Val Ala Glu Leu Leu Leu Leu His Gly Ala Glu Pro
65                  70                  75                  80

Asn Cys Ala Asp Pro Ala Thr Leu Thr Arg Pro Val His Asp Ala Ala
                85                  90                  95

Arg Glu Gly Phe Leu Asp Thr Leu Val Val Leu His Arg Ala Gly Ala
            100                 105                 110

Arg Leu Asp Val Arg Asp Ala Trp Gly Arg Leu Pro Val Asp Leu Ala
        115                 120                 125

Glu Glu Leu Gly His Arg Asp Val Ala Arg Tyr Leu Arg Ala Ala Ala
    130                 135                 140

Gly Gly Thr Arg Gly Ser Asn His Ala Arg Ile Asp Ala Ala Glu Gly
145                 150                 155                 160

Pro Ser Asp Ile Pro Asp Gly Gly Gly Ser Gly Gly Gly Gly Gly Ser
                165                 170                 175

Gly Gly Gly Gly Ser Val Glu Ser Asn Val Arg Val Ser Asn Gly Arg
            180                 185                 190

Pro Ser Leu Glu Arg Met Asp Ala Arg Gln Ala Glu His Pro Lys Pro
        195                 200                 205

Ser Ala Cys Arg Asn Leu Phe Gly Pro Val Asp His Glu Glu Leu Thr
    210                 215                 220

Arg Asp Leu Glu Lys His Cys Arg Asp Met Glu Ala Ser Gln Arg
225                 230                 235                 240

Lys Trp Asn Phe Asp Phe Gln Asn His Lys Pro Leu Glu Gly Lys Tyr
                245                 250                 255

Glu Trp Gln Glu Val Glu Lys Gly Ser Leu Pro Glu Phe Tyr Tyr Arg
            260                 265                 270

Pro Pro Arg Pro Pro Lys Gly Ala Cys Lys Val Pro Ala Gln Glu Ser
        275                 280                 285

Gln Asp Val Ser Gly Ser Arg Pro Ala Ala Pro Leu Ile Gly Ala Pro
    290                 295                 300

Ala Asn Ser Glu Asp Thr His Leu Val Asp Pro Lys Thr Asp Pro Ser
305                 310                 315                 320

Asp Ser Gln Thr Gly Leu Ala Glu Gln Cys Ala Gly Ile Arg Lys Arg
                325                 330                 335

Pro Ala Thr Asp Asp Ser Ser Thr Gln Asn Lys Arg Ala Asn Arg Thr
            340                 345                 350
```

```
Glu Glu Asn Val Ser Asp Gly Ser Pro Asn Ala Gly Ser Val Glu Gln
            355                 360                 365

Thr Pro Lys Lys Pro Gly Leu Arg Arg Arg Gln Thr
    370                 375                 380

<210> SEQ ID NO 9
<211> LENGTH: 1098
<212> TYPE: DNA
<213> ORGANISM: Homo sapiens

<400> SEQUENCE: 9
atgggatacc cttatgatgt gccagattat gccgatccgg cggcggggag cagcatggag      60
ccttcggctg actggctggc cacggccgcg gcccggggtc gggtagagga ggtgcgggcg     120
ctgctggagg cgggggcgct gcccaacgca ccgaatagtt acggtcggag gccgatccag     180
gtcatgatga tgggcagcgc ccgagtggcg gagctgctgc tgctccacgg cgcggagccc     240
aactgcgccg accccgccac tctcacccga cccgtgcacg acgctgcccg ggagggcttc     300
ctggacacgg tggtggtgct gcaccgggcc ggggcgcggc tggacgtgcg cgatgcctgg     360
ggccgtctgc ccgtggacct ggctgaggag ctgggccatc gcgatgtcgc acggtacctg     420
cgcgcggctg cgggggggcac cagaggcagt aaccatgccc gcatagatgc gcggaaggt     480 ccctcagaca tccccgatgt cgagtcaaac gtgcgagtgt ctaacgggcg ccctagcctg     540
gagcggatgg acgccaggca ggcggagcac cccaagccct cggcctgcag gaacctcttc     600
ggcccggtgg accacgaaga gttaacccgg gacttggaga agcactgcag agacatggaa     660
gaggcgagcc agcgcaagtg gaatttcgat tttcagaatc acaaaccct agagggcaag     720 tacgagtggc aagaggtgga gaagggcagc ttgcccgagt tctactacag accccgcgg     780 ccccccaaag gtgcctgcaa ggtgccggcg caggagagcc aggatgtcag cgggagccgc     840
ccggcggcgc ctttaattgg ggctccggct aactctgagg acacgcattt ggtggaccca     900
aagactgatc cgtcggacag ccagacgggg ttagcggagc aatgcgcagg aataaggaag     960
cgacctgcaa ccgacgattc ttctactcaa acaaaagag ccaacagaac agaagaaaat    1020
gtttcagacg gttcccaaa tgccggttct gtggagcaga cgcccaagaa gcctggcctc    1080
agaagacgtc aaacgtaa                                                  1098

<210> SEQ ID NO 10
<211> LENGTH: 365
<212> TYPE: PRT
<213> ORGANISM: Homo sapiens

<400> SEQUENCE: 10

Met Gly Tyr Pro Tyr Asp Val Pro Asp Tyr Ala Asp Pro Ala Ala Gly
  1               5                  10                  15

Ser Ser Met Glu Pro Ser Ala Asp Trp Leu Ala Thr Ala Ala Ala Arg
             20                  25                  30

Gly Arg Val Glu Val Arg Ala Leu Leu Glu Ala Gly Ala Leu Pro
         35                  40                  45

Asn Ala Pro Asn Ser Tyr Gly Arg Arg Pro Ile Gln Val Met Met Met
     50                  55                  60

Gly Ser Ala Arg Val Ala Glu Leu Leu Leu Leu His Gly Ala Glu Pro
 65                  70                  75                  80

Asn Cys Ala Asp Pro Ala Thr Leu Thr Arg Pro Val His Asp Ala Ala
                 85                  90                  95
```

```
Arg Glu Gly Phe Leu Asp Thr Leu Val Val Leu His Arg Ala Gly Ala
                100                 105                 110

Arg Leu Asp Val Arg Asp Ala Trp Gly Arg Leu Pro Val Asp Leu Ala
        115                 120                 125

Glu Glu Leu Gly His Arg Asp Val Ala Arg Tyr Leu Arg Ala Ala Ala
130                 135                 140

Gly Gly Thr Arg Gly Ser Asn His Ala Arg Ile Asp Ala Ala Glu Gly
145                 150                 155                 160

Pro Ser Asp Ile Pro Asp Val Glu Ser Asn Val Arg Val Ser Asn Gly
                165                 170                 175

Arg Pro Ser Leu Glu Arg Met Asp Ala Arg Gln Ala Glu His Pro Lys
            180                 185                 190

Pro Ser Ala Cys Arg Asn Leu Phe Gly Pro Val Asp His Glu Glu Leu
        195                 200                 205

Thr Arg Asp Leu Glu Lys His Cys Arg Asp Met Glu Glu Ala Ser Gln
    210                 215                 220

Arg Lys Trp Asn Phe Asp Phe Gln Asn His Lys Pro Leu Glu Gly Lys
225                 230                 235                 240

Tyr Glu Trp Gln Glu Val Lys Gly Ser Leu Pro Glu Phe Tyr Tyr
                245                 250                 255

Arg Pro Pro Arg Pro Lys Gly Ala Cys Lys Val Pro Ala Gln Glu
                260                 265                 270

Ser Gln Asp Val Ser Gly Ser Arg Pro Ala Ala Pro Leu Ile Gly Ala
        275                 280                 285

Pro Ala Asn Ser Glu Asp Thr His Leu Val Asp Pro Lys Thr Asp Pro
290                 295                 300

Ser Asp Ser Gln Thr Gly Leu Ala Glu Gln Cys Ala Gly Ile Arg Lys
305                 310                 315                 320

Arg Pro Ala Thr Asp Asp Ser Ser Thr Gln Asn Lys Arg Ala Asn Arg
                325                 330                 335

Thr Glu Glu Asn Val Ser Asp Gly Ser Pro Asn Ala Gly Ser Val Glu
            340                 345                 350

Gln Thr Pro Lys Lys Pro Gly Leu Arg Arg Arg Gln Thr
                355                 360                 365

<210> SEQ ID NO 11
<211> LENGTH: 557
<212> TYPE: DNA
<213> ORGANISM: Homo sapiens

<400> SEQUENCE: 11
gaattcgccg ccaccatggg ataccttat gatgtgccag attatgccag cctggagcgg      60
atggacgcca ggcaggcgga gcaccccaag ccctcggcct gcaggaacct cttcggcccg     120
gtggaccacg aagagttaac ccgggacttg gagaagcact gcagagacat ggaagaggcg     180
agccagcgca agtggaattt cgattttcag aatcacaaac cctagaggg caagtacgag      240 tgcaagagg tggagaaggg cagcttgccc gagttctact acagaccccc gcggccccc      300 aaaggtgcct gcaaggtgcc ggcgcaggag agccaggatg tcagcgggag ccgcccggcg     360
gcgcctttaa ttgggctcc ggctaactct gaggacacgc atttggtgga cccaaagact      420
gatccgtcgg acagccagac ggggttagcg agcaatgcg caggaataag gaagcgacct      480
gcaaccgacg attcttctac tcaaaacaaa agagccaaca gaacagaaga aaatgtttca     540
gacggttagg cggccgc                                                    557
```

<210> SEQ ID NO 12
<211> LENGTH: 177
<212> TYPE: PRT
<213> ORGANISM: Homo sapiens

<400> SEQUENCE: 12

```
Met Gly Tyr Pro Tyr Asp Val Pro Asp Tyr Ala Ser Leu Glu Arg Met
 1               5                  10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
 50                  55                  60

Gln Asn His Lys Pro Leu Glu Gly Lys Tyr Glu Trp Gln Glu Val Glu
 65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly
```

<210> SEQ ID NO 13
<211> LENGTH: 1073
<212> TYPE: DNA
<213> ORGANISM: Homo sapiens

<400> SEQUENCE: 13

| | | | | |
|---|---|---|---|---|
| gaattcgccg | ccaccatggg | ataccctttat | gatgtgccag | attatgccag cctggagcgg | 60 |
| atggacgcca | ggcaggcgga | gcaccccaag | ccctcggcct | gcaggaacct cttcggcccg | 120 |
| gtggaccacg | aagagttaac | ccgggacttg | agaagcact | gcagagacat ggaagaggcg | 180 |
| agccagcgca | agtggaattt | cgattttcag | aatcacaaac | ccctagaggg caagtacgag | 240 |
| tggcaagagg | tggagaaggg | cagcttgccc | gagttctact | acagaccccc gcggcccccc | 300 |
| aaaggtgcct | gcaaggtgcc | ggcgcaggag | agccaggatg | tcagcgggag ccgcccggcg | 360 |
| gcgcctttaa | ttggggctcc | ggctaactct | gaggacacgc | atttggtgga cccaaagact | 420 |
| gatccgtcgg | acagccagac | ggggttagcg | agcaatgcg | caggaataag gaagcgacct | 480 |
| gcaaccgacg | attcttctac | tcaaaacaaa | agagccaaca | gaacagaaga aaatgtttca | 540 |
| gacggtggtg | gcgggggcag | cggggtggc | ggttccggcg | gggtggatc cgtcgaggat | 600 |
| ccggcggcgg | ggagcagcat | ggagccttcg | gctgactggc | tggccacggc cgcggcccgg | 660 |
| ggtcgggtag | aggaggtgcg | ggcgctgctg | gaggcggggg | cgctgcccaa cgcaccgaat | 720 |
| agttacggtc | ggaggccgat | ccaggtcatg | atgatgggca | cgcccgagt ggcggagctg | 780 |
| ctgctgctcc | acggcgcgga | gcccaactgc | gccgaccccg | ccactctcac ccgacccgtg | 840 |

```
cacgacgctg cccgggaggg cttcctggac acgctggtgg tgctgcaccg ggccggggcg      900
cggctggacg tgcgcgatgc ctggggccgt ctgcccgtgg acctggctga ggagctgggc      960
catcgcgatg tcgcacggta cctgcgcgcg gctgcggggg gcaccagagg cagtaaccat     1020
gcccgcatag atgccgcgga aggtccctca gacatccccg attgagcggc cgc           1073
```

<210> SEQ ID NO 14
<211> LENGTH: 348
<212> TYPE: PRT
<213> ORGANISM: Homo sapiens

<400> SEQUENCE: 14

```
Met Gly Tyr Pro Tyr Asp Val Pro Asp Tyr Ala Ser Leu Glu Arg Met
 1               5                  10                  15

Asp Ala Arg Gln Ala Glu His Pro Lys Pro Ser Ala Cys Arg Asn Leu
             20                  25                  30

Phe Gly Pro Val Asp His Glu Glu Leu Thr Arg Asp Leu Glu Lys His
         35                  40                  45

Cys Arg Asp Met Glu Glu Ala Ser Gln Arg Lys Trp Asn Phe Asp Phe
     50                  55                  60

Gln Asn His Lys Pro Leu Glu Gly Lys Tyr Glu Trp Gln Glu Val Glu
 65                  70                  75                  80

Lys Gly Ser Leu Pro Glu Phe Tyr Tyr Arg Pro Pro Arg Pro Pro Lys
                 85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Gly Gly Gly Gly Ser Gly Gly Gly Ser Gly Gly Gly Gly Gly Ser
            180                 185                 190

Val Glu Asp Pro Ala Ala Gly Ser Ser Met Glu Pro Ser Ala Asp Trp
        195                 200                 205

Leu Ala Thr Ala Ala Ala Arg Gly Arg Val Glu Val Arg Ala Leu
    210                 215                 220

Leu Glu Ala Gly Ala Leu Pro Asn Ala Pro Asn Ser Tyr Gly Arg Arg
225                 230                 235                 240

Pro Ile Gln Val Met Met Met Gly Ser Ala Arg Val Ala Glu Leu Leu
                245                 250                 255

Leu Leu His Gly Ala Glu Pro Asn Cys Ala Asp Pro Ala Thr Leu Thr
            260                 265                 270

Arg Pro Val His Asp Ala Ala Arg Glu Gly Phe Leu Asp Thr Leu Val
        275                 280                 285

Val Leu His Arg Ala Gly Ala Arg Leu Asp Val Arg Asp Ala Trp Gly
    290                 295                 300

Leu Pro Val Asp Leu Ala Glu Glu Leu Gly His Arg Asp Val Ala Arg
305                 310                 315                 320

Tyr Leu Arg Ala Ala Ala Gly Gly Thr Arg Gly Ser Asn His Ala Arg
                325                 330                 335
```

```
Ile Asp Ala Ala Glu Gly Pro Ser Asp Ile Pro Asp
            340                 345
```

<210> SEQ ID NO 15
<211> LENGTH: 1028
<212> TYPE: DNA
<213> ORGANISM: Homo sapiens

<400> SEQUENCE: 15

```
gaattcgccg ccaccatggg ataccttat gatgtgccag attatgccag cctggagcgg    60
atggacgcca ggcaggcgga gcaccccaag ccctcggcct gcaggaacct cttcggcccg   120
gtggaccacg aagagttaac ccgggacttg agaagcact gcagagacat ggaagaggcg   180
agccagcgca agtggaattt cgattttcag aatcacaaac ccctagaggg caagtacgag   240
tggcaagagg tggagaaggg cagcttgccc gagttctact acagaccccc gcggcccccc   300
aaaggtgcct gcaaggtgcc ggcgcaggag agccaggatg tcagcgggag ccgcccggcg   360
gcgcctttaa ttgggctcc ggctaactct gaggacacgc atttggtgga cccaaagact   420
gatccgtcgg acagccagac ggggttagcg agcaatgcg caggaataag gaagcgacct   480
gcaaccgacg attcttctac tcaaaacaaa agagccaaca gaacagaaga aaatgtttca   540
gacggtgtcg aggatccggc ggcggggagc agcatggagc cttcggctga ctggctggcc   600
acggccgcgg cccggggtcg ggtagaggag gtgcgggcgc tgctggaggc ggggcgctg   660
cccaacgcac cgaatagtta cggtcggagg ccgatccagg tcatgatgat gggcagcgcc   720
cgagtggcgg agctgctgct gctccacggc gcggagccca actgcgccga ccccgccact   780
ctcacccgac ccgtgcacga cgctgcccgg gagggcttcc tggacacgct ggtggtgctg   840
caccgggccg gggcgcggct ggacgtgcgc gatgcctggg gccgtctgcc cgtggacctg   900
gctgaggagc tgggccatcg cgatgtcgca cggtacctgc gcgcggctgc ggggggcacc   960
agaggcagta accatgcccg catagatgcc gcggaaggtc cctcagacat ccccgattga  1020
gcggccgc                                                         1028
```

<210> SEQ ID NO 16
<211> LENGTH: 334
<212> TYPE: PRT
<213> ORGANISM: Homo sapiens

<400> SEQUENCE: 16

```
Met Gly Tyr Pro Tyr Asp Val Pro Asp Tyr Ala Ser Leu Glu Arg Met
  1               5                  10                  15
Asp Ala Arg Gln Ala Glu His Pro Lys Pro Ser Ala Cys Arg Asn Leu
                 20                  25                  30
Phe Gly Pro Val Asp His Glu Glu Leu Thr Arg Asp Leu Glu Lys His
             35                  40                  45
Cys Arg Asp Met Glu Glu Ala Ser Gln Arg Lys Trp Asn Phe Asp Phe
         50                  55                  60
Gln Asn His Lys Pro Leu Glu Gly Lys Tyr Glu Trp Gln Glu Val
 65                  70                  75                  80
Lys Gly Ser Leu Pro Glu Phe Tyr Tyr Arg Pro Pro Arg Pro Lys
                 85                  90                  95
Gly Ala Cys Lys Val Pro Ala Gln Glu Ser Gln Asp Val Ser Gly Ser
                100                 105                 110
Arg Pro Ala Ala Pro Leu Ile Gly Ala Pro Ala Asn Ser Glu Asp Thr
            115                 120                 125
```

```
His Leu Val Asp Pro Lys Thr Asp Pro Ser Asp Ser Gln Thr Gly Leu
        130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Asn Val Ser Asp
                165                 170                 175

Gly Val Glu Asp Pro Ala Ala Gly Ser Ser Met Glu Pro Ser Ala Asp
                180                 185                 190

Trp Leu Ala Thr Ala Ala Arg Gly Arg Val Glu Val Arg Ala
                195                 200                 205

Leu Leu Glu Ala Gly Ala Leu Pro Asn Ala Pro Asn Ser Tyr Gly Arg
        210                 215                 220

Arg Pro Ile Gln Val Met Met Met Gly Ser Ala Arg Val Ala Glu Leu
225                 230                 235                 240

Leu Leu His Gly Ala Glu Pro Asn Cys Ala Asp Pro Ala Thr Leu
                245                 250                 255

Thr Arg Pro Val His Asp Ala Ala Arg Glu Gly Phe Leu Asp Thr Leu
                260                 265                 270

Val Val Leu His Arg Ala Gly Ala Arg Leu Asp Val Arg Asp Ala Trp
                275                 280                 285

Gly Arg Leu Pro Val Asp Leu Ala Glu Glu Leu Gly His Arg Asp Val
                290                 295                 300

Ala Arg Tyr Leu Arg Ala Ala Ala Gly Gly Thr Arg Gly Ser Asn His
305                 310                 315                 320

Ala Arg Ile Asp Ala Ala Glu Gly Pro Ser Asp Ile Pro Asp
                325                 330

<210> SEQ ID NO 17
<211> LENGTH: 266
<212> TYPE: DNA
<213> ORGANISM: Homo sapiens

<400> SEQUENCE: 17
gaattcgccg ccaccatggg ataccttat gatgtgccag attatgccaa gccctcggcc    60
tgcaggaacc tcttcggccc ggtggaccac gaagagttaa cccgggactt ggagaagcac   120
tgcagagaca tggaagaggc gagccagcgc aagtggaatt tcgattttca gaatcacaaa   180 ccctagagg gcaagtacga gtggcaagag gtggagaagg gcagcttgcc cgagttctac    240
tacagacccc cgcggtaggc ggccgc                                        266

<210> SEQ ID NO 18
<211> LENGTH: 80
<212> TYPE: PRT
<213> ORGANISM: Homo sapiens

<400> SEQUENCE: 18

Met Gly Tyr Pro Tyr Asp Val Pro Asp Tyr Ala Lys Pro Ser Ala Cys
1               5                   10                  15

Arg Asn Leu Phe Gly Pro Val Asp His Glu Glu Leu Thr Arg Asp Leu
                20                  25                  30

Glu Lys His Cys Arg Asp Met Glu Glu Ala Ser Gln Arg Lys Trp Asn
            35                  40                  45

Phe Asp Phe Gln Asn His Lys Pro Leu Glu Gly Lys Tyr Glu Trp Gln
        50                  55                  60

Glu Val Glu Lys Gly Ser Leu Pro Glu Phe Tyr Tyr Arg Pro Pro Arg
65                  70                  75                  80
```

<210> SEQ ID NO 19
<211> LENGTH: 737
<212> TYPE: DNA
<213> ORGANISM: Homo sapiens

<400> SEQUENCE: 19

```
gaattcgccg ccaccatggg ataccottat gatgtgccag attatgccaa gccctcggcc      60
tgcaggaacc tcttcggccc ggtggaccac gaagagttaa cccgggactt ggagaagcac     120
tgcagagaca tggaagaggc gagccagcgc aagtggaatt cgattttca gaatcacaaa     180
ccctagagg gcaagtacga gtggcaagag gtggagaagg gcagcttgcc cgagttctac     240
tacagacccc cgcgggtcga ggatccggcg gcggggagca gcatggagcc ttcggctgac     300
tggctggcca cggccgcggc ccggggtcgg gtagaggagg tgcgggcgct gctggaggcg     360
ggggcgctgc ccaacgcacc gaatagttac ggtcggaggc cgatccaggt catgatgatg     420
ggcagcgccc gagtggcgga gctgctgctg ctccacggcg cggagcccaa ctgcgccgac     480
cccgccactc tcacccgacc cgtgcacgac gctgcccggg agggcttcct ggacacgcta     540
gtggtgctgc accgggccgg ggcgcggctg acgtgcgcg atgcctgggg ccgtctgccc     600
gtggacctgg ctgaggagct gggccatcgc gatgtcgcac ggtacctgcg cgcggctgcg     660
gggggcacca gaggcagtaa ccatgcccgc atagatgccg cggaaggtcc ctcagacatc     720
cccgattgag cggccgc                                                    737
```

<210> SEQ ID NO 20
<211> LENGTH: 237
<212> TYPE: PRT
<213> ORGANISM: Homo sapiens

<400> SEQUENCE: 20

```
Met Gly Tyr Pro Tyr Asp Val Pro Asp Tyr Ala Lys Pro Ser Ala Cys
 1               5                  10                  15

Arg Asn Leu Phe Gly Pro Val Asp His Glu Glu Leu Thr Arg Asp Leu
            20                  25                  30

Glu Lys His Cys Arg Asp Met Glu Glu Ala Ser Gln Arg Lys Trp Asn
        35                  40                  45

Phe Asp Phe Gln Asn His Lys Pro Leu Glu Gly Lys Tyr Glu Trp Gln
    50                  55                  60

Glu Val Glu Lys Gly Ser Leu Pro Glu Phe Tyr Tyr Arg Pro Pro Arg
65                  70                  75                  80

Val Glu Asp Pro Ala Ala Gly Ser Ser Met Glu Pro Ser Ala Asp Trp
                85                  90                  95

Leu Ala Thr Ala Ala Ala Arg Gly Arg Val Glu Glu Val Arg Ala Leu
            100                 105                 110

Leu Glu Ala Gly Ala Leu Pro Asn Ala Pro Asn Ser Tyr Gly Arg Arg
        115                 120                 125

Pro Ile Gln Val Met Met Met Gly Ser Ala Arg Val Ala Glu Leu Leu
    130                 135                 140

Leu Leu His Gly Ala Glu Pro Asn Cys Ala Asp Pro Ala Thr Leu Thr
145                 150                 155                 160

Arg Pro Val His Asp Ala Ala Arg Glu Gly Phe Leu Asp Thr Leu Val
                165                 170                 175

Val Leu His Arg Ala Gly Ala Arg Leu Asp Val Arg Asp Ala Trp Gly
            180                 185                 190
```

```
Arg Leu Pro Val Asp Leu Ala Glu Glu Leu Gly His Arg Asp Val Ala
        195                 200                 205

Arg Tyr Leu Arg Ala Ala Gly Gly Thr Arg Gly Ser Asn His Ala
    210                 215                 220

Arg Ile Asp Ala Ala Glu Gly Pro Ser Asp Ile Pro Asp
225                 230                 235
```

<210> SEQ ID NO 21
<211> LENGTH: 782
<212> TYPE: DNA
<213> ORGANISM: Homo sapiens

<400> SEQUENCE: 21

```
gaattcgccg ccaccatggg atacccttat gatgtgccag attatgccaa gccctcggcc      60
tgcaggaacc tcttcggccc ggtggaccac gaagagttaa cccgggactt ggagaagcac     120
tgcagagaca tggaagaggc gagccagcgc aagtggaatt tcgattttca gaatcacaaa     180
cccctagagg gcaagtacga gtggcaagag gtggagaagg gcagcttgcc cgagttctac     240
tacagacccc gcggggtggc gggggcagcg ggggtggcg gttccggcgg gggtggatcc      300
gtcgaggatc cggcggcggg gagcagcatg gagccttcgg ctgactggct ggccacggcc     360
gcggcccggg gtcgggtaga ggaggtgcgc gcgctgctgg aggcggggc gctgcccaac     420
gcaccgaata gttacggtcg gaggccgatc caggtcatga tgatgggcag cgcccgagtg     480
gcggagctgc tgctgctcca cggcgcggag cccaactgcg ccgaccccgc cactctcacc     540
cgacccgtgc acgacgctgc ccgggagggc ttcctggaca cgctggtggt gctgcaccgg     600
gccggggcgc ggctggacgt cgcgatgcc tggggccgtc tgcccgtgga cctggctgag     660
gagctgggcc atcgcgatgt cgcacggtac ctgcgcgcgg ctgcgggggg caccagaggc     720
agtaaccatg cccgcataga tgccgcggaa ggtccctcag acatccccga ttgagcggcc     780
gc                                                                    782
```

<210> SEQ ID NO 22
<211> LENGTH: 252
<212> TYPE: PRT
<213> ORGANISM: Homo sapiens

<400> SEQUENCE: 22

```
Met Gly Tyr Pro Tyr Asp Val Pro Asp Tyr Ala Lys Pro Ser Ala Cys
1               5                   10                  15

Arg Asn Leu Phe Gly Pro Val Asp His Glu Glu Leu Thr Arg Asp Leu
            20                  25                  30

Glu Lys His Cys Arg Asp Met Glu Glu Ala Ser Gln Arg Lys Trp Asn
        35                  40                  45

Phe Asp Phe Gln Asn His Lys Pro Leu Glu Gly Lys Tyr Glu Trp Gln
    50                  55                  60

Glu Val Glu Lys Gly Ser Leu Pro Glu Phe Tyr Tyr Arg Pro Pro Arg
65                  70                  75                  80

Gly Gly Gly Gly Ser Gly Gly Gly Gly Gly Gly Ser Val
                85                  90                  95

Glu Asp Pro Ala Ala Gly Ser Ser Met Glu Pro Ser Ala Asp Trp Leu
            100                 105                 110

Ala Thr Ala Ala Ala Arg Gly Arg Val Glu Glu Val Arg Ala Leu Leu
        115                 120                 125

Glu Ala Gly Ala Leu Pro Asn Ala Pro Asn Ser Tyr Gly Arg Arg Pro
    130                 135                 140
```

-continued

```
Ile Gln Val Met Met Met Gly Ser Ala Arg Val Ala Glu Leu Leu Leu
145                 150                 155                 160

Leu His Gly Ala Glu Pro Asn Cys Ala Asp Pro Ala Thr Leu Thr Arg
                165                 170                 175

Pro Val His Asp Ala Ala Arg Glu Gly Phe Leu Asp Thr Leu Val Val
            180                 185                 190

Leu His Arg Ala Gly Ala Arg Leu Asp Val Arg Asp Ala Trp Gly Arg
        195                 200                 205

Leu Pro Val Asp Leu Ala Glu Glu Leu Gly His Arg Asp Val Ala Arg
    210                 215                 220

Tyr Leu Arg Ala Ala Gly Gly Thr Arg Gly Ser Asn His Ala Arg
225                 230                 235                 240

Ile Asp Ala Ala Glu Gly Pro Ser Asp Ile Pro Asp
                245                 250
```

<210> SEQ ID NO 23
<211> LENGTH: 687
<212> TYPE: DNA
<213> ORGANISM: Homo sapiens

<400> SEQUENCE: 23

```
atggccaagc cctcggcctg caggaacctc ttcggcccgg tggaccacga agagttaacc      60
cgggacttgg agaagcactg cagagacatg gaagaggcga gccagcgcaa gtggaatttc     120
gattttcaga tcacaaaacc cctagagggc aagtacgagt ggcaagaggt ggagaagggc     180
agcttgcccg agttctacta cagacccccg cgggtcgagg atccggcggc ggggagcagc     240
atggagcctt cggctgactg gctggccacg gccgcggccc gggtcgggt agaggaggtg      300
cgggcgctgc tggaggcggg ggcgctgccc aacgcaccga atagttacgg tcggaggccg     360
atccaggtca tgatgatggg cagcgcccga gtggcggagc tgctgctgct ccacggcgcg     420
gagcccaact gcgccgaccc cgccactctc acccgacccg tgcacgacgc tgcccgggag     480
ggcttcctgg acacgctggt ggtgctgcac cgggccgggg cgcggctgga cgtgcgcgat     540
gcctggggcc gtctgcccgt ggacctggct gaggagctgg ccatcgcga tgtcgcacgg      600
tacctgcgcg cggctgcggg gggcaccaga ggcagtaacc atgcccgcat agatgccgcg     660
gaaggtccct cagacatccc cgattga                                         687
```

<210> SEQ ID NO 24
<211> LENGTH: 228
<212> TYPE: PRT
<213> ORGANISM: Homo sapiens

<400> SEQUENCE: 24

```
Met Ala Lys Pro Ser Ala Cys Arg Asn Leu Phe Gly Pro Val Asp His
1               5                   10                  15

Glu Glu Leu Thr Arg Asp Leu Glu Lys His Cys Arg Asp Met Glu Glu
            20                  25                  30

Ala Ser Gln Arg Lys Trp Asn Phe Asp Phe Gln Asn His Lys Pro Leu
        35                  40                  45

Glu Gly Lys Tyr Glu Trp Gln Glu Val Glu Lys Gly Ser Leu Pro Glu
    50                  55                  60

Phe Tyr Tyr Arg Pro Pro Arg Val Glu Asp Pro Ala Ala Gly Ser Ser
65                  70                  75                  80

Met Glu Pro Ser Ala Asp Trp Leu Ala Thr Ala Ala Ala Arg Gly Arg
                85                  90                  95
```

```
Val Glu Glu Val Arg Ala Leu Leu Glu Ala Gly Ala Leu Pro Asn Ala
            100                 105                 110

Pro Asn Ser Tyr Gly Arg Arg Pro Ile Gln Val Met Met Met Gly Ser
        115                 120                 125

Ala Arg Val Ala Glu Leu Leu Leu His Gly Ala Glu Pro Asn Cys
    130                 135                 140

Ala Asp Pro Ala Thr Leu Thr Arg Pro Val His Asp Ala Ala Arg Glu
145                 150                 155                 160

Gly Phe Leu Asp Thr Leu Val Val Leu His Arg Ala Gly Ala Arg Leu
                165                 170                 175

Asp Val Arg Asp Ala Trp Gly Arg Leu Pro Val Asp Leu Ala Glu Glu
            180                 185                 190

Leu Gly His Arg Asp Val Ala Arg Tyr Leu Arg Ala Ala Gly Gly
        195                 200                 205

Thr Arg Gly Ser Asn His Ala Arg Ile Asp Ala Ala Glu Gly Pro Ser
    210                 215                 220

Asp Ile Pro Asp
225
```

<210> SEQ ID NO 25
<211> LENGTH: 597
<212> TYPE: DNA
<213> ORGANISM: Homo sapiens

<400> SEQUENCE: 25

```
atgtcaaacg tgcgagtgtc taacgggagc cctagcctgg agcggatgga cgccaggcag    60
gcggagcacc ccaagccctc ggcctgcagg aacctcttcg gccggtgga ccacgaagag    120
ttaacccggg acttggagaa gcactgcaga gacatggaag aggcgagcca gcgcaagtgg    180
aatttcgatt tcagaatca caaacccta gagggcaagt acgagtggca agaggtggag    240
aagggcagct tgcccgagtt ctactacaga ccccgcggc ccccaaagg tgcctgcaag    300
gtgccggcgc aggagagcca ggatgtcagc gggagccgcc cggcggcgcc tttaattggg    360
gctccggcta actctgagga cacgcatttg gtggacccaa agactgatcc gtcggacagc    420
cagacgggt agcggagca atgcgcagga ataaggaagc gacctgcaac cgacgattct    480
tctactcaaa acaaaagagc caacagaaca gaagaaaatg tttcagacgg ttccccaaat    540
gccggttctg tggagcagac gcccaagaag cctggcctca agacgtca aacgtaa       597
```

<210> SEQ ID NO 26
<211> LENGTH: 198
<212> TYPE: PRT
<213> ORGANISM: Homo sapiens

<400> SEQUENCE: 26

```
Met Ser Asn Val Arg Val Ser Asn Gly Ser Pro Ser Leu Glu Arg Met
 1               5                  10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80
```

```
Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
                180                 185                 190

Leu Arg Arg Arg Gln Thr
            195
```

<210> SEQ ID NO 27
<211> LENGTH: 987
<212> TYPE: DNA
<213> ORGANISM: Homo sapiens

<400> SEQUENCE: 27

```
cggagagggg gagaacagac aacgggcggc ggggagcagc atggagccgg cggcggggag    60
cagcatggag ccttcggctg actggctggc acggccgcg gccgggtc gggtagagga      120
ggtgcgggcg ctgctggagg cggggcgct gcccaacgca ccgaatagtt acggtcggag    180
gccgatccag gtcatgatga tgggcagcgc ccgagtggcg gagctgctgc tgctccacgg    240
cgcggagccc aactgcgccg accccgccac tctcacccga cccgtgcacg acgctgcccg    300
ggagggcttc ctggacacgc tggtggtgct gcaccgggcc ggggcgcggc tggacgtgcg    360
cgatgcctgg ggccgtctgc ccgtggacct ggctgaggag ctgggccatc gcgatgtcgc    420
acggtacctg cgcgcggctg cgggggggcac cagaggcagt aaccatgccc gcatagatgc    480
cgcggaaggt ccctcagaca tccccgattg aaagaaccag agaggctctg agaaacctcg    540
ggaaacttag atcatcagtc accgaaggtc ctacagggcc acaactgccc ccgccacaac    600
ccaccccgct ttcgtagttt tcatttagaa aatagagctt ttaaaaatgt cctgcctttt    660
aacgtagata taagccttcc cccactaccg taaatgtcca tttatatcat tttttatata    720
ttcttataaa aatgtaaaaa agaaaaacac cgcttctgcc ttttcactgt gttggagttt    780
tctggagtga gcactcacgc cctaagcgca cattcatgtg ggcatttctt gcgagcctcg    840
cagcctccgg aagctgtcga cttcatgaca agcattttgt gaactaggga agctcagggg    900
ggttactggc ttctcttgag tcacactgct agcaaatggc agaaccaaag ctcaaataaa    960
aataaaataa ttttcattca ttcactc                                       987
```

<210> SEQ ID NO 28
<211> LENGTH: 156
<212> TYPE: PRT
<213> ORGANISM: Homo sapiens

<400> SEQUENCE: 28

```
Met Glu Pro Ala Ala Gly Ser Ser Met Glu Pro Ser Ala Asp Trp Leu
  1               5                  10                  15

Ala Thr Ala Ala Ala Arg Gly Arg Val Glu Glu Val Arg Ala Leu Leu
             20                  25                  30
```

Glu Ala Gly Ala Leu Pro Asn Ala Pro Asn Ser Tyr Gly Arg Arg Pro
            35                  40                  45

Ile Gln Val Met Met Met Gly Ser Ala Arg Val Ala Glu Leu Leu Leu
 50                  55                  60

Leu His Gly Ala Glu Pro Asn Cys Ala Asp Pro Ala Thr Leu Thr Arg
 65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
                100                 105                 110

Leu Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
130                 135                 140

Ile Asp Ala Ala Glu Gly Pro Ser Asp Ile Pro Asp
145                 150                 155

<210> SEQ ID NO 29
<211> LENGTH: 972
<212> TYPE: DNA
<213> ORGANISM: Homo sapiens

<400> SEQUENCE: 29

| | | | | | | |
|---|---|---|---|---|---|---|
| atggccctgt | ggatgcgcct | cctgcccctg | ctggcgctgc | tggccctctg | gggacctgac | 60 |
| ccagccgcag | ccatggagct | ggtagatcct | aacctagagc | cttggaatca | tccggggagt | 120 |
| cagcctacga | ctgcttgtag | caagtgttac | tgtaaaaaat | gttgctggca | ttgccaacta | 180 |
| tgctttctga | aaaaaggctt | aggcatctcc | catggcagga | agaagcggaa | gcaccgacga | 240 |
| agaactcctc | agagcagtaa | agatcatcaa | tatcctatac | cagagcaagc | caagcccctcg | 300 |
| gcctgcagga | acctcttcgg | cccggtggac | cacgaagagt | taacccggga | cttggagaag | 360 |
| cactgcagag | acatggaaga | ggcgagccag | cgcaagtgga | atttcgattt | tcagaatcac | 420 |
| aaacccctag | agggcaagta | cgagtggcaa | gaggtggaga | agggcagctt | gcccgagttc | 480 |
| tactacagac | ccccgcgggt | cgaggatccg | gcggcgggga | gcagcatgga | gccttcggct | 540 |
| gactggctgg | ccacggccgc | ggcccggggt | cgggtagagg | aggtgcgggc | gctgctggag | 600 |
| gcggggcgc | tgcccaacgc | accgaatagt | tacggtcgga | ggccgatcca | ggtcatgatg | 660 |
| atgggcagcg | cccgagtggc | ggagctgctg | ctgctccacg | gcgcggagcc | caactgcgcc | 720 |
| gaccccgcca | ctctcacccg | acccgtgcac | gacgctgccc | gggagggctt | cctggacacg | 780 |
| ctggtggtgc | tgcaccgggc | cggggcgcgg | ctggacgtgc | gcgatgcctg | ggccgtctg | 840 |
| cccgtggacc | tggctgagga | gctgggccat | cgcgatgtcg | cacggtacct | gcgcgcggct | 900 |
| gcgggggca | ccagaggcag | taaccatgcc | cgcatagatg | ccgcggaagg | tccctcagac | 960 |
| atccccgatt | ga | | | | | 972 |

<210> SEQ ID NO 30
<211> LENGTH: 323
<212> TYPE: PRT
<213> ORGANISM: Homo sapiens

<400> SEQUENCE: 30

Met Ala Leu Trp Met Arg Leu Leu Pro Leu Leu Ala Leu Leu Ala Leu
 1               5                   10                  15

Trp Gly Pro Asp Pro Ala Ala Ala Met Glu Leu Val Asp Pro Asn Leu

```
                  20                  25                  30
Glu Pro Trp Asn His Pro Gly Ser Gln Pro Thr Thr Ala Cys Ser Lys
             35                  40                  45

Cys Tyr Cys Lys Lys Cys Cys Trp His Cys Gln Leu Cys Phe Leu Lys
         50                  55                  60

Lys Gly Leu Gly Ile Ser His Gly Arg Lys Arg Lys His Arg Arg
 65                  70                  75                  80

Arg Thr Pro Gln Ser Ser Lys Asp His Gln Tyr Pro Ile Pro Glu Gln
                 85                  90                  95

Ala Lys Pro Ser Ala Cys Arg Asn Leu Phe Gly Pro Val Asp His Glu
                100                 105                 110

Glu Leu Thr Arg Asp Leu Glu Lys His Cys Arg Asp Met Glu Glu Ala
            115                 120                 125

Ser Gln Arg Lys Trp Asn Phe Asp Phe Gln Asn His Lys Pro Leu Glu
        130                 135                 140

Gly Lys Tyr Glu Trp Gln Glu Val Glu Lys Gly Ser Leu Pro Glu Phe
145                 150                 155                 160

Tyr Tyr Arg Pro Pro Arg Val Glu Asp Pro Ala Ala Gly Ser Ser Met
                165                 170                 175

Glu Pro Ser Ala Asp Trp Leu Ala Thr Ala Ala Arg Gly Arg Val
            180                 185                 190

Glu Glu Val Arg Ala Leu Leu Glu Ala Gly Ala Leu Pro Asn Ala Pro
        195                 200                 205

Asn Ser Tyr Gly Arg Arg Pro Ile Gln Val Met Met Met Gly Ser Ala
    210                 215                 220

Arg Val Ala Glu Leu Leu Leu Leu His Gly Ala Glu Pro Asn Cys Ala
225                 230                 235                 240

Asp Pro Ala Thr Leu Thr Arg Pro Val His Asp Ala Ala Arg Glu Gly
                245                 250                 255

Phe Leu Asp Thr Leu Val Val Leu His Arg Ala Gly Ala Arg Leu Asp
            260                 265                 270

Val Arg Asp Ala Trp Gly Arg Leu Pro Val Asp Leu Ala Glu Glu Leu
        275                 280                 285

Gly His Arg Asp Val Ala Arg Tyr Leu Arg Ala Ala Gly Gly Thr
    290                 295                 300

Arg Gly Ser Asn His Ala Arg Ile Asp Ala Ala Glu Gly Pro Ser Asp
305                 310                 315                 320

Ile Pro Asp

<210> SEQ ID NO 31
<211> LENGTH: 1017
<212> TYPE: DNA
<213> ORGANISM: Homo sapiens

<400> SEQUENCE: 31
atggccctgt ggatgcgcct cctgcccctg ctggcgctgc tggccctctg gggacctgac      60
ccagccgcag ccatggagct ggtagatcct aacctagagc cttggaatca tccggggagt     120
cagcctacga ctgcttgtag caagtgttac tgtaaaaaat gttgctggca ttgccaacta     180
tgctttctga aaaaaggctt aggcatctcc catggcagga agaagcggaa gcaccgacga     240
agaactcctc agagcagtaa agatcatcaa tatcctatac agagcaaggt ggcgggggc      300 agcggggtg gcggttccgg cggggtgga tccgccaagc cctcggcctg caggaacctc       360
ttcggcccgg tggaccacga agagttaacc cgggacttgg agaagcactg cagagacatg     420
```

```
gaagaggcga gccagcgcaa gtggaatttc gattttcaga atcacaaacc cctagagggc    480
aagtacgagt ggcaagaggt ggagaagggc agcttgcccg agttctacta cagaccccg     540 cgggtcgagg atccggcggc ggggagcagc atggagcctt cggctgactg gctggccacg    600
gccgcggccc ggggtcgggt agaggaggtg cgggcgctgc tggaggcggg ggcgctgccc    660
aacgcaccga atagttacgg tcggaggccg atccaggtca tgatgatggg cagcgcccga    720
gtggcggagc tgctgctgct ccacggcgcg gagcccaact gcgccgaccc cgccactctc    780
acccgacccg tgcacgacgc tgcccgggag ggcttcctgg acacgctggt ggtgctgcac    840
cgggccgggg cgcggctgga cgtgcgcgat gcctggggcc gtctgcccgt ggacctggct    900
gaggagctgg gccatcgcga tgtcgcacgg tacctgcgcg cggctgcggg gggcaccaga    960
ggcagtaacc atgcccgcat agatgccgcg gaaggtccct cagacatccc cgattga     1017
```

<210> SEQ ID NO 32
<211> LENGTH: 337
<212> TYPE: PRT
<213> ORGANISM: Homo sapiens

<400> SEQUENCE: 32

```
Met Ala Leu Trp Met Arg Leu Leu Pro Leu Leu Ala Leu Leu Ala Leu
 1               5                  10                  15

Trp Gly Pro Asp Pro Ala Ala Ala Met Glu Leu Val Asp Pro Asn Leu
             20                  25                  30

Glu Pro Trp Asn His Pro Gly Ser Gln Pro Thr Thr Ala Cys Ser Lys
         35                  40                  45

Cys Tyr Cys Lys Lys Cys Cys Trp His Cys Gln Leu Cys Phe Leu Lys
     50                  55                  60

Lys Gly Leu Gly Ile Ser His Gly Arg Lys Lys Arg Lys His Arg Arg
 65                  70                  75                  80

Arg Thr Pro Gln Ser Ser Lys Asp His Gln Tyr Pro Ile Pro Glu Gln
                 85                  90                  95

Gly Gly Gly Gly Ser Gly Gly Gly Ser Gly Gly Gly Gly Ser Ala
            100                 105                 110

Lys Pro Ser Ala Cys Arg Asn Leu Phe Gly Pro Val Asp His Glu Glu
        115                 120                 125

Leu Thr Arg Asp Leu Glu Lys His Cys Arg Asp Met Glu Glu Ala Ser
    130                 135                 140

Gln Arg Lys Trp Asn Phe Asp Phe Gln Asn His Lys Pro Leu Glu Gly
145                 150                 155                 160

Lys Tyr Glu Trp Gln Glu Val Glu Lys Gly Ser Leu Pro Glu Phe Tyr
                165                 170                 175

Tyr Arg Pro Pro Arg Val Glu Asp Pro Ala Ala Gly Ser Ser Met Glu
            180                 185                 190

Pro Ser Ala Asp Trp Leu Ala Thr Ala Ala Ala Arg Gly Arg Val Glu
        195                 200                 205

Glu Val Arg Ala Leu Leu Glu Ala Gly Ala Leu Pro Asn Ala Pro Asn
    210                 215                 220

Ser Tyr Gly Arg Arg Pro Ile Gln Val Met Met Met Gly Ser Ala Arg
225                 230                 235                 240

Val Ala Glu Leu Leu Leu Leu His Gly Ala Glu Pro Asn Cys Ala Asp
                245                 250                 255

Pro Ala Thr Leu Thr Arg Pro Val His Asp Ala Ala Arg Glu Gly Phe
            260                 265                 270
```

-continued

```
Leu Asp Thr Leu Val Val Leu His Arg Ala Gly Ala Arg Leu Asp Val
        275                 280                 285

Arg Asp Ala Trp Gly Arg Leu Pro Val Asp Leu Ala Glu Glu Leu Gly
    290                 295                 300

His Arg Asp Val Ala Arg Tyr Leu Arg Ala Ala Gly Gly Thr Arg
305                 310                 315                 320

Gly Ser Asn His Ala Arg Ile Asp Ala Ala Glu Gly Pro Ser Asp Ile
            325                 330                 335

Pro
```